US 12,036,548 B2

(12) United States Patent
Karalis et al.

(10) Patent No.: US 12,036,548 B2
(45) Date of Patent: Jul. 16, 2024

(54) ORGANS-ON-CHIPS AS A PLATFORM FOR EPIGENETICS DISCOVERY

(71) Applicant: EMULATE, INC., Boston, MA (US)

(72) Inventors: Catherine Karalis, Brookline, MA (US); Ville Kujala, Medford, MA (US)

(73) Assignee: EMULATE, INC., Boston, MA (US)

( * ) Notice: Subject to any disclaimer, the term of this patent is extended or adjusted under 35 U.S.C. 154(b) by 954 days.

(21) Appl. No.: 16/997,509

(22) Filed: Aug. 19, 2020

(65) Prior Publication Data
US 2020/0408744 A1    Dec. 31, 2020

Related U.S. Application Data

(63) Continuation of application No. PCT/US2019/019250, filed on Feb. 22, 2019.

(60) Provisional application No. 62/634,618, filed on Feb. 23, 2018.

(51) Int. Cl.
| | |
|---|---|
| *B01L 3/00* | (2006.01) |
| *C12M 3/06* | (2006.01) |
| *C12Q 1/6809* | (2018.01) |
| *G01N 33/50* | (2006.01) |
| *C12M 1/12* | (2006.01) |

(52) U.S. Cl.
CPC ........... *B01L 3/5027* (2013.01); *C12M 23/16* (2013.01); *C12Q 1/6809* (2013.01); *G01N 33/5023* (2013.01); *G01N 33/5064* (2013.01); *G01N 33/5091* (2013.01); *B01L 2300/0819* (2013.01); *B01L 2400/0487* (2013.01); *C12M 25/02* (2013.01)

(58) Field of Classification Search
CPC ........... B01L 3/5027; B01L 2300/0819; B01L 2400/0487; B01L 3/502761; B01L 2200/0652; B01L 2200/12; B01L 2300/021; B01L 2300/0681; B01L 2300/088; B01L 3/00; C12M 23/16; C12M 25/02; C12Q 1/6809; G01N 33/5023; G01N 33/5064; G01N 33/5091; G01N 33/5076; G01N 33/54366; G01N 33/50
See application file for complete search history.

(56) References Cited

U.S. PATENT DOCUMENTS

| 8,241,855 B2 | 8/2012 | Berlin ........................... 435/6.12 |
| 2008/0091730 A1 | 4/2008 | Jung et al. ....................... 702/19 |
| 2010/0196929 A1 | 8/2010 | Rogiers et al. ............... 424/93.7 |
| 2014/0335496 A1 | 11/2014 | Grego et al. .................... 435/1.1 |
| 2015/0301058 A1 | 10/2015 | Schettini et al. .............. 436/518 |
| 2016/0243738 A1 | 8/2016 | Katrycz ......................... 264/294 |
| 2016/0326477 A1 | 11/2016 | Fernandez-Alcon et al. .. 435/29 |
| 2017/0087187 A1 | 3/2017 | Chang et al. .................. 435/325 |
| 2017/0101628 A1 | 4/2017 | Ingber et al. ............... 435/297.2 |
| 2017/0296626 A1 | 10/2017 | Tarnopolsky ................. 424/450 |

FOREIGN PATENT DOCUMENTS

| KR | 20170067128 | * | 6/2017 | ......... G01N 33/5005 |
| WO | WO/2010/009307 | | 1/2010 | |
| WO | WO/2012/118799 | | 9/2012 | |
| WO | WO-2013068600 A1 | * | 5/2013 | ......... A61K 31/7125 |
| WO | WO/2013/086486 | | 6/2013 | |
| WO | WO/2013/086502 | | 6/2013 | |
| WO | WO/2013/126774 | | 8/2013 | |
| WO | WO/2014/210354 | | 12/2014 | |
| WO | WO/2014/210364 | | 12/2014 | |
| WO | WO/2015/013332 | | 1/2015 | |
| WO | WO/2015/138032 | | 9/2015 | |
| WO | WO/2015/138034 | | 9/2015 | |
| WO | WO/2017/075294 | | 5/2017 | |
| WO | WO/2017/087940 | | 5/2017 | |

OTHER PUBLICATIONS

Caballero et al, Organ-on-chip models of cancer metastasis for future personalized medicine: From chip to the patient, 2017, Biomaterials, 98-115. (Year: 2017).*
Huber et al, Exosomes: emerging roles in communication between blood cells and vascular tissues during atherosclerosis, 26, Curr Opin Lipidol., 412-419. (Year: 2015).*
Machine translation of KR 20170067128 A document in English (Year: 2017).*
U.S. Appl. No. 61/839,702, filed Jun. 26, 2013, Ingber, D. E. et al.
U.S. Appl. No. 61/810,944, filed Apr. 11, 2013.
Aga, M et al. (2014) "Exosomal HIF1α supports invasive potential of nasopharyngeal carcinoma-associated LMP1-positive exosomes," *Oncogene* 33(37), 4613-4622.

(Continued)

*Primary Examiner* — Narayan K Bhat
(74) *Attorney, Agent, or Firm* — Medlen & Carroll, LLP

(57) ABSTRACT

The present invention relates to microfluidic fluidic devices, methods and systems for use in identifying epigenetic signatures in a range of sample types, e.g., cells established on a "chip" (including but not limited to single cell samples, cell populations, C cell layers and whole tissues, such as a biopsy), immune cells, cfDNA, exosomes, and the like. More specifically, in some embodiments, a microfluidic chip containing a sample is contacted with a test compound (e.g. DNA altering test compound, an RNA expression altering test compound, etc.) for use in providing a diagnostic epigenetic signature for that type of sample (or cell type) exposed to that specific test compound. In some embodiments, after contact with a test compound, effluent fluids (e.g. fluids exiting the "chip" that contacted the cells) are derived for testing as a "virtual blood draw." In some embodiments, epigenetic signatures include (but are not limited to) identifying specific combinations of modifications of chromosomes and specific modifications of DNA.

8 Claims, 29 Drawing Sheets
(5 of 29 Drawing Sheet(s) Filed in Color)

(56) References Cited

OTHER PUBLICATIONS

Aguilar, C. A. et al. (2013) "Micro- and nanoscale devices for the investigation of epigenetics and chromatin dynamics," *Nature Nanotechnology* 8(10), 709-718.
ATF. (2014) "List of Explosives Materials—2014," *Federal Register* 79(194), Tuesday, Oct. 7, 2014.
Barry, R. A. et al. (2009) "Direct-Write Assembly of 3D Hydrogel Scaffolds for Guided Cell Growth," *Advanced Materials* 21(23), 2407-2410.
Bhatia, S. N. et al. (2014) "Microfluidic organs-on-chips," *Nature Biotechnology* 32(8), 760-772.
Bischel, L. L. et al. (2012) "A Practical Method for Patterning Lumens through ECM Hydrogels via Viscous Finger Patterning," *Journal of Laboratory Automation* 17(2), 96-103.
Bliss, S. A. et al. (2016) "Mesenchymal Stem Cell-Derived Exosomes Stimulate Cycling Quiescence and Early Breast Cancer Dormancy in Bone Marrow," *Cancer Research* 76(19), 5832-5844.
Boelens, Mirjam C. et al. (2014) "Exosome Transfer from Stromal to Breast Cancer Cells Regulates Therapy Resistance Pathways," *Cell* 159(3), 499-513.
Brinkmann, K et al. (2017) "P3.02a-008 EML4-ALK in Plasma Exosomes from a Cohort of NSCLC Patients: Topic: ALK Biomarkers," *Journal of Thoracic Oncology* 12(1), S1163-S1164.
Caballero, D. et al. (2017) "Organ-on-chip models of cancer metastasis for future personalized medicine: From chip to the patient," *Biomaterials* 149, 98-115.
Chen, Y. et al. (2015) "Breast cancer resistance protein (BCRP)-containing circulating microvesicles contribute to chemoresistance in breast cancer," *Oncol Lett* 10(6), 3742-3748.
Ciravolo, V. et al. (2012) "Potential role of HER2-overexpressing exosomes in countering trastuzumab-based therapy," *Journal of Cellular Physiology* 227(2), 658-667.
Costa-Silva, B. et al. (2015) "Pancreatic cancer exosomes initiate pre-metastatic niche formation in the liver," *Nature Cell Biology* 17(6), 816-826.
Escudier, B. et al. (2005) "Vaccination of metastatic melanoma patients with autologous dendritic cell (DC) derived-exosomes: results of thefirst phase I clinical trial," *Journal of Translational Medicine* 3(1), 10.
Esser, J. et al. (2010) "Exosomes from human macrophages and dendritic cells contain enzymes for leukotriene biosynthesis and promote granulocyte migration," *Journal of Allergy and Clinical Immunology* 126(5), 1032-1040.e1034.
Gallo, A. et al. (2012) "The Majority of MicroRNAs Detectable in Serum and Saliva Is Concentrated in Exosomes," *PLoS One* 7(3), e30679.
Guo, W. et al. (2017) "Exosomes: New players in cancer (Review)," *Oncology Reports* 38(2), 665-675.
Hannafon, B. N. et al. (2016) "Plasma exosome microRNAs are indicative of breast cancer," *Breast Cancer Research* 18(1), 90.
Hanson Shepherd, J. N. et al. (2011) "3D Microperiodic Hydrogel Scaffolds for Robust Neuronal Cultures," *Advanced Functional Materials* 21(1), 47-54.
Hegi, M. E. et al. (2005) "MGMT Gene Silencing and Benefit from Temozolomide in Glioblastoma," *New England Journal of Medicine* 352(10), 997-1003.
Herland, A. et al. (2016) "Distinct Contributions of Astrocytes and Pericytes to Neuroinflammation Identified in a 3D Human Blood-Brain Barrier on a Chip," *PLoS One* 11(3), Article No. e0150360.
Hong, C. S. et al. (2014) "Isolation and Characterization of CD34+ Blast-Derived Exosomes in Acute Myeloid Leukemia," *PLoS One* 9(8), e103310.
Hoshino, A. et al. (2015) "Tumour exosome integrins determine organotropic metastasis," *Nature* 527(7578), 329-335.
Hou, L. et al. (2012) "Environmental chemical exposures and human epigenetics," *International Journal of Epidemiology* 41(1), 79-105.
Huang, Z. et al. (2017) "A novel serum microRNA signature to screen esophageal squamous cell carcinoma," *Cancer Medicine* 6(1), 109-119.
Huber, H. J. et al. (2015) "Exosomes: emerging roles in communication between blood cells and vascular tissues during atherosclerosis," *Current Opinion in Lipidology* 26(5), 412-419.
Işın, M. et al. (2015) "Exosomal lncRNA-p21 levels may help to distinguish prostate cancer from benign disease," *Frontiers in Genetics* 6.
Kamiguchi, N. et al. (2010) "A 96-Well Plate Assay for CYP4503A Induction Using Cryopreserved Human Hepatocytes," *Drug Metabolism and Disposition* 38(11), 1912.
Katakowski, M. et al. (2013) "Exosomes from marrow stromal cells expressing miR-146b inhibit glioma growth," *Cancer Letters* 335(1), 201-204.
Keller, S. et al. (2011) "Body fluid derived exosomes as a novel template for clinical diagnostics," *Journal of Translational Medicine* 9(1), 86.
Kim, M. S. et al. (2016) "Development of exosome-encapsulated paclitaxel to overcome MDR in cancer cells," *Nanomedicine: Nanotechnology, Biology and Medicine* 12(3), 655-664.
Kosaka, N et al. (2016) "Versatile roles of extracellular vesicles in cancer," *The Journal of Clinical Investigation* 126(4), 1163-1172.
Kuo, W. P. et al. (2017) "Red Blood Cells: A Source of Extracellular Vesicles," in *Extracellular Vesicles: Methods and Protocols* (Kuo, W. P., et al., Eds.), pp. 15-22, Springer New York, New York, NY.
Lau, .C et al. (2013) "Role of Pancreatic Cancer-derived Exosomes in Salivary Biomarker Development," *Journal of Biological Chemistry* 288(37), 26888-26897.
Lea, J. et al. (2017) "Detection of phosphatidylserine-positive exosomes as a diagnostic marker for ovarian malignancies: a proof of concept study," *Oncotarget* 8(9).
Li, Q. et al. (2015) "Plasma long noncoding RNA protected by exosomes as a potential stable biomarker for gastric cancer," *Tumor Biology* 36(3), 2007-2012.
Li, Y. et al. (2015) "Circular RNA is enriched and stable in exosomes: a promising biomarker for cancer diagnosis," *Cell Research* 25(8), 981-984.
Lin, Y. et al. (2017) "Differentiation, Evaluation, and Application of Human Induced Pluripotent Stem Cell-Derived Endothelial Cells," *Arteriosclerosis, Thrombosis, and Vascular Biology* 37(11), 2014-2025.
Liu, C. et al. (2016) "Serum exosomal miR-4772-3p is a predictor of tumor recurrence in stage II and III colon cancer," *Oncotarget* 7(46).
Liu, Q. et al. (2016) "Circulating exosomal microRNAs as prognostic biomarkers for non-small-cell lung cancer," *Oncotarget* 8(8).
Liu, T. et al. (2016) "Exosomal long noncoding RNA CRNDE-h as a novel serum-based biomarker for diagnosis and prognosis of colorectal cancer," *Oncotarget* 7(51).
Liu, Y. et al. (2016) "Tumor Exosomal RNAs Promote Lung Pre-metastatic Niche Formation by Activating Alveolar Epithelial TLR3 to Recruit Neutrophils," *Cancer Cell* 30(2), 243-256.
Logozzi, M. et al. (2009) "High Levels of Exosomes Expressing CD63 and Caveolin-1 in Plasma of Melanoma Patients," *PLoS One* 4(4), e5219.
Madhavan, B. et al. (2015) "Combined evaluation of a panel of protein and miRNA serum-exosome biomarkers for pancreatic cancer diagnosis increases sensitivity and specificity," *International Journal of Cancer* 136(11), 2616-2627.
Manier, S. et al. (2017) "Prognostic role of circulating exosomal miRNAs in multiple myeloma," *Blood* 129(17), 2429-2436.
Maoz, B. M. et al. (2018) "A linked organ-on-chip model of the human neurovascular unit reveals the metabolic coupling of endothelial and neuronal cells," *Nature Biotechnology* 36(9), 865-874.
Maoz, B. M. et al. (2017) "Organs-on-Chips with combined multielectrode array and transepithelial electrical resistance measurement capabilities," *Lab on a Chip* 17(13), 2294-2302.
Marleau, A. M. et al. (2012) "Exosome removal as a therapeutic adjuvant in cancer," *Journal of Translational Medicine* 10(1), 134.
Matsumoto, Y. et al. (2016) "Quantification of plasma exosome is a potential prognostic marker for esophageal squamous cell carcinoma," *Oncology Reports* 36(5), 2535-2543.

(56) References Cited

OTHER PUBLICATIONS

Matsumura, T. et al. (2015) "Exosomal microRNA in serum is a novel biomarker of recurrence in human colorectal cancer," *British Journal of Cancer* 113(2), 275-281.
Melegari, S. P. et al. (2015) "Evaluation of Cytotoxicity and Cell Death Induced In Vitro by Saxitoxin in Mammalian Cells," *Journal of Toxicology and Environmental Health, Part A* 78(19), 1189-1200.
Melo, S. A. et al. (2015) "Glypican-1 identifies cancer exosomes and detects early pancreatic cancer," *Nature* 523(7559), 177-182.
Meunier, V. et al. (1995) "The human intestinal epithelial cell line Caco-2; pharmacological and pharmacokinetic applications," *Cell Biology and Toxicology* 11(3), 187-194.
Mirzaei, H. et al. (2018) "State of the art in microRNA as diagnostic and therapeutic biomarkers in chronic lymphocytic leukemia," *Journal of Cellular Physiology* 233(2), 888-900.
Morse, M. A. et al. (2005) "A phase I study of dexosome immunotherapy in patients with advanced non-small cell lung cancer," *Journal of Translational Medicine* 3(1), 9.
Ogata-Kawata, H. et al. (2014) "Circulating Exosomal microRNAs as Biomarkers of Colon Cancer," *PLoS One* 9(4), e92921.
Ono, M. et al. (2014) "Exosomes from bone marrow mesenchymal stem cells contain a microRNA that promotes dormancy in metastatic breast cancer cells," *Science Signaling* 7(332), ra63-ra63.
Pascucci, L. et al. (2014) "Paclitaxel is incorporated by mesenchymal stromal cells and released in exosomes that inhibit in vitro tumor growth: A new approach for drug delivery," *Journal of Controlled Release* 192, 262-270.
Pisitkun, T. et al. (2004) "Identification and proteomic profiling of exosomes in human urine," *Proceedings of the National Academy of Sciences* 101(36), 13368-13373.
Raposo, G. et al. (2013) "Extracellular vesicles: Exosomes, microvesicles, and friends," *Journal of Cell Biology* 200(4), 373-383.
Richards, K. E. et al. (2017) "Cancer-associated fibroblast exosomes regulate survival and proliferation of pancreatic cancer cells," *Oncogene* 36(13), 1770-1778.
Rodríguez, M. et al. (2014) "Different exosome cargo from plasma/bronchoalveolar lavage in non-small-cell lung cancer," *Genes, Chromosomes and Cancer* 53(9), 713-724.
Sadri-Vakili, G. (2015) "Cocaine triggers epigenetic alterations in the corticostriatal circuit," *Brain Research* 1628(Pt A), 50-59.
Sances, S. et al. (2018) "Human iPSC-Derived Endothelial Cells and Microengineered Organ-Chip Enhance Neuronal Development," *Stem Cell Reports* 10(4), 1222-1236.
Sandfeld-Paulsen, B. et al. (2016) "Exosomal proteins as prognostic biomarkers in non-small cell lung cancer," *Molecular Oncology* 10(10), 1595-1602.
Shao, H. et al. (2015) "Chip-based analysis of exosomal mRNA mediating drug resistance in glioblastoma," *Nature Communications* 6(1), 6999.
Sharma, R. et al. (2017) "Detection of phosphatidylserine-positive exosomes for the diagnosis of early-stage malignancies," *British Journal of Cancer* 117(4), 545-552.
Shedden, K. et al. (2003) "Expulsion of Small Molecules in Vesicles Shed by Cancer Cells: Association with Gene Expression and Chemosensitivity Profiles," *Cancer Research* 63(15), 4331-4337.
Sohn, W. et al. (2015) "Serum exosomal microRNAs as novel biomarkers for hepatocellular carcinoma," *Experimental & Molecular Medicine* 47(9), e184-e184.

Sugimachi, K. et al. (2015) "Identification of a bona fide microRNA biomarker in serum exosomes that predicts hepatocellular carcinoma recurrence after liver transplantation," *British Journal of Cancer* 112(3), 532-538.
Sun, L. et al. (2012) "Direct-Write Assembly of 3D Silk/Hydroxyapatite Scaffolds for Bone Co-Cultures," *Advanced Healthcare Materials* 1(6), 729-735.
Taylor, D. D. et al. (2008) "MicroRNA signatures of tumor-derived exosomes as diagnostic biomarkers of ovarian cancer," *Gynecologic Oncology* 110(1), 13-21.
Thangawng, A. L. et al. (2007) "An ultra-thin PDMS membrane as a bio/micro-nano interface: fabrication and characterization," *Biomedical Microdevices* 9(4), 587-595.
The Encode Project Consortium. (2011) "A User's Guide to the Encyclopedia of DNA Elements (ENCODE)," *PLOS Biology* 9(4), e1001046.
Tian, Y. et al. (2014) "A doxorubicin delivery platform using engineered natural membrane vesicle exosomes for targeted tumor therapy," *Biomaterials* 35(7), 2383-2390.
Tominaga, N. et al. (2015) "Brain metastatic cancer cells release microRNA-181c-containing extracellular vesicles capable of destructing blood-brain barrier," *Nature Communications* 6(1), 6716.
Tshala-Katumbay, D. D. et al. (2016) "Cyanide and the human brain: perspectives from a model of food (cassava) poisoning," *Annals of the New York Academy of Sciences* 1378(1), 50-57.
Wang, G. et al. (2014) "Modeling the mitochondrial cardiomyopathy of Barth syndrome with induced pluripotent stem cell and heart-on-chip technologies," *Nature Medicine* 20(6), 616-623.
Wang, H. et al. (2014) "Expression of Serum Exosomal MicroRNA-21 in Human Hepatocellular Carcinoma," *BioMed Research International* 2014, 864894.
Wang, T. et al. (2017) "Increasing circulating exosomes-carrying TRPC5 predicts chemoresistance in metastatic breast cancer patients," *Cancer Science* 108(3), 448-454.
Whitesides, G. M. et al. (2001) "Soft Lithography in Biology and Biochemistry," *Annual Review of Biomedical Engineering* 3(1), 335-373.
Wu, W. et al. (2011) "Omnidirectional Printing of 3D Microvascular Networks," *Advanced Materials* 23(24), H178-H183.
Wu, W. et al. (2010) "Direct-write assembly of biomimetic microvascular networks for efficient fluid transport," *Soft Matter* 6(4), 739-742.
Wu, Z. et al. (2016) "Exosomes: small vesicles with big roles in hepatocellular carcinoma," *Oncotarget* 7(37).
Wunsch, B. H. et al. (2016) "Nanoscale lateral displacement arrays for the separation of exosomes and colloids down to 20 nm," *Nature Nanotechnology* 11(11), 936-940.
Ye, S.-B. et al. (2016) "Exosomal miR-24-3p impedes T-cell function by targeting FGF11 and serves as a potential prognostic biomarker for nasopharyngeal carcinoma," *The Journal of Pathology* 240(3), 329-340.
Zhang, B. et al. (2017) "Organ-on-a-chip devices advance to market," *Lab on a Chip* 17(14), 2395-2420.
Zhang, L. et al. (2015) "Microenvironment-induced PTEN loss by exosomal microRNA primes brain metastasis outgrowth," *Nature* 527(7576), 100-104.
Zhang, X. et al. (2015) "Exosomes in cancer: small particle, big player," *Journal of Hematology and Oncology* 8(1), 83.
Zhou, X. et al. (2016) "A six-microRNA panel in plasma was identified as a potential biomarker for lung adenocarcinoma diagnosis," *Oncotarget* 8(4).
Zhu, M. et al. (2017) "A panel of microRNA signature in serum for colorectal cancer diagnosis," *Oncotarget* 8(10).
PCT International Search Report of International Application No. PCT/US2019/019250 dated May 15, 2019.

\* cited by examiner

Fig. 1A
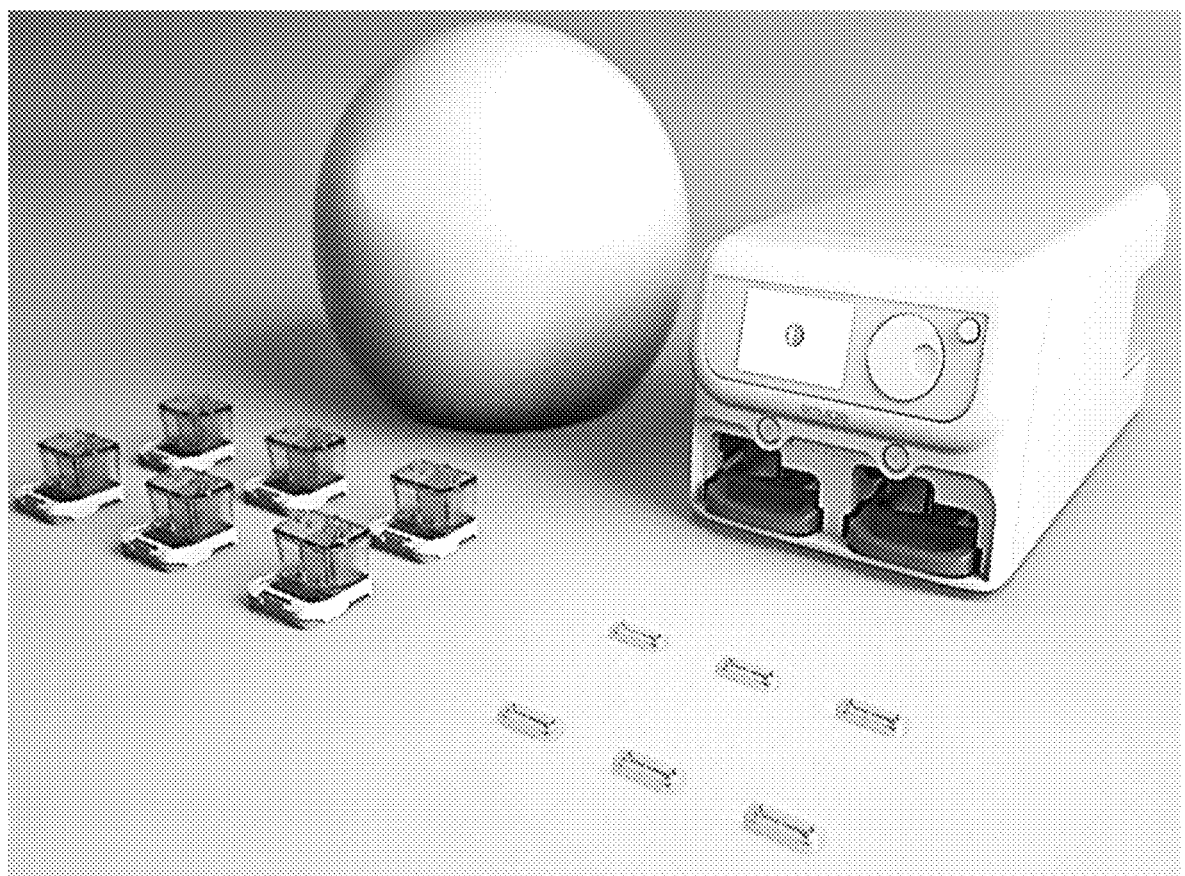
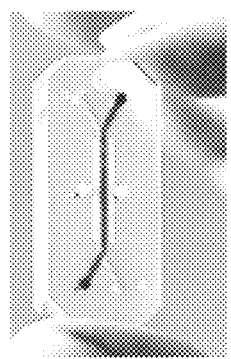

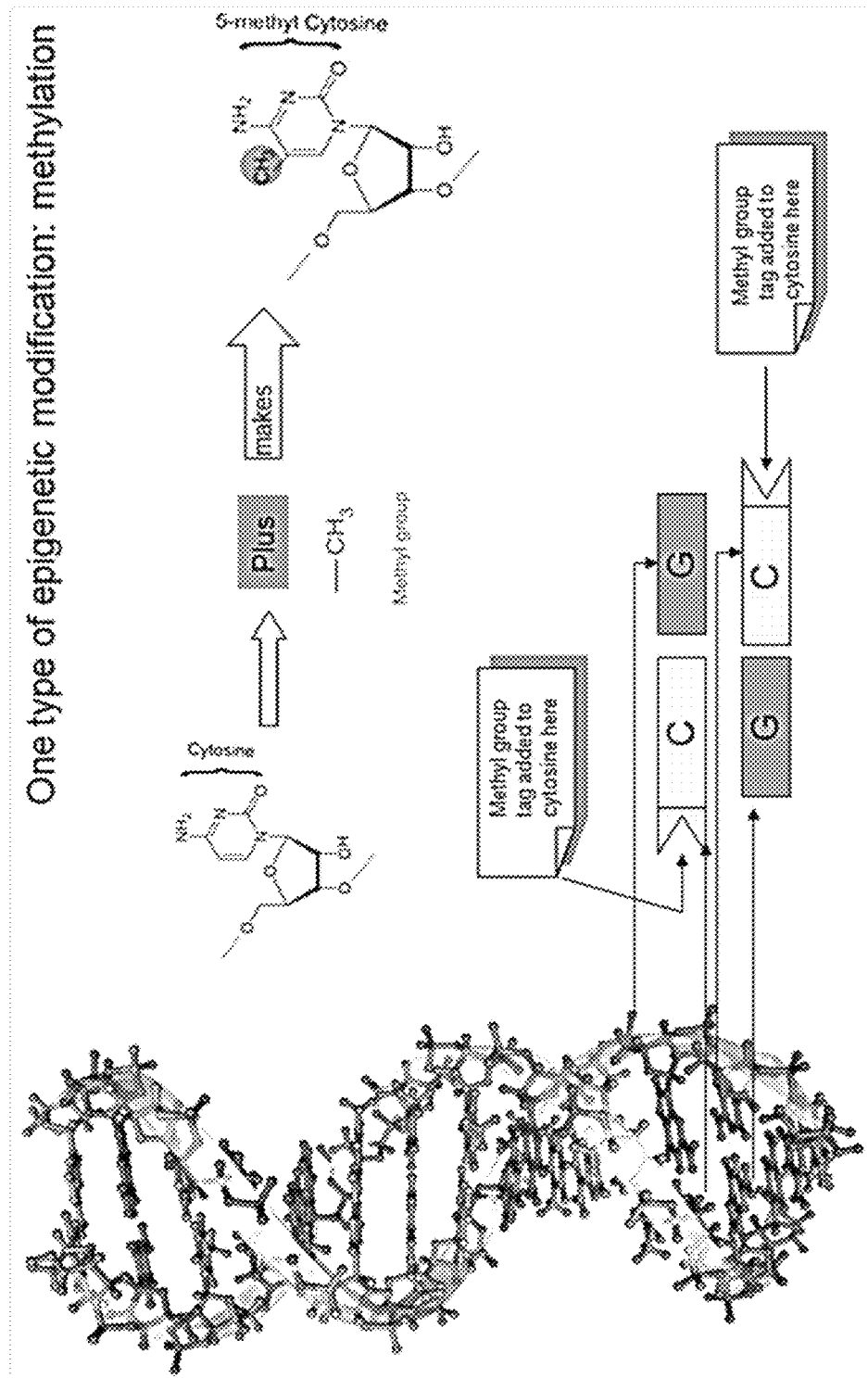

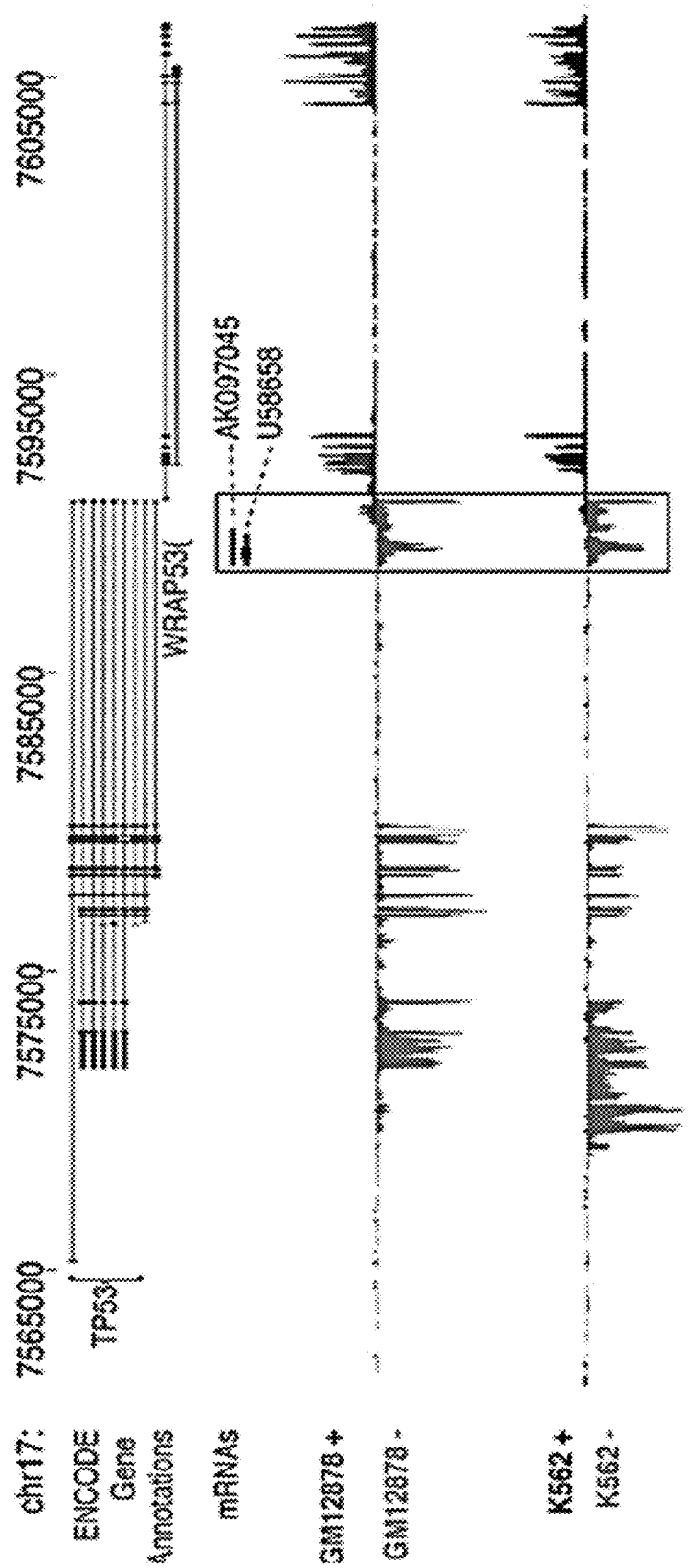

Fig. 11A
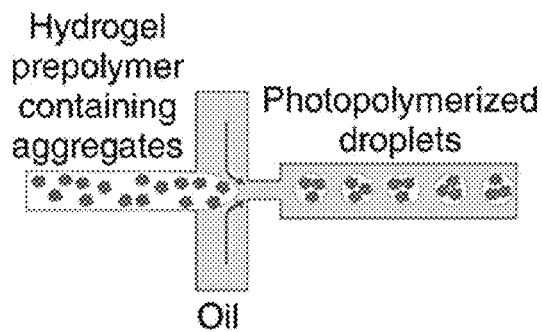
Fig. 11B
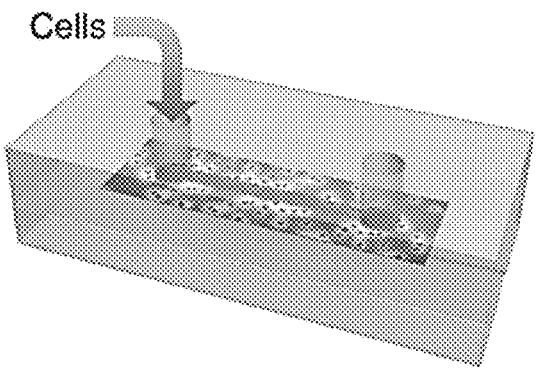
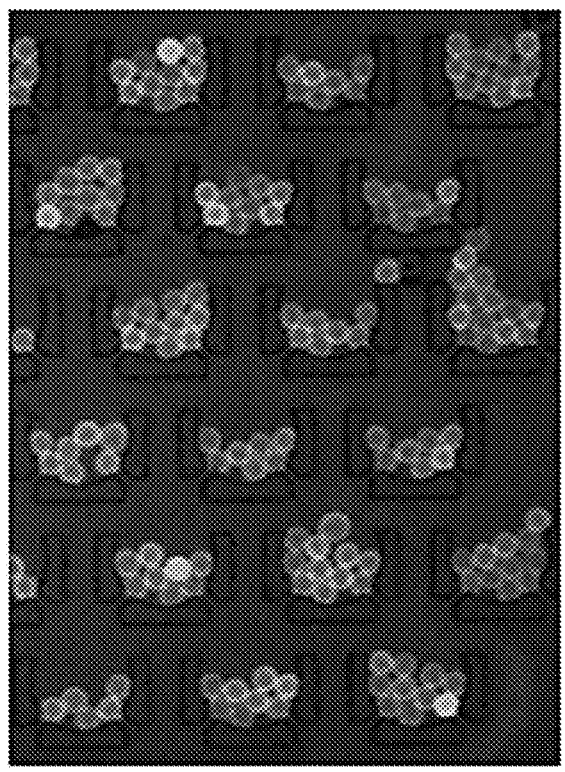
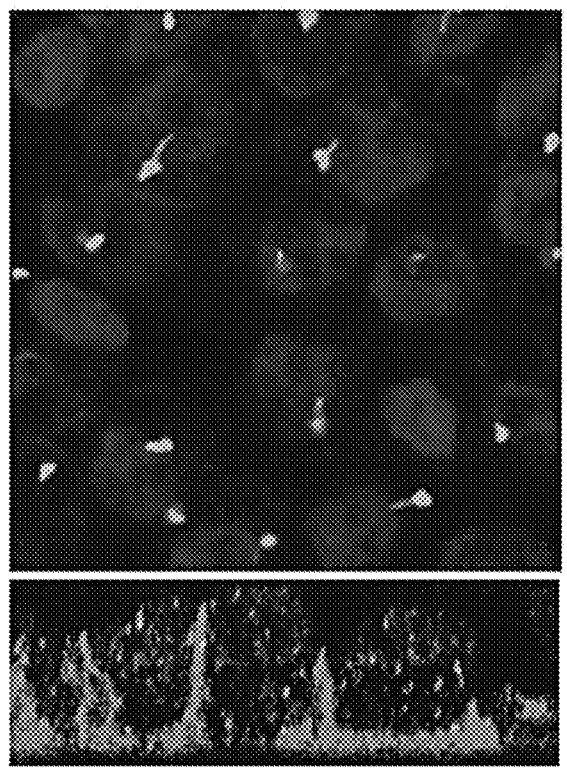

Fig. 11C
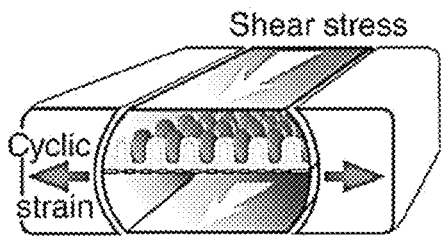
Fig. 11D
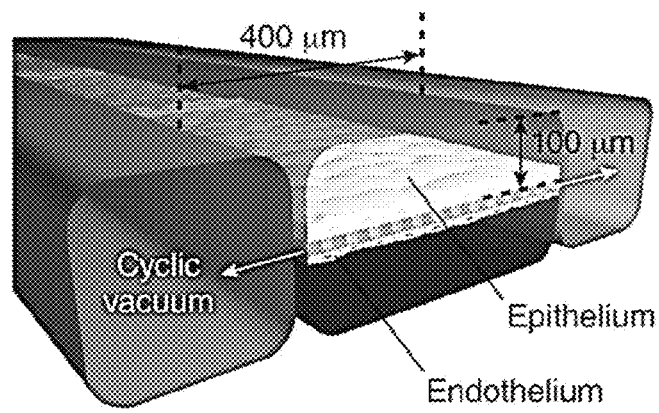
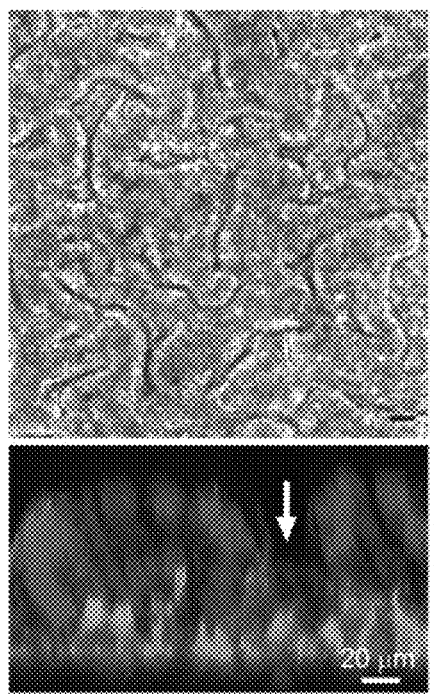
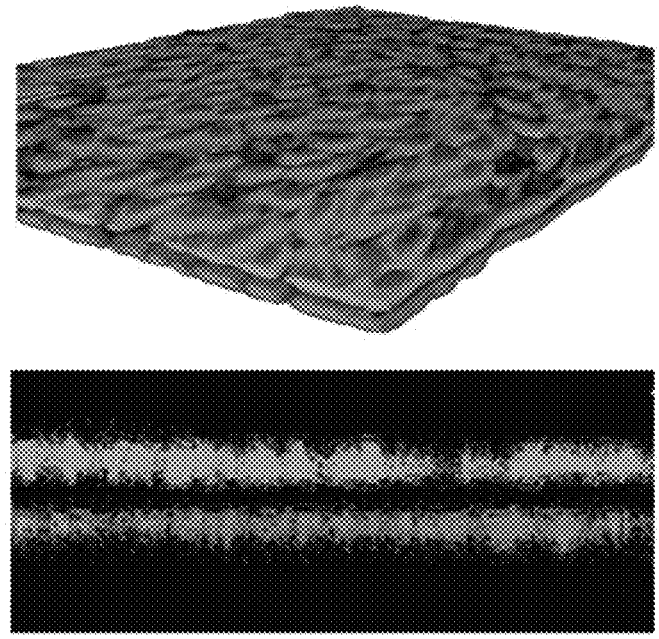

Fig. 12B
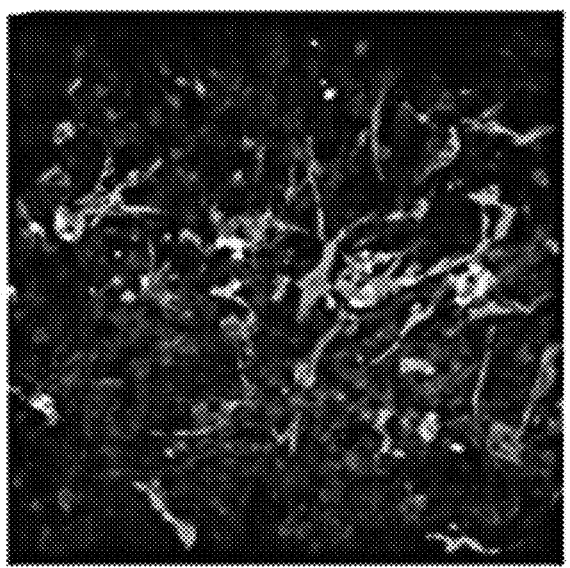
Fig. 12C
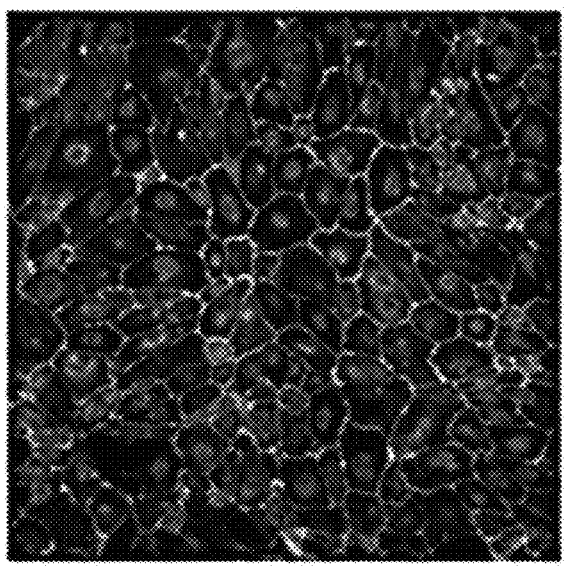
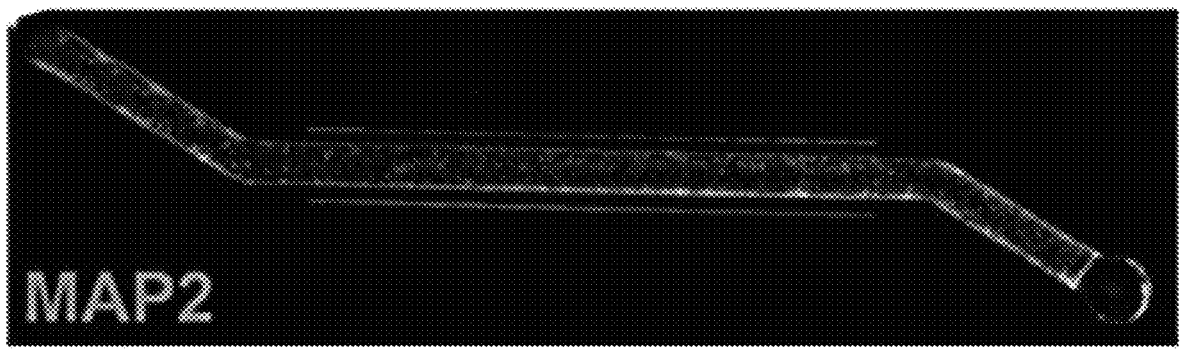
Fig. 12D

Fig. 13
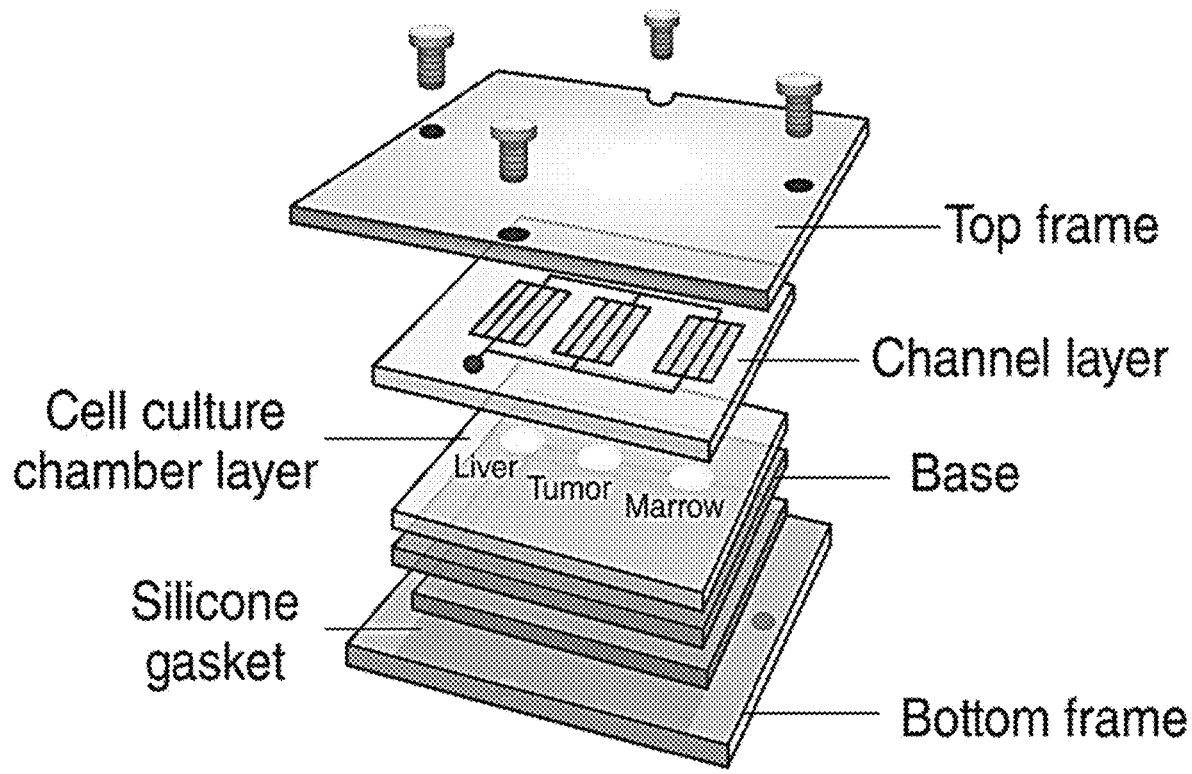
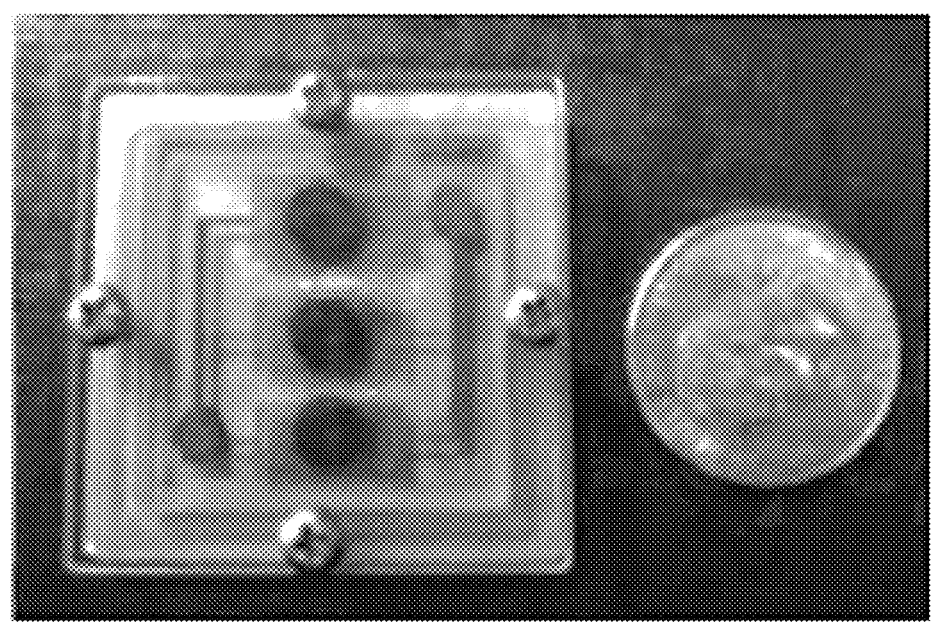

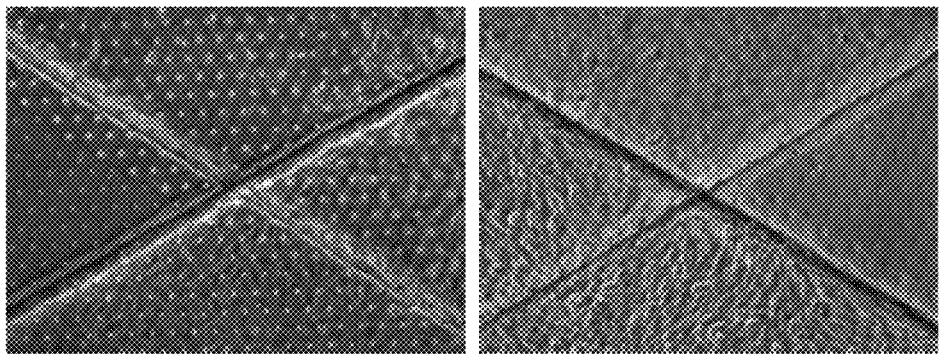
Fig. 16A
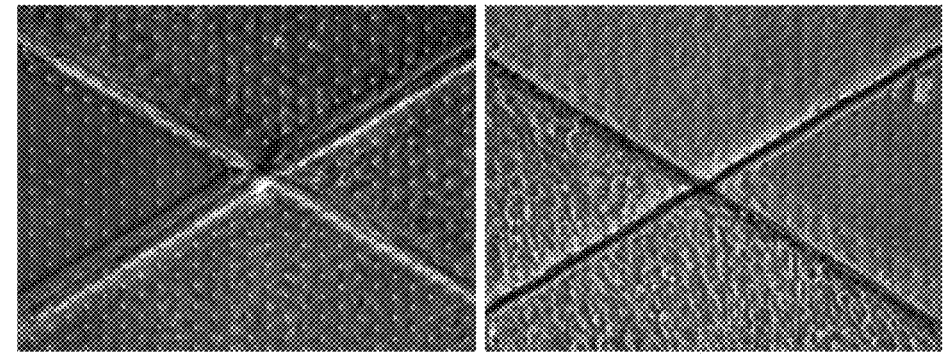
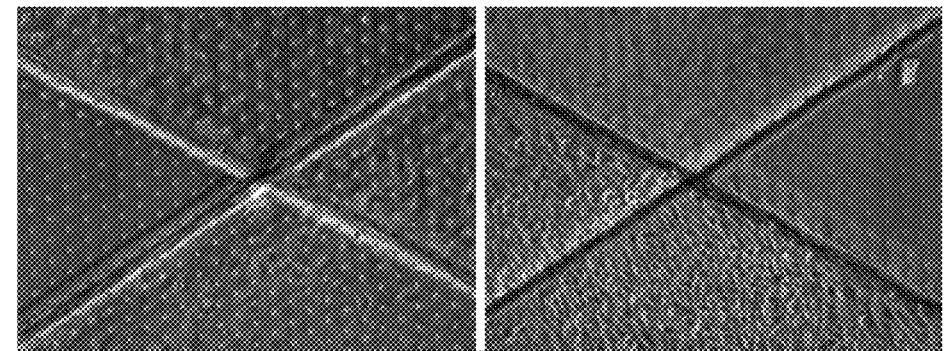
FIG. 16B

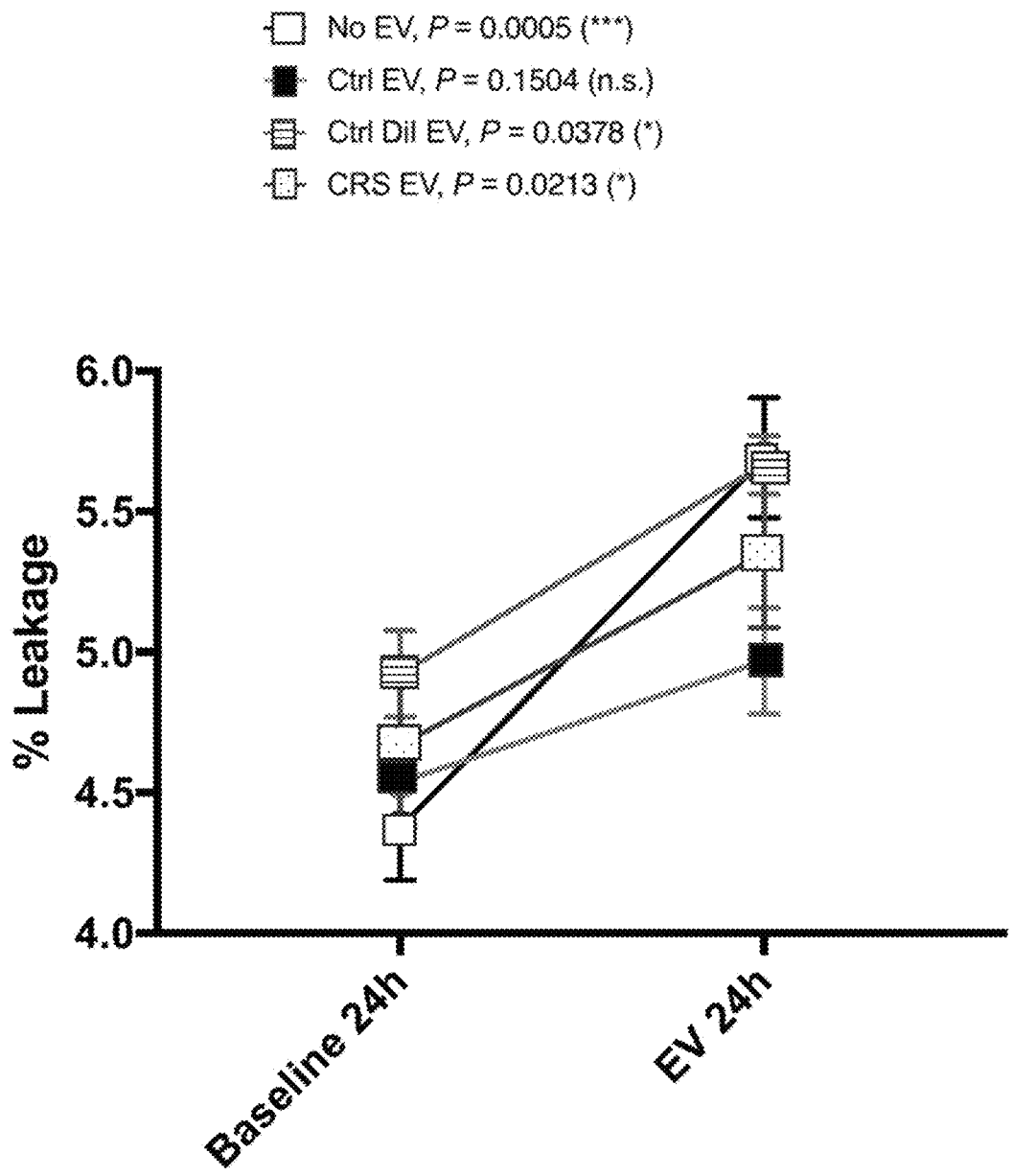

Fig. 21A
Fig. 21B
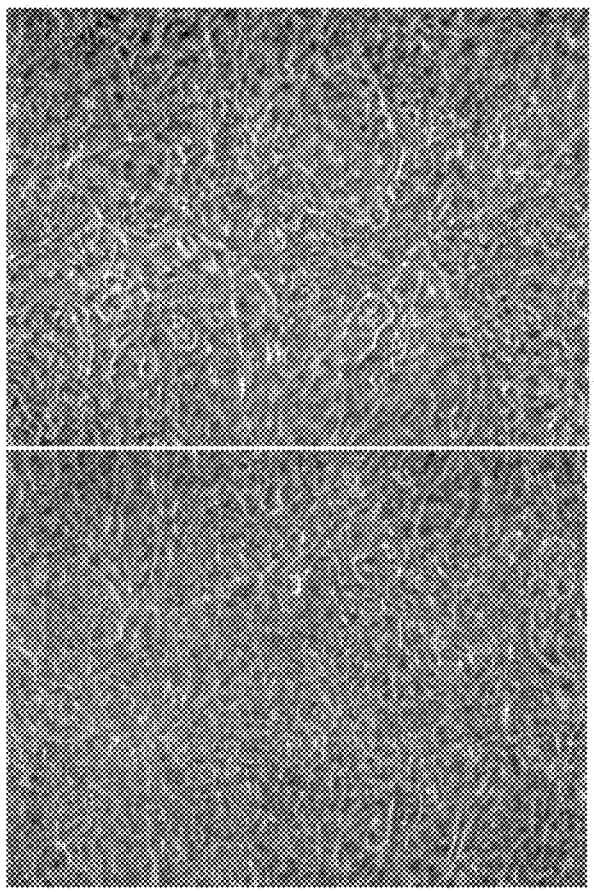
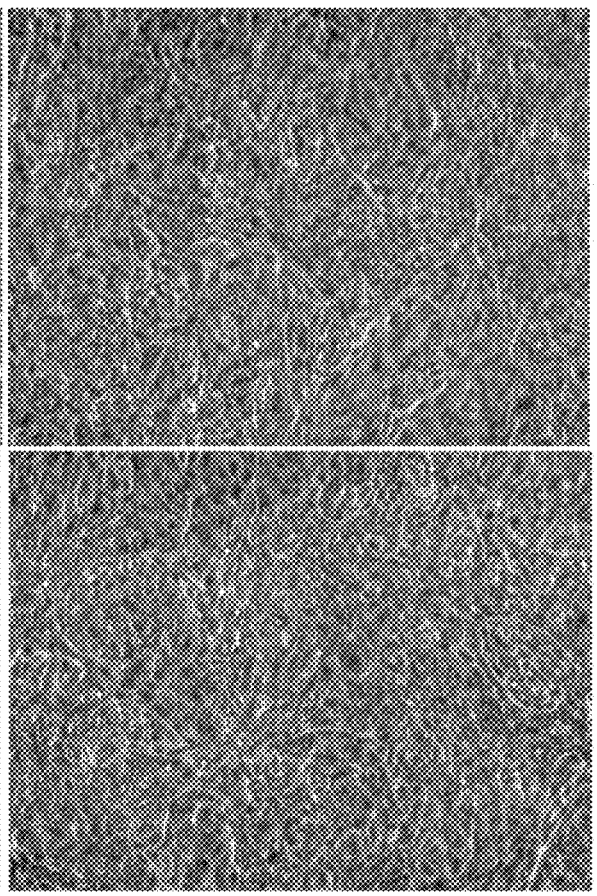

ORGANS-ON-CHIPS AS A PLATFORM FOR EPIGENETICS DISCOVERY

CROSS-REFERENCE TO RELATED APPLICATIONS

The present application is a Continuation of, and claims priority to, PCT Patent Application Serial No. PCT/US2019/019250, filed Feb. 22, 2019, which claims priority to Provisional Application Ser. No. 62/634,618 filed on Feb. 23, 2018, the contents of which are incorporated herein in their entirety.

FIELD OF THE INVENTION

The present invention relates to microfluidic fluidic devices, methods and systems for use in identifying epigenetic signatures in a range of sample types, e.g., cells established on a "chip" (including but not limited to single cell samples, cell populations, cell layers and whole tissues, such as a biopsy), immune cells, cfDNA, exosomes, and the like. More specifically, in some embodiments, a microfluidic chip containing a sample is contacted with a test compound (e.g. DNA altering test compound, an RNA expression altering test compound, etc.) for use in providing a diagnostic epigenetic signature for that type of sample (or cell type) exposed to that specific test compound. In some embodiments, after contact with a test compound, effluent fluids (e.g. fluids exiting the "chip" that contacted the cells) are derived for testing as a "virtual blood draw." In some embodiments, epigenetic signatures include (but are not limited to) identifying specific combinations of modifications of chromosomes and specific modifications of DNA.

BACKGROUND

Changes in the packaging and modifications of DNA in and around the genome of a cell have been shown to exert significant influence on cellular behavior and in turn, human development and disease. Such changes are referred to as epigenetic modifications as opposed to DNA sequence modifications whereby a disease allele containing at least one altered nucleotide as a point mutation, deletion or addition, may be associated with a particular disease.

Getting epigenetic signatures that are relevant to humans is difficult. The use of animal models or clinical samples has many drawbacks. Animal models and resulting epigenetic signature information may have very limited relevance to humans in that they have been shown to poorly predict effects in humans. After all, there are substantial differences between animal vs. human chromosomal morphology and physiology. Using human clinical samples does not remedy this problem. Clinical samples have too many variables associated with their condition (not to mention the variability human to human) rendering an epigenetic signature having a questionable association with one particular condition.

Thus, there is a need to control variables associated with a particular human epigenetic signature. Furthermore, what is needed is a better platform for detecting epigenetic events, and then associating these epigenetic signatures with a particular variable or condition.

SUMMARY OF THE INVENTION

The present invention relates to microfluidic fluidic devices, methods and systems for use in identifying epigenetic signatures in a range of sample types, e.g., cells established on a "chip" (including but not limited to single cell samples, cell populations, cell layers and whole tissues, such as a biopsy), immune cells, cfDNA, exosomes, and the like. More specifically, in some embodiments, a microfluidic chip containing a sample is contacted with a test compound (e.g. DNA altering test compound, an RNA expression altering test compound, etc.) for use in providing a diagnostic epigenetic signature for that type of sample (or cell type) exposed to that specific test compound. In some embodiments, after contact with a test compound, effluent fluids (e.g. fluids exiting the "chip" that contacted the cells) are derived for testing as a "virtual blood draw." In some embodiments, epigenetic signatures include (but are not limited to) identifying specific combinations of modifications of chromosomes and specific modifications of DNA.

In one embodiment, the present invention contemplates a method comprising: a) a microfluidic device comprising at least one microfluidic channel (or chamber), said microfluidic channel comprising one or more cell types; and b) a plurality of extracellular vesicles; c) introducing said extracellular vesicles into said microfluidic channel under conditions wherein said cells are exposed to said extracellular vesicles so as to create one or more exposed cells; and d) detecting the uptake of one or more extracellular vesicles in one or more exposed cells. In one embodiment, said uptake is compared to the uptake in different cells (e.g. a control). In one embodiment, said method further comprises flowing media at a flow rate through said microfluidic channel prior to step c). In one embodiment, said extracellular vesicles are introduced by adding them to said flowing media. In one embodiment, extracellular vesicles added to the flowing media that are not taken up by the cells are collected as they exit the microchannel. In one embodiment, said extracellular vesicles were obtained from a second microfluidic device comprising cultured cells. In one embodiment, said method further comprises e) assessing the amount of uptake. In one embodiment, said method further comprises e) detecting a change in one or more exposed cells. In one embodiment, said method further comprises e) detecting cell injury in one or more exposed cells. In one embodiment, said uptake is cell-type specific. It is not intended that the present invention be limited to the nature of the one or more cell types. In one embodiment, said one or more cell types are kidney cells. In one embodiment, said detecting of cell uptake is done by, prior to step c), labeling said extracellular vesicles with a dye. In one embodiment, said dye is a fluorescent lipophilic cationic indocarbocyanine dye. In one embodiment, said fluorescent lipophilic cationic indocarbocyanine dye is 1,1'-Dioctadecyl-3,3,3',3'-Tetramethylindocarbocyanine Perchlorate. In one embodiment, said extracellular vesicles comprise nucleic acid. In one embodiment, said extracellular vesicles were obtained from a human patient. In one embodiment, said human patient has a disease or condition. In one embodiment, said human patient has a heart condition. In one embodiment, said extracellular vesicles were obtained from cells in culture. In one embodiment, said extracellular vesicles were obtained from a second microfluidic device comprising human cells. In one embodiment, said human cells are heart cells.

In one embodiment, the present invention contemplates a method comprising: i) a microfluidic device comprising at least one microfluidic channel, said microfluidic channel comprising one or more cell types; and b) a plurality of extracellular vesicles; c) introducing said extracellular vesicles into said microfluidic channel under conditions wherein said cells are exposed to said extracellular vesicles so as to create one or more exposed cells; and d) assessing the epigenetic profile of one or more exposed cells. In one embodiment, said profile is compared to the profile in different cells (e.g. a control). In one embodiment, said method further comprises step d) identifying changes in the transcriptome of one or more exposed cells. In one embodiment, said changes comprise cell-type specific changes in the transcriptome of one or more exposed cells. It is not intended that the present invention be limited by the nature of the one or more exposed cells. In one embodiment, said d one or more cell types comprise kidney cells (or lung cells, heart cells, etc.). In one embodiment, said one or more cell types comprise brain cells. In one embodiment, said brain cells comprise brain parenchyma cells. In one embodiment, said one or more cells comprise endothelial cells. In one embodiment, said endothelial cells are hiPSC-derived endothelial cells. In one embodiment, said method further comprises flowing media at a flow rate through said microfluidic channel prior to step c). In one embodiment, said extracellular vesicles are introduced by adding them to said flowing media. In one embodiment, said extracellular vesicles were obtained from a human patient. In one embodiment, said human patient has a disease or condition. In one embodiment, said human patient has a heart condition. In one embodiment, said extracellular vesicles were obtained from cells in culture. In one embodiment, said extracellular vesicles were obtained from a second microfluidic device comprising human cells. In one embodiment, said human cells are heart cells. In one embodiment, said extracellular vesicles were obtained from cancer cells in culture. In one embodiment, said extracellular vesicles were obtained from a microfluidic device comprising at least one microfluidic channel and one or more cancer cells. In one embodiment, said extracellular vesicles were obtained from hematopoietic cells. In one embodiment, said extracellular vesicles were obtained from human red blood cells. In one embodiment, said method further comprises step e) using said epigenetic profile for predicting a clinical symptom in a human brain cancer patient. In one embodiment, said microchannel comprises a membrane.

In one embodiment, the present invention contemplates a method comprising: a) a microfluidic device comprising at least one microfluidic channel, said microfluidic channel comprising cells of a first cell type; and b) a plurality of extracellular vesicles; c) introducing said extracellular vesicles into said microfluidic channel under conditions wherein said cells are exposed to said extracellular vesicles so as to create exposed cells of a first cell type; d) determining whether said extracellular vesicles are selective to said exposed cells of a first cell type. In one embodiment, said determining of step d) comprises detecting the uptake of one or more extracellular vesicles in said exposed cells of a first cell type. In one embodiment, said uptake is compared against the uptake in cells of a second cell type (which can be a positive or negative control). In one embodiment, said cells of a first cell type are derived from a first organ and said cells of a second cell type are derived from a second organ. It is not intended that the present invention be limited to the nature or type of the first organ or second organ. A variety of organ types are contemplated. In one embodiment, said first organ is the lung and said second organ is the liver. In one embodiment, said first organ is the heart and said second organ is the kidney. In one embodiment, said detecting of cell uptake is done by, prior to step c), labeling said extracellular vesicles with a dye. In one embodiment, said dye is a fluorescent lipophilic cationic indocarbocyanine dye. In one embodiment, said extracellular vesicles comprise nucleic acid. In one embodiment, said extracellular vesicles were obtained from a human patient. In one embodiment, said human patient has a disease or condition. In one embodiment, said human patient has a heart condition. In one embodiment, said extracellular vesicles were obtained from cells in culture. In one embodiment, said extracellular vesicles were obtained from a second microfluidic device comprising human cells. In one embodiment, said human cells are heart cells. In one embodiment, said method further comprises flowing media at a flow rate through said microfluidic channel prior to step c). In one embodiment, said extracellular vesicles are introduced by adding them to said flowing media. In one embodiment, said method further comprises the step of detecting extracellular vesicles that have flowed completely through said microfluidic channel. In one embodiment, said method further comprises the step of collecting extracellular vesicles that have flowed completely through said microfluidic channel.

In one embodiment, the present invention contemplates a method comprising: a) providing; i) a microfluidic device comprising at least one microfluidic channel and one or more cell types; and ii) an agent selected from the group including but not limited to a toxin, chemical, toxic chemical, toxic chemical precursors, chemical weapon, radioisotope, drug and pathogen; b) introducing said agent said microfluidic channel under conditions wherein said cells are exposed to said agent so as to create one or more exposed cells; and c) assessing the epigenetic profile of one or more exposed cells. In one embodiment, said method further comprises step e) using said epigenetic profile for predicting a clinical symptom (or reaction) in a human contacted with said agent. In one embodiment, said assessing said epigenetic profile includes identifying biomarkers related to said exposure to said agent. In one embodiment, said assessing said epigenetic profile includes identifying epigenetic signatures related to said exposure to said agent. In one embodiment, said assessing comprises a determination as to whether said epigenetic signature indicated prior contact with said agent. In one embodiment, said method further comprises step e) comparing said epigenetic profile to another epigenetic profile. In one embodiment, said comparison results are essentially the same. In one embodiment, said comparison results are essentially different. In one embodiment, said comparison of said epigenetic profile was generated under a different experimental condition. In one embodiment, said experimental condition is selected from the group including but not limited to the same cells not contacted with said agent, the same cells contacted with a different agent, the same cells with a different exposure to the same agent and different cells contacted with the same agent. In one embodiment, said different exposure is selected from the group consisting of a different amount of agent, a different duration of exposure, and a different route of exposure. In one embodiment, said different cells are selected from the group including but not limited to a cell derived from a different source, a cell derived from a different time, a cell derived from a different type. In one embodiment, said different route of exposure is an aerosol. In one embodiment, said method further comprises a step after step b) and before step d) of culturing said cells. In one embodiment, said culturing is done under fluid flow. In one embodiment, said microfluidic device further comprises a membrane. In one embodiment, said membrane is coated with extracellular matrix. In one embodiment, said one or more cells are attached to said membrane. In one embodiment, said cell attachment results in formation of a cell layer. In one embodiment, after said cells attach to said membrane said cells are contacted with said agent. In one embodiment, after said cells attach to said membrane said cells are contacted with said agent under flow. In one embodiment, said agent causes a symptom selected from the group including but not limited to death, temporary incapacitation, permanent harm to a human. In one embodiment, said agent is associated with, or a component of an explosive device. In one embodiment, said agent is selected from the group including but not limited to a gas, a liquid, and an aerosol. In one embodiment, said agent is selected from the group including but not limited to pesticides, herbicides, Chloropicrin, Trichloronitromethane and fungicides. In one embodiment, said toxic chemical is selected from the group from the group including but not limited to Sulfur mustards, 2-Chloroethylchloromethylsulfide, Mustard gas: Bis(2-chloroethyl)sulfide, Bis(2-chloroethylthio)methane, O-Alkyl (<=C10, incl. cycloalkyl) alkyl (Me, Et, n-Pr or i-Pr)-phosphonofluoridates, Sarin: O-Isopropyl methylphosphonofluoridate, Soman: O-Pinacolyl methylphosphonofluoridate, Nitrogen mustards: Lewisites, Lewisite 1: 2-Chlorovinyldichloroarsine, and Hydrogen cyanide. In one embodiment, said toxic chemical precursors is selected from the group from the group including but not limited to chlorine, phosgene and hydrogen cyanide (AC), Alkyl (Me, Et, n-Pr or i-Pr) phosphonyldifluorides, DF: Methylphosphonyldifluoride, and Chlorosarin: O-Isopropyl methylphosphonochloridate, Phosphorus oxychloride, Phosphorus trichloride and Dimethyl phosphite. In one embodiment, said chemical weapon is selected from the group from the group including but not limited to choking agents, chlorine, phosgene, blister agents, mustard, lewisite, blood agents, hydrogen cyanide, nerve agents, Tabun, sarin, soman, Cyclosarin and VX. In one embodiment, said toxin is selected from the group from the group including but not limited to Botulinum toxin, Ricin and Saxitoxin. In one embodiment, said radioisotope emits radiation selected from the group from the group including but not limited to alpha particles, beta particles, gamma rays, neutron particles. In one embodiment, said radioisotope is $^{131}$I. In one embodiment, said pathogen is selected from the group from the group including but not limited to bacterial, viral, and fungal. In one embodiment, said pathogen is selected from the group from the group including but not limited to Methicillin-resistant *Staphylococcus aureus* (MRSA), *Burkholderia pseudomallei*, acute viral haemorrhagic illness, Lassa fever virus, HIV, and fungus. In one embodiment, said drug is selected from the group from the group including but not limited to banned drugs. In one embodiment, said method further comprises flowing cells through said device. In one embodiment, said method further comprises flowing fluid through said microchannel and collecting the effluent. In one embodiment, said cells flowing through said microchannel comprise blood cells. In one embodiment, said cells are selected from the group including but not limited to skin cells, gastrointestinal cells, neuro-muscular junction forming cells, nerve cells, and pulmonary (lung-airway) cells. In one embodiment, said pulmonary cells comprise alveolar epithelial cells. In one embodiment, said pulmonary comprise airway epithelial cells. In one embodiment, said cells are derived from a biopsy. In one embodiment, said cells are parenchymal cells. In one embodiment, said cells are obtained from a subject with no prior exposure to said agent. In one embodiment, said assessing said epigenetic signature includes at least one or more assessments selected from the group including but not limited to DNA Methylation, Open Chromatin, RNA Binding Proteins, RNA Expression Profiling, mRNA, chromatin state, histone modification, cfDNA, cfDNA modifications, cellular DNA analysis, mtDNA, circulating no-coding RNA, and chromosomal interactions. In one embodiment, said assessing includes at least one or more detection epigenetic events selected from the group including but not limited to up or down regulation of genes, open vs. condensed chromosome state, histone activation level, methylation, hydroxylation, alkylation, miRNA, noncoding RNA piwiRNA, piRNA and interaction of genomic loci.

In one embodiment, the present invention contemplates a method comprising: a) providing; i) a microfluidic device comprising at least one microfluidic channel comprising attached cells having a phenotype, ii) a plurality of input exosomes suspended in a fluid; and b) flowing said input exosomes into said microfluidic channel; c) incorporating said input exosomes into said attached parenchymal cells; d) releasing a plurality of output exosomes from said attached parenchymal cells; e) flowing said released plurality of output exosomes out of said microfluidic channel; and f) assessing an epigenetic profile of said plurality of output exosomes. In one embodiment, the method further comprises step g) using said epigenetic profile for predicting a change in said phenotype of said cells. In one embodiment, said assessing of said epigenetic profile includes identifying biomarkers. In one embodiment, said assessing of said epigenetic profile includes identifying epigenetic signatures. In one embodiment, said method further comprises step f) comparing said epigenetic profile to a second epigenetic profile. In one embodiment, said first epigenetic profile is obtained from said plurality of input exosomes and where second said epigenetic profile is obtained from said plurality of output exosomes. In one embodiment, said comparison of said epigenetic profile was generated under a different experimental condition. In one embodiment, said input exosomes are derived from a population of cancer cells. In one embodiment, said input exosomes are derived from a population of noncancer cells. In one embodiment, said parenchymal cells are noncancer cells. In one embodiment, said parenchymal cells are cancer cells. In one embodiment, said microfluidic channel further comprises a membrane. In one embodiment, said membrane is coated with extracellular matrix. In one embodiment, said parenchymal cells are attached to said membrane. In one embodiment, said attached parenchymal cells results in formation of a cell layer. In one embodiment, said parenchymal cells are primary cells. In one embodiment, said primary cells are derived from a biopsy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

FIG. 1A We propose to adapt Organs-on-Chips technology (left) as a platform for epigenetics studies incorporating rich biological complexity, an enlargement of a microfluidic chip (right).

FIG. 4A shows an exemplary schematic illustration of two exemplary chemical tags, methyl and acetyl groups involved in epigenetic phenomena and the chemical structure of cytosine and 5-methyl cytosine in DNA are shown. The pentagonal part of the molecule forms the continuous "backbone" of the DNA. One of the two strands of DNA that makes up the familiar double helix is shown.

FIG. 5 shows examples of annotations for labeling epigenetic events discovered using microfluidic devices as described herein, and for use in comparative purposes are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e1001046 (2011). As an exemplary embodiment, TP53 region transcripts detected in nuclear polyadenylated poly A+RNAs isolated from GM12878 vs. K562 cells are shown as an example of comparing epigenetic events between two cell lines. The image shows selected ENCODE and other gene and transcript annotations in the region of the human TP53 gene (region chr17:7,560,001-7,610,000 from the Human February 2009 (GRCh37/hg19) genome assembly). The annotated isoforms of TP53 RNAs listed from the ENCODE Gene Annotations (GENCODE) are shown in the top tracks of the figure, along with annotation of the neighboring WRAP 53 gene. In black are two mRNA transcripts (U58658/AK097045) from GenBank. The bottom two tracks show the structure of the TP53 region transcripts detected in nuclear polyadenylated poly A+RNAs isolated from GM12878 cells and K562 cells. The RNA is characterized by RNA-seq and the RNAs detected are displayed according to the strand of origin (i.e. + and −). Signals are scaled and are present at each of the detected p53 exons. Signals are also evident at the U58658 and AK097045 regions located in the first 10 kb intron of the p53 gene (D17S2179E). The U58658/AK097045 transcripts are reported to be induced during differentiation of myeloid leukemia cells but are seen in both GM12878 and K562 cell lines. The p53 isoform observed in K562 cells has a longer 3'UTR region than the isoform seen in the GM12878 cell line. The ENCODE Project Consortium (2011) A User's Guide to the Encyclopedia of DNA Elements (ENCODE). PLoS Biol 9(4): e1001046, herein incorporated in its entirety.

FIG. 10A shows one exemplary embodiment of making a chip: Replica molding creates stamps with shapes complementary to patterns etched in silicon chips by photolithography. A thin uniform film of a photosensitive material (photoresist) is spin-coated on a silicon chip, which is then overlaid with a photomask (e.g., a transparent glass plate patterned with opaque chrome layers) bearing a microscale pattern generated with computer-assisted design software. The photomask protects some regions of the photoresist and exposes others during exposure to high-intensity ultraviolet (UV) light. The UV-exposed material dissolves in a developer solution, leaving the microscale pattern etched into the photoresist. Elastomeric stamps with a surface topography complementary to the etched surface are created by a replica-molding technique in which liquid prepolymer of PDMS is cast on top of the etched photoresist pattern, polymerized and peeled off. The PDMS stamp can be used for microcontact printing of ECM molecules on any substrate, including those within microfluidic devices.

FIG. 10B shows one exemplary embodiment of a single-channel microfluidic device is fabricated by making a PDMS stamp with two inlets, a single main channel and one outlet and conformally sealing it to a flat glass substrate. A photograph of a two-chamber microfluidic culture device, with different dyes are perfused through upper and lower channels, is shown at the right. The clear side channels are used to apply cyclic suction to rhythmically distort the flexible central membrane and adherent cells.

FIG. 11A-D shows examples of embodiments of organ-on-chip designs.

FIG. 11A shows one exemplary embodiment of a liver-on-a-chip in which hepatic microtissues composed of microscale hydrogels containing hepatocytes and fibroblasts are microengineered in one microfluidic system (top-schematic) and then used to populate another chip for culture and real-time multiplexed analysis (bottom-fluorescently labeled cells).

FIG. 11B shows one exemplary embodiment of a kidney-on-a-chip in which human kidney proximal tubular epithelial cells are cultured on the top of a porous membrane separating two channels, enabling analysis of transcellular transport, uptake and secretion (top-schematic) [73]. The upper fluorescence image of the epithelium shows enhanced formation of primary cilia (green) on the apical cell surfaces; the lower fluorescence cross-sectional view shows repolarization of Na+K+ ATPase (magenta) to the basal side.

FIG. 11C shows one exemplary embodiment of a gut-on-a-chip in which human Caco-2 intestinal epithelial cells are cultured on top of an ECM-coated, porous PDMS membrane separating two channels. Application of cyclic suction to side chambers mimics peristalsis (top-schematic). The phase-contrast micrograph (bottom) shows a large region of the culture with undulating structures reminiscent of intestinal villi; the bottom fluorescence view shows a cross-section of this crenulated epithelial monolayer confirming the presence of crypts (arrow) separating adjacent villi.

FIG. 11D shows one exemplary embodiment of a 'breathing' lung-on-a-chip that recapitulates the alveolar-capillary interface. Human alveolar epithelial cells are cultured on top of a flexible, porous, ECM-coated membrane and human capillary endothelial cells on the bottom. Air is passed through the upper channel to create an air-liquid interface with the alveolar epithelium, and culture medium is flowed through the vascular channel, with or without human immune cells (top-schematic). Breathing motions are mimicked by applying cyclic suction to full-height side chambers that rhythmically distort and relax the flexible PDMS side walls and attached porous membrane. The fluorescence confocal 3D reconstruction at the bottom and the cross-sectional view shown at higher magnification in the inset show the tissue-tissue interface formed between the alveolar epithelium (green) and the endothelium (red).

FIG. 12A-D shows one exemplary embodiment of a Brain-Chip. FIG. 12A Schematic of the chip architecture with two channels. FIG. 12B Neuronal channel with neurons (MAP2), pericytes (NG2), and astrocytes (GFAP). FIG. 12C Brain endothelial cells stained for tight junction marker ZO-1. FIG. 12D Whole channel view of neurons.

FIG. 13 shows one exemplary embodiment of a multi-organ microfluidic framework used for PK/PD modeling. Schematic diagram (top) and photograph (bottom) of a three-chamber chip used for PK modeling by flowing medium through liver, tumor and marrow cells cultured as monolayers in separate chambers and linked fluidically.

FIG. 16A-B shows one exemplary embodiment of a Proximal Tubule Chip. Baseline (top panels) 72 hour (h) EV exposure (i.e. cellular contact with EVs) (lower panels).

FIG. 16A shows exemplary "Healthy" EV exposed kidney tissue.

FIG. 16B shows exemplary "Heart Failure" EV exposed kidney tissue.

FIG. 17A shows an exemplary schematic of a fluidic chip. polydimethylsiloxane (PDMS) (top of chip). Arrow shows directional fluid flow over the top of the parenchymal cells, e.g. kidney cells, attached to a membrane (dotted lines). Dye if perfused through the fluid flowing through the bottom channel lined with endothelial cells over the bottom of the chip (PDMS). FIG. 17B shows exemplary changes in leakage (dye moving into the top channel) in embodiments of a kidney chip perfused with EVs from healthy patients (control) and heart patients (HF) (see, e.g. "type").

FIG. 20 shows an exemplary barrier function as compared to baseline, for one embodiment of a Proximal Tubule Kidney-Chip treated with CRS EV3. P-values: Baseline vs. EV 24 h. 2-way NOVA and Sidak multiple comparison.

FIG. 21A-B shows an exemplary tissue morphology as compared to baseline, for one embodiment of a Proximal Tubule Kidney-Chip treated with CRS EV3. FIG. 21A shows exemplary baseline cells where there is no EV exposed kidney tissue. FIG. 21B shows exemplary CRS EV 3 exposed kidney tissue after 24 h EV exposure.

FIG. 22A shows an exemplary phase contrast image of an Inlet side. FIG. 22B shows an exemplary fluorescent micrograph of endothelial cells (Bottom channel) containing red stained EVs. FIG. 22C shows an exemplary fluorescent micrograph of epithelial cells (Top channel). Scale bar: 100 μm.

DEFINITIONS

Figure 1B:
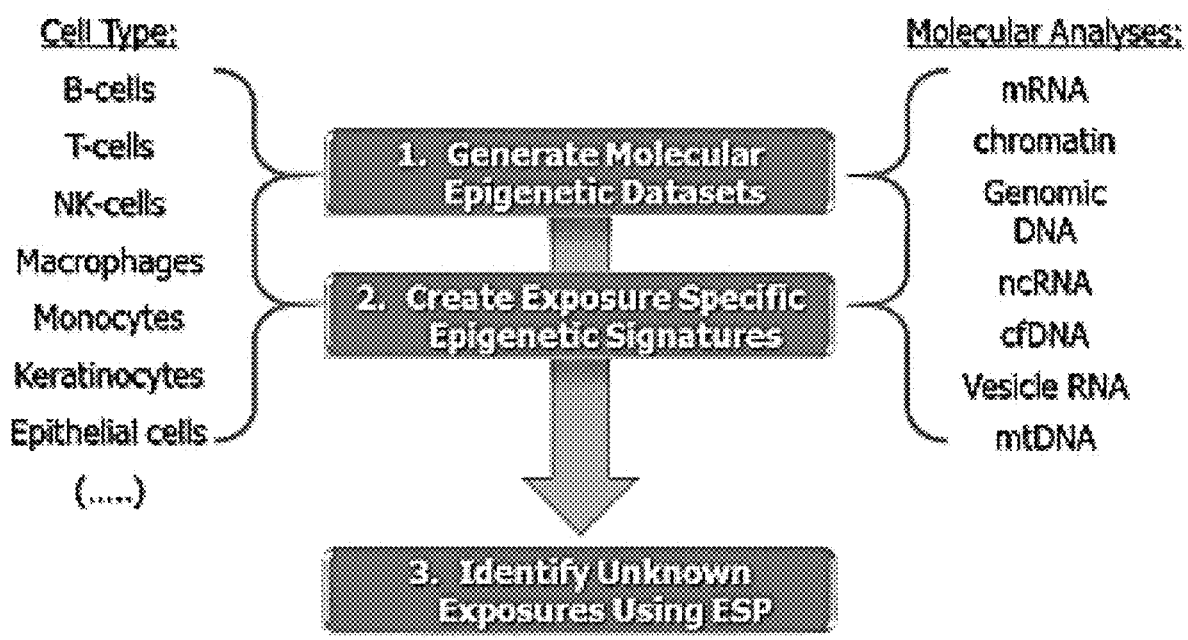
FIG. 1B shows exemplary contemplative pathway to generate signatures, include them in ESP, and perform identification of epigenetic marks (markers or events).

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

Whereas the term "genome" refers to the entire DNA sequence of an organism (e.g. approximately three billion letters (nucleotides) in a human cell), an epigenome refers to the entire pattern of epigenetic modifications in a genome, including but not limited to methyl DNA tags, methyl histone tags, acetyl histone tags and other chemical tags.

"Epigenetic" in general refers to information encoded "on top of" or "in addition to" the traditional genetic basis for inheritance, i.e. typically does not include modifications to the underlying sequence (genetic code). However there are exceptions where the genetic code influences an epigenetic capability, such as DNA methylation, as one example where transfer of a methyl group onto the C5 position of the cytosine to form 5-methylcytosine, thus the DNA sequence without a cytosine at a particular location in the sequence is not capable of methylation at that position. Assessing or determining an epigenetic profile includes detecting changes in the transcriptome and/or genetic code, where such DNA changes may result in a change in the transcriptome. Where an epigenetic profile was determined, this results in an "assessed" epigenetic profile.

"Microphysiology Systems" or "MPS" in general refers to microfluidic devices capable of in vitro emulation of human (or any other animal species') biology.

"Microphysiology Systems" or "MPS" in reference to a military program refers to a program that supports military readiness by enabling timely evaluation of the safety and efficacy of novel medical countermeasures against a wide range of natural and man-made health threats, including emerging infectious disease and chemical or biological attack. The MPS in vitro platform technology is expected to rapidly assess medical countermeasures in a way that is relevant to human health using interlinked "organoid" systems that incorporate engineered human tissue and microfluidics technology into microchips that mimic the functions of human physiological systems.

As used herein, the term "biopsy" refers to a sample of the tissue that is removed from a body.

As used herein, the term "parenchymal cells" refer to functional cells of an organ in the body, such as ciliated epithelial cells and noncilated epithelial cells, keratinocytes, hepatocytes, etc. This is in contrast to the stroma, which refers to the structural tissue of organs, e.g., connective tissues including but not limited to several cell types and extracellular products such as ECM, blood vessels, nerves, ducts, etc. Examples include but are not limited to: parenchyma of the kidney referring to epithelial tissue (including renal tubules and corpuscles) whereas blood vessels, nerves, and supporting connective tissue of the kidney comprise kidney stroma. The parenchyma of the brain is nervous tissue (nerve cells and glia). The blood vessels within the brain and the connective tissue associated with these blood vessels are referred to as stroma. The parenchyma of a malignant neoplasm comprises cancer cells. Other tissues, including blood vessels, which grow to support the tumor, are referred to as stroma.

As used herein, "Caco-2" or "Caco2" refer to a human epithlial intestinal cell line demonstrating a well-differentiated brush border on the apical surface with tight junctions between cells. Although this cell line was originally derived from a large intestine (colon) carcinoma, also called an epithelial colorectal adenocarcinoma, this cell line can express typical small-intestinal microvillus hydrolases and nutrient transporters, see. Meunier, et al., "The human intestinal epithelial cell line Caco-2; pharmacological and pharmacokinetic applications." Cell Biol Toxicol. 11(3-4): 187-94, 1995, abstract. Examples of Caco-2 cell lines include but are not limited to CRL-2102, American Type Culture Collection (Rockville, MD); a BBE subclone of Caco-2 cells; etc.

"Weapons of Mass Destruction" or "WMD" refer to at least one or more of a chemical, biological (e.g. germ weapon), nuclear, radiological (e.g. radioactive) weapon capable of causing death and destruction. Examples include but are not limited to: bacterial, such as the plague, anthrax or Q fever; viruses, including small pox, hepatitis, the avian influenza, and toxins, such as botchalism, ricin, sarin, fungi, toxins, nerve agents, tear gas, vomiting agents, psychiatric compounds or other chemical or biological agents that may be utilized as weapons against humans, animals or the biosphere. Further examples include a radioactive "dirty bomb" or radiological dispersal device (RDD), made by combining radioactive material with explosives to spread it, along with targeted radiation poisoning of a specific person or group of people.

DESCRIPTION OF INVENTION

The present invention relates to microfluidic fluidic devices, methods and systems for use in identifying epigenetic signatures in a range of sample types, e.g., cells established on a "chip" (including but not limited to single cell samples, cell populations, cell layers and whole tissues, such as a biopsy), immune cells, cfDNA, exosomes, and the like. More specifically, in some embodiments, a microfluidic chip containing a sample is contacted with a test compound (e.g. DNA altering test compound, an RNA expression altering test compound, etc.) for use in providing a diagnostic epigenetic signature for that type of sample (or cell type) exposed to that specific test compound. In some embodiments, after contact with a test compound, effluent fluids (e.g. fluids exiting the "chip" that contacted the cells) are derived for testing as a "virtual blood draw." In some embodiments, epigenetic signatures include (but are not limited to) identifying specific combinations of modifications of chromosomes and specific modifications of DNA.

Overview: Organs-on-Chips allow human biology to be accurately emulated in the lab using living human cells. We propose to adapt the technology as a platform for epigenetics studies incorporating a rich biological complexity as an Organs-on-Chips: a Platform for Epigenetics Discovery. System will be designed to identify epigenetic signatures in various sample types, e.g., immune cells, cfDNA, and biopsy. We plan to integrate the deep biological insight that Organ-on-Chips offer with partners' clinical and WMD expertise.

Overview and Objectives: The Emulate team is world leading in the development and use of Organ-Chip systems, including associated analytics and omics (e.g. genomics, proteomics, transcriptomics, etc.). Technology has been proven predictive of the human body and has been successfully employed to identify potential biomarkers. Commercialized Chip and instrument platform provides high-quality data and enables sufficient throughput. Seeking partners with access to suitable clinical samples, WMD expertise, and point-of-care diagnostics development.

Impact: Success will yield a platform for epigenetic signature discovery broadly useful for developing new diagnostics and forensics across civilian and defense needs. As a high-content approach able to incorporate many cell types, the platform should allow discovery of signatures across different analytic methods and sample types. Commercialization strategy and user-centric design will ensure that developed technology will maximize impact in government and commercial arenas.

In general, a microfluidic epigenetic signature on-chip will be used to discover an epigenetic signature associated with a particular test compound (agent), such as a group of chromosomal (including nucleotide) biomarkers (epigenetic events) or pattern of chromosomal biomarkers. In one embodiment, a pattern of biomarkers may be where certain types of epigenetic tags associate with an epigenetic signature. In one embodiment, a pattern of biomarkers may be where actual epigenetic tags associate with an epigenetic signature. In one embodiment, such signatures are contemplated to be associated with a group of cell types. In one embodiment, such signatures are contemplated to be associated with a particular cell type. In one embodiment, such signatures are contemplated to be associated with a tissue. In one embodiment, such signatures are contemplated to be associated with a cfDNA released from cells into fluids. In one embodiment, such signatures are contemplated to be associated with exosomes released from cells into fluids. In one embodiment, such epigenetic signatures (also termed "epigenetic profiles") are contemplated to be associated with a particular pattern of RNA expression profiling.

These chips will provide a model for studying epigenetics, such as providing a model for demonstrating specific changes or patterns of changes in nucleic acid sequences that are not related to the actual sequence, i.e. not related to an allelic change per se, but related to contact with a compound through induced topographical alterations of DNA nucleotides and chromosomal material. Such contact may induce an immediate change or a change induced during or after replication of a chromosome. In other words, epigenetic signature chips would provide an epigenetic signature that associates with a particular variable, e.g. epithelial cells on-chips treated with a compound whose induced epigenetic pattern associates with skin cells obtained from a patient in contact with that same compound. In one embodiment, a databank, e.g. panel, of base-line epigenetic signatures in combination with an epigenetic signature on-chip for a patient's sample would allow "reading" a patient's epigenetics in order to determine what compound or condition they may have been exposed to (e.g. a type of forensics/diagnostics).

Embodiments include methods for seeding microfluidic chips with a sample, such as seeding keratinocytes obtained from one source, in numerous duplicate open top chips, then challenging the chip with a test compound, e.g. by contacting with an agent; drug, chemical weapon, radiation, infection with a biopathogen, i.e. bacterial, viral, fungal; etc., Such contacting may be by using either a single concentration or one specific dilution or a dilution series tested on a group of duplicate chips under flow during incubation, either during or after contacting. In some embodiments, a blood sample would be flowed over contacted cells in said chip. In some embodiments, a white blood cell sample would be flowed over contacted cells in said chip.

After which, efferent fluid would be sampled at certain time points for collecting epigenetic signature samples, in some embodiments. In some embodiments, blood cells from a blood sample flowed through the chip would be collected for epigenetic analysis.

In other embodiments, cells would be lysed within the microchannel then flushed into the effluent tubing for collection for further processing, such as for chromosome isolation, DNA isolation in a spin column, RNA isolation by cesium chloride centrifugation, etc.

Isolated sample material would then be used to assess the epigenetic profile of one or more cell type involved in the chip, including but not limited to cells located within the chip, cells attached to the chip, cells flowing through the chip, e.g. blood cells, nucleic acids released by cells that were flowed over or in contact with treated cells.

In some embodiments, epigenetic profiles obtained from one experimental condition would then be compared to the same experimental condition for identifying associative epigenetic patterns. In some embodiments, epigenetic profiles obtained from one experimental condition would then be compared to another experimental condition, e.g. a chip that was not exposed to the same challenge (e.g. a negative control lacking a variable, such as an exposure to an agent, or not receiving input exosomes), or a chip that was exposed to a different challenge (e.g. for comparing an epigenetic response between exposure to two different viral strains). The idea is that this could allow us to identify epigenetic signatures (i.e. essentially biomarker discovery), as well as to validate them.

It is contemplated that samples used as base-line samples in microfluidic chips would provide epigenetic information that might be used in numerous applications, including but not limited to military and civilian applications, including monitoring for past or current exposure to one or more types of agents associated with Weapons of Mass Destruction (WMD); exposure to pathogens; exposure to drugs, clinical diagnostics, drug discovery, and the like.

I. Applications Using Base-Line Epigenetic Information.

Microfluidic devices are contemplated for use in a variety of types of epigenetic information further contemplated for discovery and use. In some embodiments, base-line epigenetic information will be generated for use as a base-line epigenetic signature for a particular type of test agent or test treatment on a particular sample, such as a cell type, tissue, organ, blood cell, etc. In some embodiments, side-by-side samples may be used for providing comparative epigenetic information for generating epigenetic signatures. Samples may be contained within one device or fluidically linked devices. In some embodiments, base-line epigenetic signatures may be stored in a database and used in procedures for identifying past and current exposure to known or unknown compounds.

The present invention also provides an integrated device to achieve: 1) Epigenetic molecular analysis integration; and 2) Onboard computational and bio-analytical capability. In some embodiments, such a device is for storing information on microfluidic devices, samples, cells, compounds, treatments, epigenetic assays, epigenetic results, epigenetic signatures, etc., browser interfaces, internet connectivity, wireless access, computation software for epigenetic analysis, generating epigenetic signatures, generating specific reference panels associated with specific types of exposes, onboard computational and bio-analytical capability, etc. In some embodiments, such a device is a hand-held device.

In some embodiments, a storage device is not connected to the internet, such as a backup storage device, a device containing information deemed not publicly available via the internet, etc. In some embodiments, such use of base-line epigenetic signatures includes setting up desired panels of base-line epigenetic signatures, depending upon need. As one non-limiting example, a panel of base-line epigenetic signatures comprises epigenetic signatures obtained from the same or similar microfluidic devices treated with a particular agent for comparing to epigenetic signatures obtained from the same or similar microfluidic devices comprising samples obtained from an individual or group of individuals suspected or known to have been exposed to the same or similar agent. After comparing the test sample's signature with a panel of base-line epigenetic signatures, or directly with the entire group of epigenetic signatures in a database, a determination would be made as to whether the epigenetic signature indicated exposure to a particular agent or similar agent. In some embodiments, the epigenetic signature comparison may indicate approximately when the exposure occurred, the duration of the exposure, etc.

As nonlimiting examples, test agents may include chemicals, such as pesticides, herbicides, fungicides, pathogens, toxins, radionuclides in the environment, ionizing radiation (e.g. alpha particles, beta particles, gamma rays, neutron particles), thermal blast effects, thermal radiation, electromagnetic pulse, direct nuclear radiation, radioactive material fallout, biowarfare agents, see below, etc. As nonlimiting examples, test agents may include chemicals related to explosive compounds, precursors to explosive compounds, residues related to explosive compounds, explosive devices, etc., including but not limited to nitrogenous compounds, gunpowder, etc.

A. Weapons of Mass Destruction (WMD).

Current forensic practice use residues associated with Weapons of Mass Destruction (WMD) manufacture or exposure, which are often transient and in such low concentrations making them virtually undetectable in field forward austere conditions. Therefore, one contemplated use of an epigenetic signature obtained from microfluidic samples on-chips is to determine an individual's WMD and WMD precursor exposure history, recorded in their own epigenome. Thus, compositions and methods described herein, using a microfluidic chip and a sample, provides an advantage over current methods, as the epigenome is imprinted in the genome of an organism would be detectable even when physical evidence has been erased, i.e. through cleaning surfaces, such as skin, clothing, etc., or decayed, decomposed, etc., over time.

Thus, a pattern of unique epigenetic changes, i.e. signature, would be found to associate with a specific exposure to a single compound or agent. The exposure-specific epigenetic signatures will contain information that denotes the specific exposure and time since exposure. An epigenetic signature panel into a point-of-need forensic and diagnostic system. Forensically link an individual to WMD manufacture, and diagnose WMD exposure, with high specificity and temporal resolution with respect to the timing of the exposure event.

In some embodiments, epigenetic signatures from WMD exposure events are characterized, and new bioinformatics tools to perform forensic analysis and disease diagnostics with high sensitivity, specificity and temporal resolution would be developed using such epigenetic information. In a preferred embodiment, there is a low variability between associated epigenetic signatures obtained from similar or duplicate base-line samples in microfluidic chips.

In some embodiments, microfluidic devices are untreated. In some embodiments, microfluidic devices are treated with the same amount of test compound (or same amount of radionuclide, or exposed to the same amount and type of radiation for the same duration of time) on the same cell samples for determining repeatability of epigenetic alterations. In some embodiments, microfluidic devices are treated with dilution series, a group of related compounds, unrelated compounds, a range of radiation doses, etc., for comparisons. Thus an epigenetic signature on-chip may be used for identifying epigenetic changes in a specific type of sample exposed (or not) to a specific compound or treatment, over a specific duration of time, in order to provide a repeatable base-line epigenetic signature for a particular test compound. Such a base-line epigenetic signature may be incorporated into a databank for use in an epigenetic signature databank or used in a subset of information as a reference panel. Such an epigenetic signature databank (or selected panel of base-line agents) is contemplated for use when comparing an epigenetic signature obtained from a test sample for identifying the closest known (i.e. generated by methods described herein) epigenetic signature matching the base-line sample.

In one embodiment, an epigenetic signature on-chip is considered a virtual blood draw. Thus, for one example of a virtual blood draw fluids are flushed through a microfluidic chip comprising a cell sample, wherein said cells were treated with a test compound. Fluids exiting a microfluidic chip as effluent would be used for monitoring an epigenetic change in DNA within the fluid, such as epigenetic changes in cell free DNA, cfDNA, enzymes or epigenetically altered nucleotides within an exosome, etc.

An epigenetic signature on-chip would allow observation of responses of cells to a test compound. Such cells would include different types, including but not limited to epidermal cells (e.g. a combined population in an epidermal layer), endothelial cells, a comparison of cells within the same population, such as ciliated vs. nonciliated epidermal cells.

Epigenetic signatures obtained from samples on-chip, would be used to generate epigenetic signatures in human cells (samples). Then this signature would be used later on for comparing to other epigenetic signatures obtained from test human cells (samples) in order to determine whether that human was exposed to a particular chemical. Exposure to a chemical not typically found in the environment would indicate that the chemical was deliberately or accidentally released into the environment. As such, exposure to non-typical chemicals, or agents, might indicate activity with that chemical that would be considered dangerous to others, in particular when normal or adverse weather events or patterns, such as wind patterns, currents, etc., would make it more difficult to detect release or presence of chemicals (or pathogens, radioisotopes, radiation contamination, etc.).

Exposure to environmental factors is expected to change epigenetic features. Depending upon the exposure type, the epigenetic features can change within minutes, while also leaving a lasting 'mark' on the epigenome for decades. As described herein, a results from controlled exposures, thus low variability, will be used to generate (build) signatures that incorporate a detected pattern of unique epigenetic changes associated with a specific exposure to a single compound or agent (also referred to as "exposure-specific"). The exposure-specific signatures will contain information that denotes the specific exposure (i.e. type of pathogen, type of compound, etc.) and time since exposure.

The following is merely an example of a method for using microfluidic devices and samples for inducing epigenetic events for use in generating epigenetic signatures.
1) Generate molecular epigenetic datasets associated with relevant WMD and/or precursor exposure.
2) Characterize and define exposure-specific epigenetic signatures.
3) Identify unknown exposures using a reference epigenetic signature panel, including but not limited to a panel generated as described herein, comprising information that would be useful in aiding the identification of an unknown exposure, a suspected exposure to a particular compound or pathogen vs. chemical vs. radiation, integrated as a point-of-need forensic and diagnostic system. In additional embodiments, a reference epigenetic signature panel may include but is not limited to additional data, including additional epigenetic data, such as found in an Epigenetic Characterization and Observation (ECHO) Signature Panel—ESP). An ESP is contemplated to consist of a collection of identified exposure-specific signatures within an ECHO program, also integrated as a point-of-need forensic and diagnostic system.

The following are nonlimiting examples of types of exposures, i.e. treatments that may find use with microfluidic devices described herein for use with obtaining information on epigenetic biomarkers and generating epigenetic signatures.

TABLE 1

Classification of exposures (e.g. agents, test compounds, etc.) that may find use in testing samples in microfluidic devices for generating epigenetic signatures from detected (or absent) epigenetic events.

| Exposure Category | Exposure Sub-category | Minimum Required List of Exposure-Specific Agents/Compounds |
|---|---|---|
| Biological | 1. Bacterial agents* | *Staphylococcus aureus* (MRSA) *Burkholderia pseudomallei* (2 total) |
| | 2. Viral agents*: | Human immunodeficiency virus (HIV) Lassa fever virus (2 total) |
| | 3. Other emerging infectious diseases | Proposers may select exposure-specific samples from any of the additional exposure categories. |
| Chemical | 4. Chemical agent precursors* | |
| | 5. Conventional agents[1.] | Teams are strongly encouraged to address militarily relevant compounds, precursors*, or agents from each of the 10 sub-categories (17 total) |
| | 6. Toxic industrial compounds | |
| Radiological | 7. Medical isotopes | |
| | 8. Isotopes associated with weapons production | |
| Explosives | 9. Explosives precursors | |
| | 10. Explosives compounds* | |

*https://www.selectagents.gov/selectagentsandtoxinslist.html, of which these agents that may find use with microfluidic devices as described herein, are incorporated by reference in their entirety.
‡ Precursors in schedules 1, 2, 3 of The Organization for Prohibition of Chemical Weapons (OPCW) Chemical Weapons Convention (CWC) list: https://www.opcw.org/chemical-weapons-convention/annexes/annex-on-chemicals/schedule-1/, of which these agents that may find use with microfluidic devices as described herein, are incorporated by reference in their entirety.
† Agents listed in schedules 1, 2, 3, of the OPCW CWC list: https://www.opcw.org/chemical-weapons-convention/annexes/annex-on-chemicals/schedule-1/, of which these agents that may find use with microfluidic devices as described herein, are incorporated by reference in their entirety.
https://www.atf.gov/file/97721/download: Federal Register/Vol. 79, No. 194/Tuesday, Oct. 7, 2014/Notices (Notice of the 2014 Annual List of Explosive Materials, of which these agents that may find use with microfluidic devices as described herein, are incorporated by reference in their entirety.

Precursor chemicals, agents, etc., (such as those compounds used for producing components of an atomic bomb, explosives, altering a pathogen (including but not limited to producing a weaponized pathogen) nerve gas, components used for synthesizing nerve gas, components used for synthesizing other types of weaponized or toxic chemicals, etc.) would be selected for testing. In some embodiments, selection may be based on their association with a production process for making a specific chosen agent.

When a particular agent is not available for use in providing an epigenetic signature, an agent deemed to be representative of that type of or class of agent may be used for providing a comparative epigenetic signature.

In some embodiments, a side-by-side experiment is contemplated comparing a microfluidic device comprising a cell sample derived from a person having an exposure to a particular unknown agent to a microfluidic device comprising a cell sample treated with agents suspected of being the unknown agent or associated with the unknown agent in order to identify the agent or class of agent. In some embodiments, a side-by-side experiment is contemplated comparing a microfluidic device comprising a cell sample derived from a person suspected of exposure to a known agent to a microfluidic device comprising a cell sample treated with the known agent or agents associated with that agent, such as precursor compounds, in order to determine whether the person was in contact with that agent. In some embodiments, epigenetic signatures in a database or selected from a database are used for comparisons when identifying an unknown exposure agent or determining the possibility of exposure to a particular agent.

Exemplary sample types include but are not limited to: biopsies, cell scrapings, skin cells, buccal swabs, swabs of other cell surfaces that may contain residual cells, genetic material, etc., blood, discharges, e.g. nasal mucus, sputum, tears, urine, feces, etc.; obtained from bodily areas including, buccal areas, nasal passages, lung, skin, hair (follicles), cells from nail beds, etc. Cell types include, but are not limited to white blood cells, such as T-cells, B-cells, etc.; skin cells, e.g. keratinocytes, melanocytes, nerve cells, adipose cells, fibroblasts, dermal cells, etc.; linings of openings, e.g. epithelial cells, nasal cells, airway cells, buccal cells, etc.

B. Characterize and Define Exposure-Specific Epigenetic Signatures.

A brief method for field testing includes but is not limited to collecting samples as described herein, extracting material for epigenetic analysis from samples, isolating nucleic acid and preparing it for epigenetic analysis; perform multiple epigenetic analyses via sequencing or other molecular analyses; compare results to concurrent epigenetic analyses of sample controls, and/or compared to a panel of chosen epigenetic signatures derived from a data bank of epigenetic signatures. In some embodiments, results from field samples may be compared to selected subsets or the entire databank of epigenetic signatures. In some embodiments, a field device may be a microfluidic device as described herein. A combination of molecular methods may be used to reveal epigenetic events (marks). Epigenetic marks (events) to consider incorporating into an epigenetic signature, include, but are not limited to, gene expression profiles, chromatin access/state, histone modifications, regulatory marks on cellular or cell-free DNA (cfDNA), circulating non-coding RNA, and cellular or circulating mitochondrial DNA (mtDNA). Additional types of epigenetic events and methods are described or referred to herein for generating epigenetic signatures, including those shown in Table 2.

TABLE 2

Exemplary epigenetic events and molecular methods.

| Example Epigenetic | Example Method(s) | Event(s) |
|---|---|---|
| Example Epigenetic | | RNA-SEQ SONO-SEQ, ATAC-SEQ, DNase-SEQ, FAIRE-SEQ, MNase-SEQ |
| Target mRNA | Up or down regulation | |
| Chromatin State | Open, condensed | |
| Histone Modifications | Activating, poised for activation, or repressing: For example, H3K4me2/3, H3K27me3 | ChIP-SEQ, MINT-ChIP |
| Cellular or Circulating DNA (cfDNA) Modifications | Methylation, hydroxylation, or alkyklation: 5-mC, 5-hMC, 5-fC, 5-caC, and 3-mC | Meth-SEQ, WGBS, TAB-SEQ |
| Cellular or Circulating Mitochondrial DNA (mtDNA) | Methylation | Meth-SEQ |
| Circulating Non-coding RNA | MicroRNA (miRNA), long non-coding RNAs (lncRNAs), and piwiRNAs (piRNA) | RNA-SEQ, ChIRP-SEQ |
| Chromosomal Interactions | Interaction of Genomic Loci | Hi-C, 3C, 4C, 5C, ChIA-PET |

B. Radiation Exposure.

Meteorology often determines where the offsite release (the radioactive plume or any other type of biowarfare agent or exposure, such as an aerosolized chemical, aerosolized toxin, aerosolized pathogen, and the like) goes, and determines the concentration of the radionuclides (or other agents) to which the downwind public is then exposed. Meteorological information includes wind speed, direction, persistence and variability, and vertical dispersion. Those factors describe the stability of the atmosphere and indicate how fast, far and wide radionuclides (or any other type of biowarfare agent or exposure) would be transported in air. Under very stable atmospheric conditions, there is little dispersion of the plume and the radionuclide (or other agents) concentration is much greater than under very unstable atmospheric conditions that would disperse the plume and lower radionuclide (or other agents) concentrations in it. Stable conditions (unfavorable meteorology) are usually chosen for performing Design Basic Accident (DBA) calculations, rather than the prevailing meteorological conditions.

For example, under normal meteorological conditions, the plume from a release site moves away from the release point much as smoke moves away from a chimney. Those in the direct path of the plume would be in immediate danger. Just as smoke dissipates as it moves away from a source, so does a radioactive plume. This dissipation quickly decreases the concentration of radioactive materials within the plume. If the quantities of radionuclides (or other agents) in the plume have public-health significance for people in the path of the plume, such protective actions as sheltering (remaining indoors) and evacuation would be considered. Weather conditions that might prevent immediate evacuation, such as blizzards or torrential rainfalls, would remove radioactivity (or other agent) from the plume close to the point of release and actually help to protect people who are downwind. However then the agent dissolved in water or part of the moisture in the air, might directly contact people with indirect contact from contaminated ground water, etc. During the plume phase of a reactor-accident release, the thyroid might be exposed externally to gamma radiation from radionuclides (or other agents) in the plume or it might be exposed internally if radioiodine (or other agents) is present and inhaled. In relation to radiation, thyroids of mammals can also be exposed internally through the intake of radioiodine by the consumption of contaminated milk, water or foods, such as leafy vegetables. Consideration of the ingestion of milk is particularly of concern because radioiodine deposited on pasture grass is reconcentrated in the milk of grazing animals (particularly cows, goats, sheep and reindeer).

Radioactive fission products are typically gasses (such as the radioactive noble gasses of xenon and krypton), particulates (such as strontium) or volatile (can be readily evaporated) materials, such as radioiodine. Radioactive noble gasses are, in general, not considered an ongoing threat to public health because they do not stay in the body when breathed in and they do not concentrate in the environment. Radioiodine is of particular concern because of the ease with which it can convert to a vapor state and because radioiodine taken into the body will concentrate in the thyroid gland if the thyroid is not saturated with prophylactic administration nonradioactive iodine before the radioiodine reaches it. Radioiodine is one of many radionuclides present in nuclear fuel or released when an atomic bomb detonates. Radioiodine can exist in particulate form, such as cesium iodide (Cs $^{131}$I) or sodium iodide (Na $^{131}$I), as a radioiodine vapor, or as a solution with the radioiodine dissolved in water. In the environment, the different physical and chemical states of radioiodine provide several pathways for it to reach humans. Thus, further examples include determining epigenetic signatures of samples that were exposed (by air or water or ingestion) to radioiodine for determining a person's or group of people's exposure, either unintentionally or intentionally.

Radioiodine in the gaseous state can be inhaled into the lungs where it can dissolve and enter the blood. The blood then circulates through the body, including the thyroid gland. Under the condition of normal nutritional iodine supply, a normally functioning thyroid gland will take up and store between 15-30% of the iodine to which it is exposed, whether it is radioiodine or the chemically identical nonradioactive iodine (the thyroid does not recognize any difference between radioactive and nonradioactive iodine). Studies have shown that about 55% of radioiodine breathed in is absorbed into the blood in the lungs and transported throughout the body (Costa et al., 1982).

Although, as one example, the inhalation-exposure route was not a major contributor to the thyroid doses of the populations exposed to radioiodine released in the Chornobyl accident; rather, it was estimated that most of the radioiodine taken into the thyroid entered the body in contaminated food or drink (e.g. water). Thus, in some embodiments, microfluidic devices used for generating epigenetic signatures may be for generating base-line comparisons from human gastrointestinal chips, mammalian epithelial cells, e.g. human epithelial cells, mammary epithelial cells, mammary epithelial cells of ruminants, might find use in monitoring for the presence of nuclear materials.

Radioiodine in some cases is also byproduct of the fission of uranium atom from nuclear plant discharges, nuclear-powered submarines, use as an explosive material in atomic bombs, etc., in addition a radioisotope for uses in medical diagnosis and therapy, in particular using a microfluidic chip comprising epithelial, thyroid cells, thyroid tissue, including but not limited to clinical biopsies. As one nonlimiting example, radioactive iodine ($^{131}$I) has a short half-life (8 days) so identifying a person with suspected or prior exposure, long after radioactive iodine ($^{131}$I) or decay products can be detected in or on that person, is contemplated for use with epigenetic devices and methods. For example, determining an epigenetic signature obtained from microfluidic devices comprising cells, blood, or extracellular cfDNA, exosomes, etc. of base-line or comparative (reference) epigenetic signatures would be compared to epigenetic signatures obtained using microfluidic devices comprising cells, tissues, or fluids derived from the person suspected of exposure or known exposure is contemplated for determining any one or more variable such as time after exposure, duration of exposure, amount of exposure, amount of and type of damage to cells, tissues, organs, etc. Such determinations would allow the determination of whether a person was exposed to an isotope, and then if a person was determined to have been exposed, allow the prediction of risk for developing a disease related to that exposure; for use in clinical management of that person, for determining the risk of whether other people were exposed, for taking measures to reduce or stop exposure, etc.

Moreover, because radioisotopes of specific amounts, specified duration of exposure, and exposures (treatment) at known dates, such as for radioactive iodine, are routinely part of clinical diagnostics and treatments, e.g. for treating overactive thyroids, such patients may be used for obtaining. epigenetic signatures associated with radioisotopes that have reduced outside variables. Such that in one embodiment, untreated patients having untreated cells, tissues, blood, etc. as samples used in microfluidic chips, may be used for obtaining baseline epigenetic signatures for comparison to patients treated with a radioactive isotope, such as Iodine radioisotopes for patients having overactive thyroids, for obtaining epigenetic signatures specifically associated with amounts of isotopes, duration of treatment, with samples collected at specific time points after treatment. Such samples would include but are not limited to thyroid, gastrointestinal, bladder, lung etc. Examples of medical procedures performed are with a few thousandths of a curie (several millicuries) to a few tenths of a curie (several hundred millicuries) of $^{131}I$, thus microfluidic devices would be exposed to $^{131}I$ within this range or scaled to an equivalent range depending upon the goal of the exposure.

II. Epigenome and Epigenetics.

An "epigenome" refers to the chemical changes to the DNA and histone proteins of an organism. Epigenetics refers to the study of characteristics or "phenotypes" of cells, tissues or organisms that do not involve changes to the particular nucleotide, with the exception of DNA sequence changes (mutations or differences in alleles) that provide or remove an opportunity to have an epigenetic event at that particular location in the sequence or chromosomal area. Epigenetics is also a term used to describe inheritance of traits by mechanisms other than through the DNA sequence of genes. In part, epigenetic events occur to modify the topology of a DNA chromosomal sequence by adding and removing small chemical tags to DNA (nucleotides within a DNA sequence). One of the chemical tags is a methyl group (see FIG. 4A) and it is used to modify one of the four bases or "chemical letters", A, C, T and G, that makes up the genetic code of our DNA. The letter that is tagged is C or cytosine and when it is modified, or methylated it is called 5-methyl cytosine. Methyl groups are added to DNA by enzymes called DNA methyl transferases (DNMTs).

DNA methyl tags are one part of the story. Epigenetic tags are not limited to DNA or DNA based chromosomal areas, such that an epigenetic tag may also be attached to a protein involved with histones. Histones are proteins used for coiling DNA sequences within a chromosome, see FIGS. 4A-C.

Figure 4B:
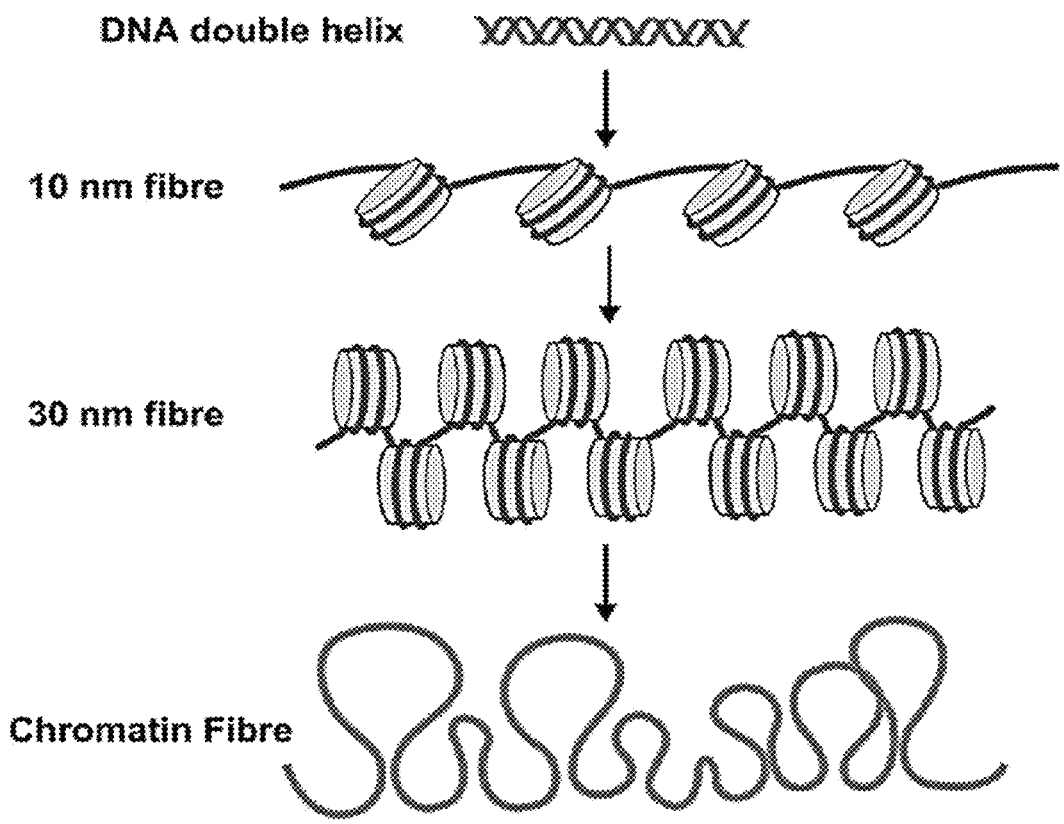
FIG. 4B shows an exemplary DNA double helix (black) is wrapped around nucleosomes (grey cylinders) in cells. The string of nucleosomes can be coiled into a thicker filament, called 30 rim fibers and this can be further coiled into a still thicker chromatin fiber. When genes are switched on their nucleosomes are more uncoiled like the 10 nm fiber.
Figure 4C:
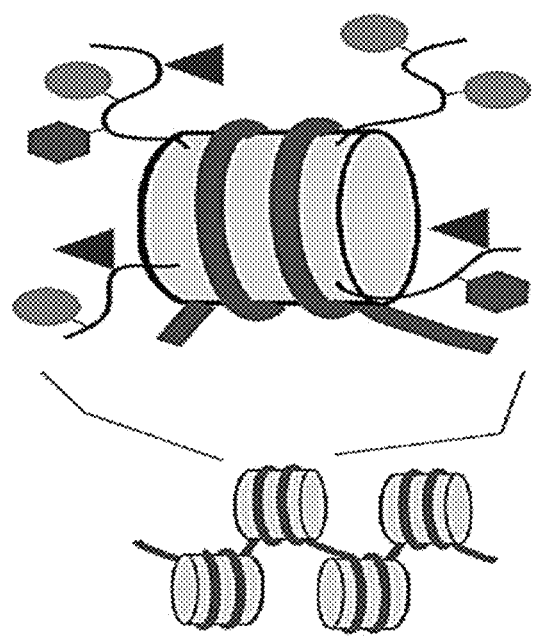
FIG. 4C shows an exemplary chemical tags can be added to the "tails" of the histone proteins that make up nucleosomes. Grey cylinder, nucleosome; curved black lines, histone tails; circles, methyl tags; triangles, acetyl tags; hexagons, other types of tags.
Figure 6:
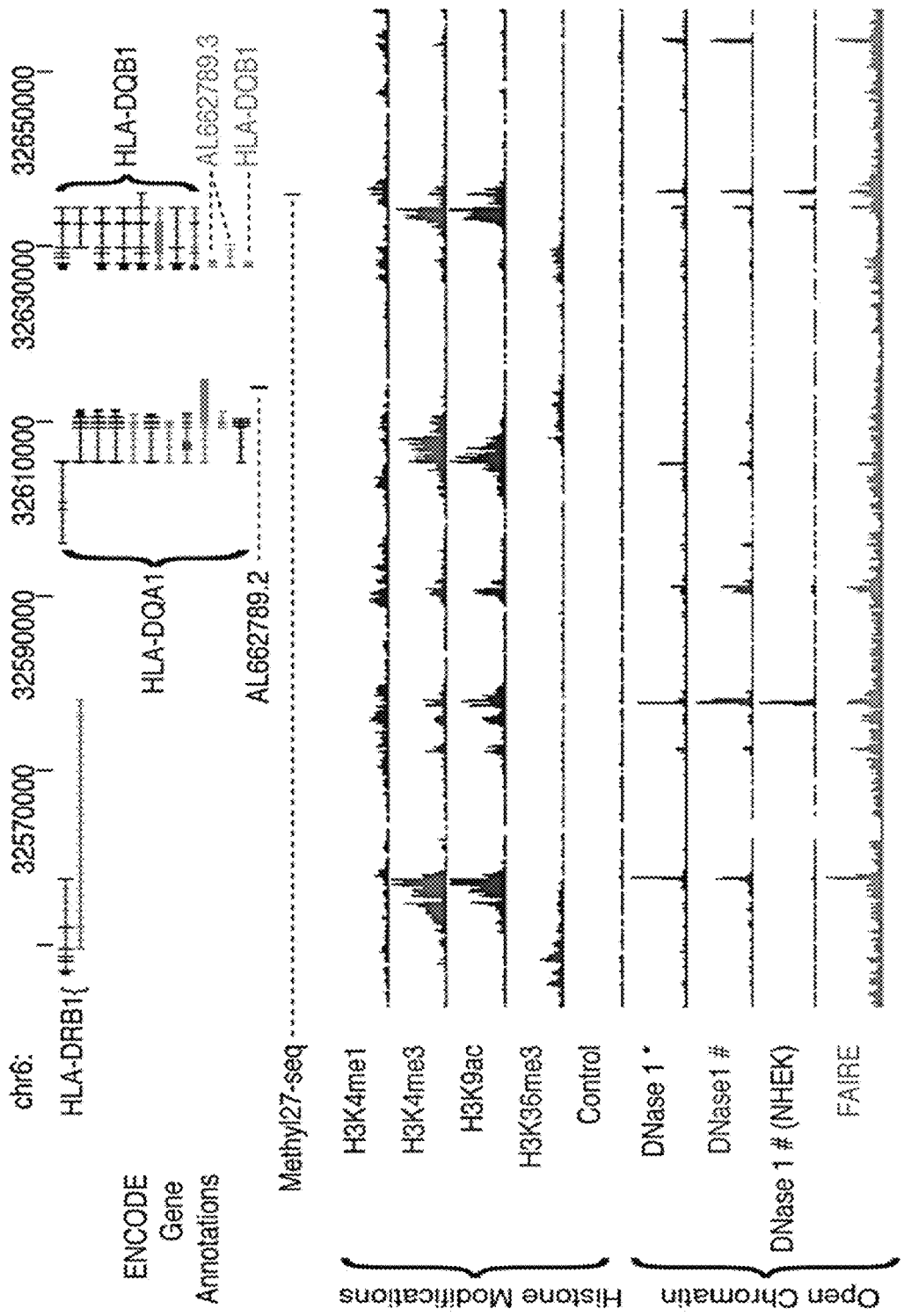
FIG. 6 shows examples of partially methylated genes, densities of four histone modifications associated with transcriptionally active loci, accessibility of DNA in chromatin to nucleases (DNaseI) and reduced coverage by nucleosomes, and comparative DNaseI sensitivity between different cell lines are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e 1 001046 (2011). As exemplary embodiments: ENCODE chromatin annotations in the HLA locus. Chromatin features in a human lymphoblastoid cell line, GM12878, are displayed for a 114 kb region in the HLA locus. The top track shows the structures of the annotated isoforms of the HLA-DRB1, HLA-DQA1, and HLA-DQB1 genes from the ENCODE Gene Annotations (GENCODE), revealing complex patterns of alternative splicing and several non-protein-coding transcripts overlapping the protein-coding transcripts. The next line shows that a CpG in the promoter of the HLA-DQB1 gene is partially methylated (assayed on the Illumina Methylation27 BeadArray platform). The densities of four histone modifications associated with transcriptionally active loci are plotted next, along with the input control signal (generated by sequencing an aliquot of the sheared chromatin for which no immunoprecipitation was performed). The last lines plot the accessibility of DNA in chromatin to nucleases (DNaseI) and reduced coverage by nucleosomes (FAIRE); peaks on these lines are DNaseI hypersensitive sites. Note that the ENCODE Consortium generates DNaseI accessibility data by two alternative protocols marked by * and #. The track shows DNaseI sensitivity in a different cell line, NHEK, for comparison. The ENCODE Project Consortium (2011) A User's Guide to the Encyclopedia of DNA Elements (ENCODE). PLoS Biol 9(4): e1001046, herein incorporated in its entirety.
Figure 7:
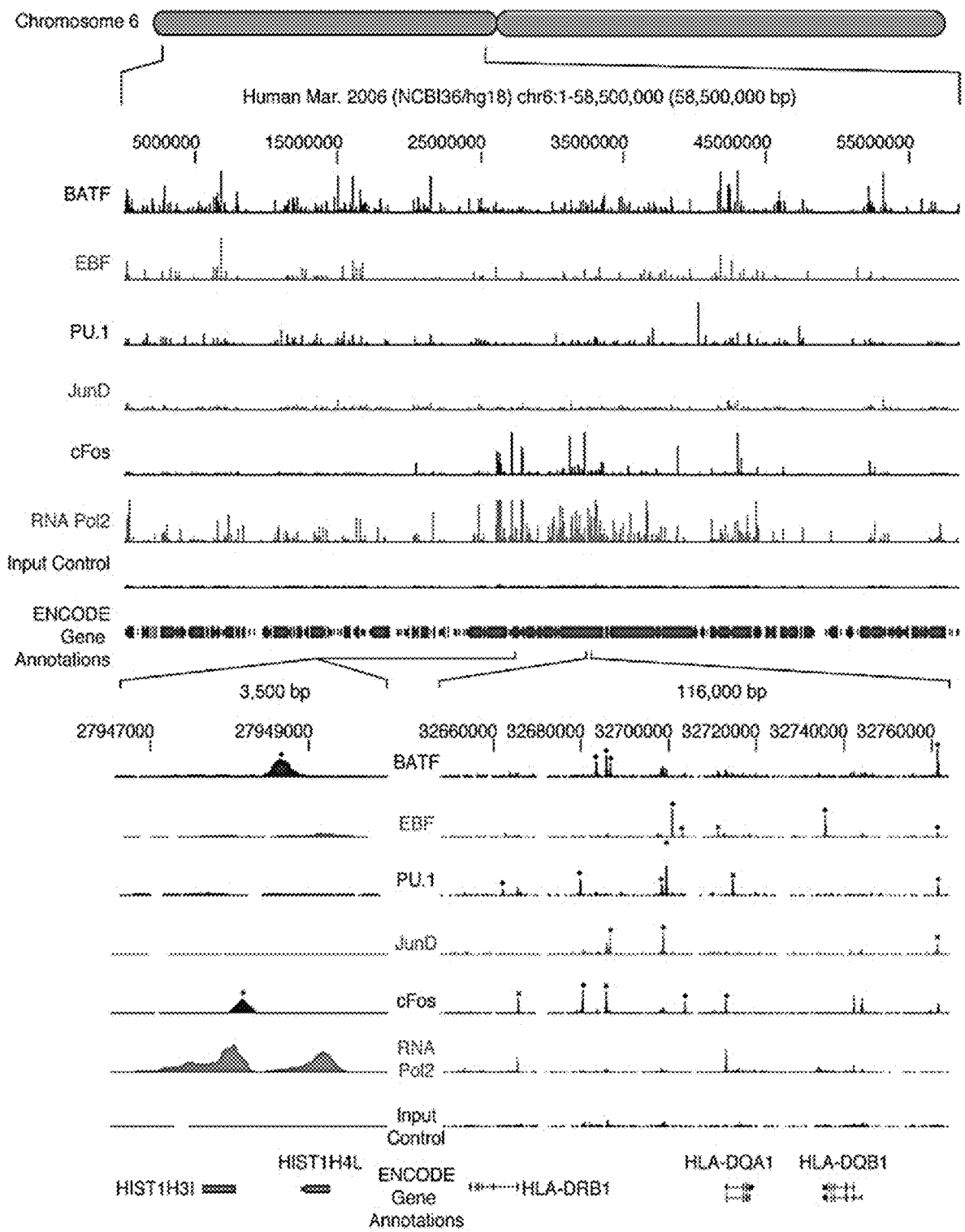
FIG. 7 shows examples of occupancy of transcription factors and RNA polymerase 2 on human chromosome 6p as determined by ChIP-seq are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e1001046 (2011). As exemplary embodiments: The upper portion shows the ChIP-seq signal of five sequence-specific transcription factors and RNA Pol2 throughout the 58.5 Mb of the short arm of human chromosome 6 of the human lymphoblastoid cell line GM12878. Input control signal is shown below the RNA Poll data. At this level of resolution, the sites of strongest signal appear as vertical spikes in next to the name of each experiment ("BATF," "EBF," etc.). More detail can be seen in the bottom right portion, where a 116 kb segment of the HLA region is expanded; here, individual sites of occupancy can be seen mapping to specific regions of the three HLA genes shown at the bottom, with asterisks indicating binding sites called by peak calling software. Finally, the lower left region shows a 3,500 bp region around two tandem histone genes, with RNA Pol2 occupancy at both promoters and two of the five transcription factors, BATF and cFos, occupying sites nearby. Selected annotations from the ENCODE Gene Annotations are shown in each case. The ENCODE Project Consortium (2011) A User's Guide to the Encyclopedia of DNA Elements (ENCODE). PLoS Biol 9(4): e1001046, herein incorporated in its entirety.
Figure 8A:
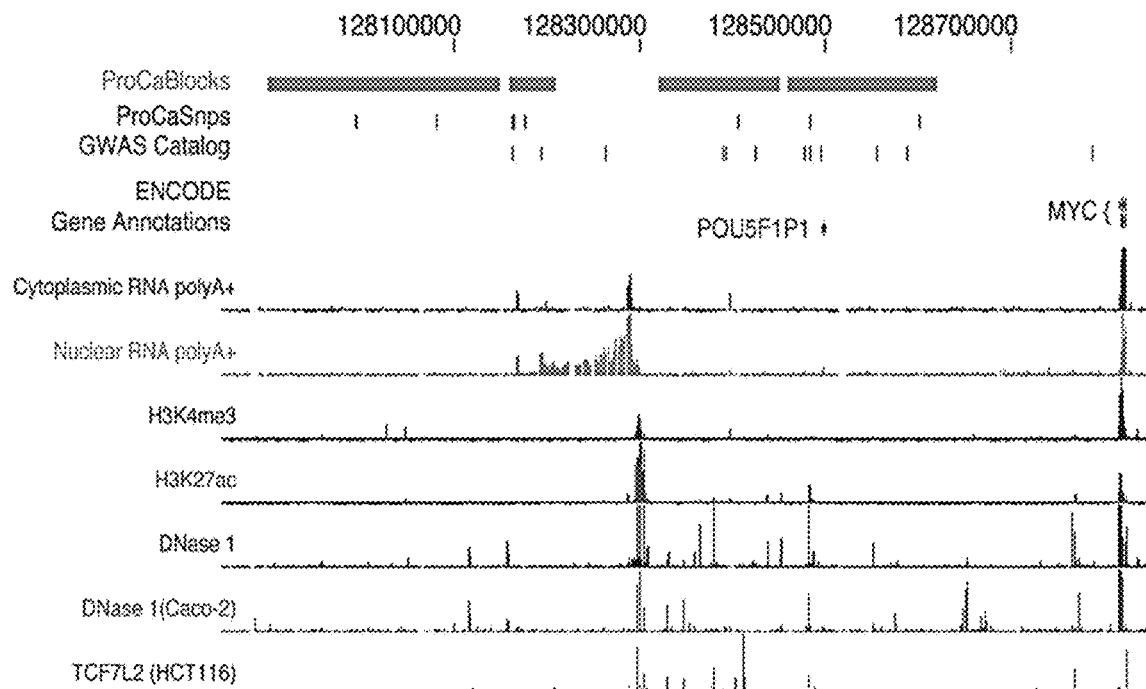
FIG. 8A-B shows examples of histone modifications, DNaseI hypersensitive sites, SNAseI for different cell lines and for comparing cell lines are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e1001046 (2011). As exemplary embodiments: DNaseI hypersensitive sites in liver and colon carcinoma cell lines (HepG2 compared to Caco-2), as ENCODE data indicate non-coding regions in the human chromosome 8q24 loci associated with cancer, see ENCODE. The ENCODE Project Consortium (2011) A User's Guide to the Encyclopedia of DNA Elements (ENCODE). PLoS Biol 9(4): el001046, herein incorporated in its entirety.
Figure 8B:
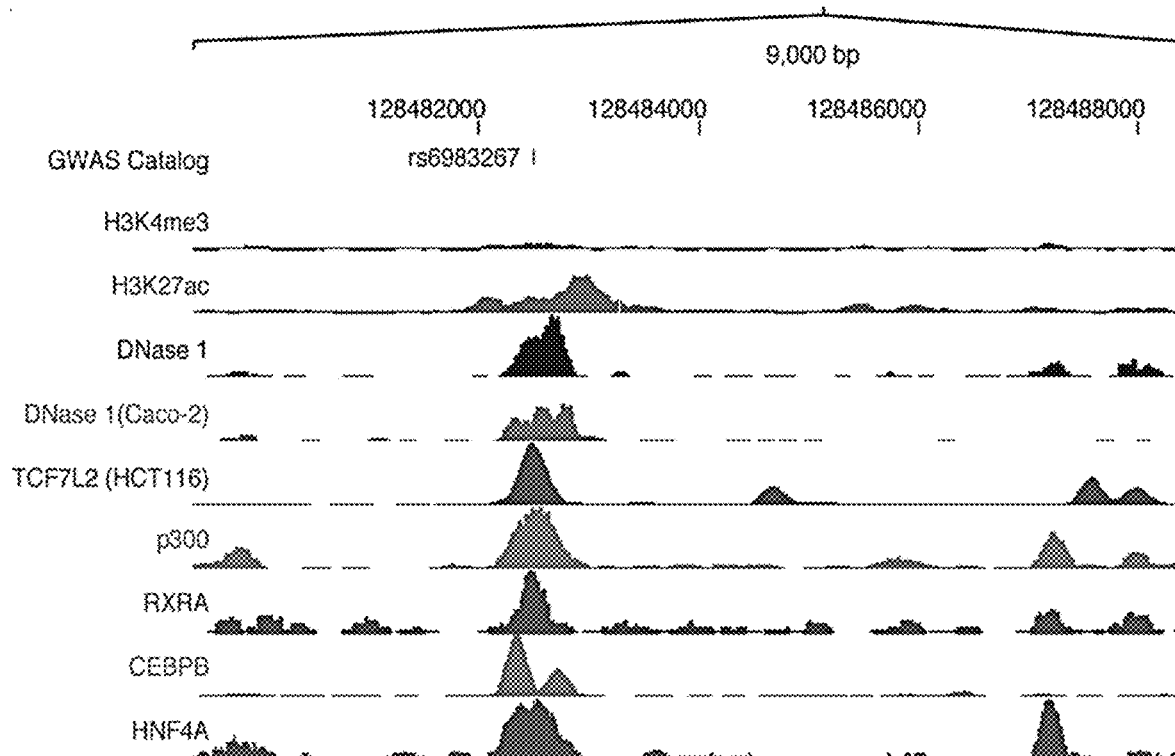

In the cells of plants and animals, DNA is packaged or wrapped up into nucleosomes where the DNA double helix is wrapped around a central core of protein (see FIGS. 4B-4C). About 150 letters-worth of DNA (or base-pairs) is wrapped around each nucleosome, and this helps package the 3 billion base pairs of genetic code into each of our cells. Nucleosomes are compact, but the ends or "tails" of the proteins that make up the nucleosome, which are called histones, stick out from the otherwise compact nucleosome structure. Like the methyl tags on DNA, small chemical tags can also be added to these histone tails (see FIG. 4C). Two of the chemical tags that are added to these tails are acetyl groups and methyl groups. Methyl, acetyl and a few other types of tags can be added to the tails in a large number of combinations and this effects whether an underlying gene is switched on or off. In fact genes can be switched right off (called silencing), full on, or somewhere in between (partial) by DNA methyl tags and histone tail tags. The combination of DNA and histone tags can also effect how easily a gene is turned on or off.

A. When Cells Divide.

When cells divide, the entire DNA sequence from the original cell (3 billion base pairs contained in 23 pairs of chromosomes in a human cell) is duplicated so that both daughter cells receive an exact copy. What, you might ask, happens to all those epigenetic tags? We have known for some time that the DNA-methyl tags are copied too, so that both daughter cells have the same pattern of DNA methylation. We now know that the pattern of histone tags is also mostly duplicated as cells divide, although this is currently less well understood. Nevertheless, cell division is also a time when epigenetic tags can most easily be changed. Thus, an epigenetic signature can apply to some characteristics passed from a cell to its daughter cells in cell division. Further, at least some epigenetic events induced in one generation, may be detected in daughter cells that underwent numerous cell divisions in later generations, long after the initial epigenetic event. Further, depending upon when the epigenetic event occurred, and depending upon the stage of the cell or type of cell containing the epigenetic event(s), epigenetic changes may alter traits of a whole organism. In yet further affects, epigenetic changes may be passed to offspring, thus over riding actual DNA coding effects. Such epigenetic overrides occur in certain diseases, such as Angelmann and Prader-Willi syndromes.

Additionally, epigenetic events alter cells through epigenetic chemical tags added to chromosomes (DNA and or histones) that may be silent, i.e. do not affect a change in cellular function by not changing gene expression. As opposed to epigenetic events which alter cells by switching genes partially on, on, e.g. "expressed" or off.

The following sections include embodiments of specific types of epigenetic changes that might be measured or detected through the use of a microfluidic epigenetic device as described herein. Examples of embodiments of epigenetic events contemplated to be detected from microfluidic chip samples are described herein. When a change, or lack of a change in the case of a pattern or signature, is discovered to be associated either singly, or as part of a pattern or signature, that epigenetic event will be incorporated into a signature associated with a particular base-line sample. In additional embodiments, signatures from test samples will be determined using the same type of epigenetic event evaluations for use in comparing to an epigenetic signature from a base-line sample. In yet further embodiments, signatures from test samples will be determined using the same type of epigenetic event evaluations for use in comparing to an epigenetic signature from a base-line sample.

B. Epigenetic Events and Identifying Epigenetic Tags (Markers).

Epigenetic tags that may find use in the analysis of differences, alterations, etc. of epigenetic events, in addition to those examples provided herein, epigenetic information may be found, merely for examples, in exemplary online databases such as hosted by the National Human Genome Research Institute (NHGRI) as ENCODE (Encyclopedia of DNA Elements) Consortium (https://www.genome.gov/), an ongoing venture to identify patterns of epigenetic tags in many different types of cells, apparently grown in static cultures, for the entire human genome (http://genome.ucsc.edu/ENCODE/), along with a users guide: The ENCODE Project Consortium (2011) A User's Guide to the Encyclopedia of DNA Elements (ENCODE). PLoS Biol 9(4): e1001046, herein incorporated in its entirety. As one example, HUVEC cells (Lonza CC-2517) propagated (expanded) in T225 tissue, a Caco-2 cells cultivated in culture flasks (i.e. static) culture conditions.

Examples of types of epigenetic events and methods of identification include but are not limited to: DNA Methylation: Methyl Array, Methyl RRBS, etc.; Open Chromatin: DNase-DGF, DNase-seq, FAIRE-seq, etc.; RNA Binding Proteins: RIP Gene ST, RIP Tiling Array, RIP Validation, RIP-seq, etc.; RNA Profiling: CAGE, Exon Array, RNA-chip, RNA-PET, RNA-seq, Small RNA-seq, etc.; TFBS & Histones: ChIP-seq, etc.; Other: 5C, ChIA-PET, Combined, DNA-PET, Genotype, Nucleosome, Proteogenomics, Replichip, Repli-seq, etc., with kits available for epigentic identification, including but not limtied to HumanMethylation450 BeadChip Kits, detecting presence or absence of methylation for at least 450,000 Methylation Sites (Illumina—Methylation 450K BeadChip).

Further, histone acetylation or other tags may be determined by antibodies specific for histones, including but not limited to H2AFZ, H3K27ac (e.g. Rabbit polyclonal (abeam ab4729) Antibody Target: H3K27ac), H3K27me3, H3K36me3, H3K4me1, H3K4me2, H3K4me3, H3K79me2, H3K9ac, H3K9me1, H3K9me3, etc. As one example, antibodies may be used for determining such histone acytlyation in HUVEC cells grown microfluidc chips (under flow). As other examples, alterations in CTCF (zinc finger transcription factor) as an epigenetic event may be detected using a Rabbit polyclonal (Millipore 07-729) Antibody Target: CTCF. Further, in some embodiments, ChIP-sequencing, also known as ChIP-seq, may be used as a method to analyze protein interactions with DNA. ChIP-seq combines chromatin immunoprecipitation (ChIP) (DNA-bound protein is immunoprecipitated using a specific antibody) with massively parallel DNA sequencing to identify the binding sites of DNA-associated proteins. Massively parallel DNA sequencing refers to any of several high-throughput approaches to DNA sequencing using the concept of massively parallel processing; it is also called next-generation sequencing (NGS) or second-generation sequencing. MPP (massively parallel processing) is the coordinated processing of a program by multiple processors that work on different parts of the program, with each processor using its own operating system and memory.

C. Chromosomal Structure and DNA Packaging within Cells.

Figure 2A:
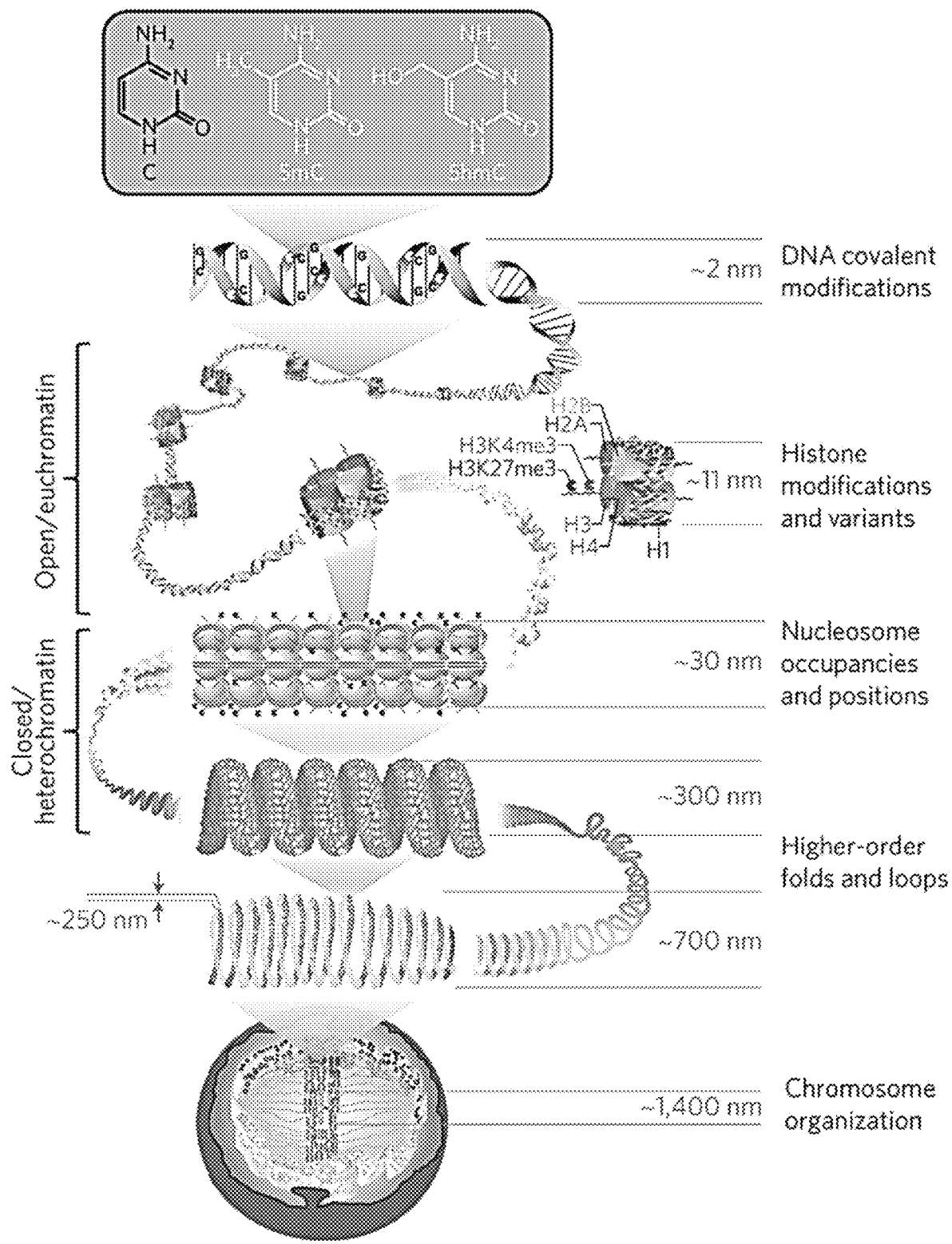
FIG. 2A shows an exemplary schematic overview of epigenetic layers and corresponding size scales. The root layer is the DNA sequence and covalent modifications such as cytosine methylation (5mC) and hydroxymethylcytosine (5hmC). The DNA is then wrapped around octameric histone proteins into nucleosomes and into chromatin. The nucleosomal histones H2A, H2B, H3 and H4 form pairs with one H3-H4 tetramer and two H2A-H2B dimers and can be exchanged with variants or chemically modified on their protruding tails such as histone 3-lysine 27-trimethylation (me3): H3K27me3. The structure of the chromatin is mediated by the nucleosome packing with open/euchromatin having less nucleosomes positioned than closed/heterochromatin. The condensed heterochromatin has been shown to possess a unique solenoid structure and higher-order loops and folds also exist to further compact the chromatin into chromosomes. The various layers and modifications establish whether the gene and the regulatory components (promoter, enhancer) are accessible and transcribed or inactive. DNA cytosine methylation and histone modifications such as H3K27me3 are broadly associated with inactive genes as to where hydroxymethylated cytosine bases and histone modifications such as H3K4me3 are nominally associated with active genes and regulatory elements.
Figure 2B:
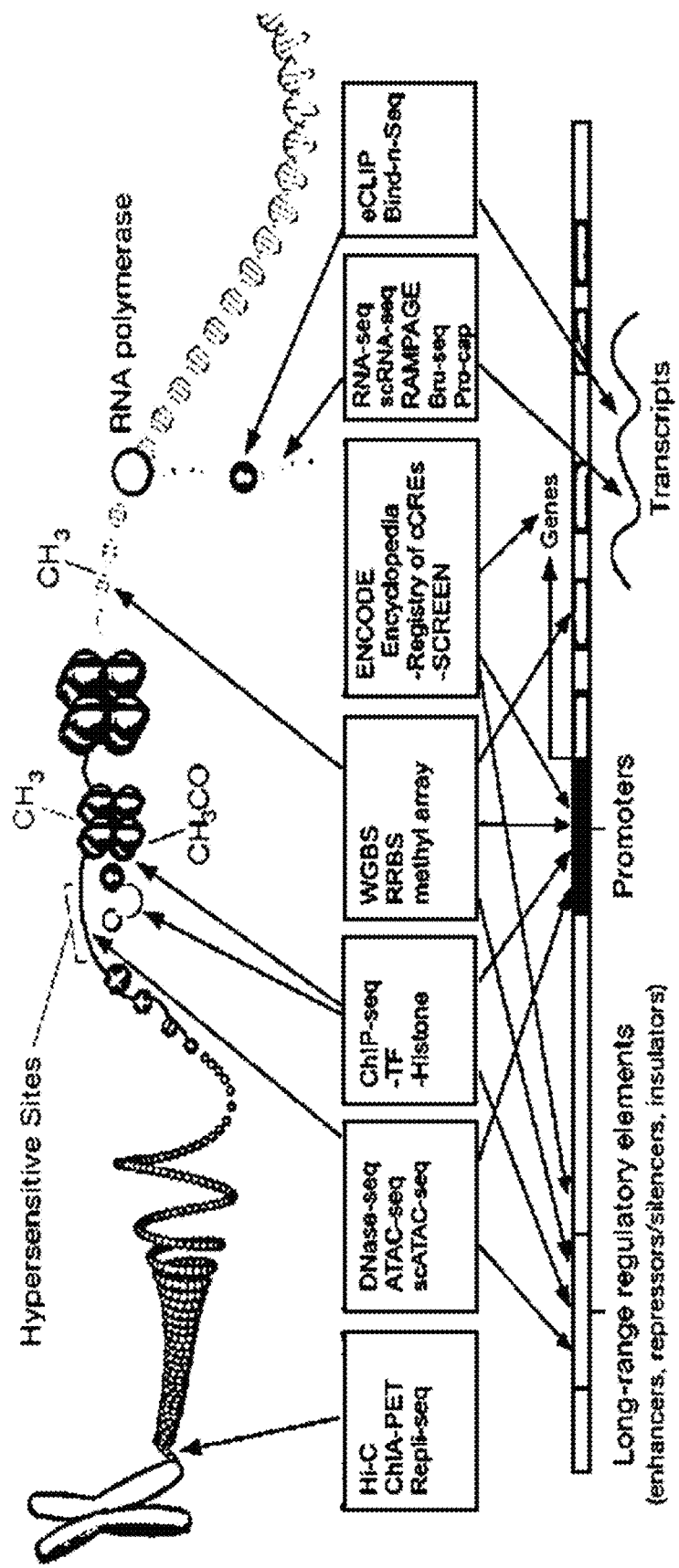
FIG. 2B shows an exemplary schematic illustration linking levels of DNA (deoxyribonucleic acid) folding (above-right to left shows increasing folding with round protein caged balls representing nucleosomes) in relation to examples of epigenetic tags, linked to assays (boxes) capable of detecting that tag further linked to exemplary areas in and surrounding genes (below).

Eukaryotic organisms package nearly two metres of DNA into a small nuclear compartment using a series of hierarchical layers. The temporal structural and chemical alteration of these layers influence gene activity and various cellular programs. The lowest layer of compaction occurs through wrapping of DNA into a nucleosome, which is formed from approximately 146 base pairs (bp) of DNA wrapped around a protein octamer. The protein octamer is composed of eight sub-units called histones (H2A, H2B, H3, H4) that assemble as one H3-H4 tetramer and two H2A-H2B dimers (FIGS. 2A-B). An individual nucleosome is separated from an adjacent nucleosome by linker DNA, whose length can range from several kbp to as small as several base pairs. The underlying DNA and histones can be subjected to modifications that alter DNA accessibility for transcription factors and other molecules such as RNA polymerase. Modifications to the underlying DNA, such as cytosine methylation, which occurs on the fifth carbon residue (5mC) and typically on cytosine-guanine dinucleotides (CpG), are distributed across the genome and into discrete patterns. CpG dinucleotides are generally underrepresented in eukaryotic genomes but most (60-80%) are methylated. The modifications conferred onto histones primarily occur on the protruding amino-terminal tails, which include methylation, acetylation, phosphorylation, ubiquitylation, sumoylation and others as well as their different forms (mono, di, trimethylation for example). The histones can also be exchanged with variants (such as H2A.X, H2A.Z, H3.3) and the modifications and variants have both been associated with many functional responses. The location and timing of the modifications to the DNA and histones work together to define the shape of the chromatin and epigenetic state. Local patterns of chromatin are typically described in two forms (open/euchromatin or closed/heterochromatin), and each has a unique scale. Euchromatin is commonly described with a "beads on a string" model, with the DNA (string) having a diameter of approximately 2 nm and nucleosomes (beads) having a diameter of approximately 11 nm. In this open form, DNA is much more accessible for DNA-binding proteins and polymerases and consequently, gene-rich areas tend to be packaged into euchromatin. Chromatin can also be packaged into a more condensed fibre called heterochromatin, which can contain many repetitive sequences and fewer genes and is frequently found near the nuclear lamina. Heterochromatin is packaged into a larger diameter fibre (approximately 30 nm) and is aided by the H1 linker histone protein, which tightens the folding of the DNA around the nucleosome by attaching where the DNA enters and leaves the nucleosome. The epigenetic state can be described by chromatin packaging and transcriptional activity using several DNA and chromatin modifications. For example, the modification of Histone 3 on the Lysine 9 residue by trimethylation, H3K9me3, has been associated with heterochromatin and transcriptional inactivity. In contrast, cytosine bases that are hydroxymethylated (hydroxymethylation, 5hmC) and the modification of Histone on the Lysine 36 residue by trimethylation, H3K36me3, have both been associated with transcriptional activity. Chromatin is not static; rather DNA packaging is dynamically adjustable based on cues from environmental stimuli and activated cellular pathways. As local chromatin packaging changes, global patterns of chromatin organization also change through higher-level loops and folds, which in turn influence intra and inter-chromosomal interactions as well as nuclear compartmentalization.

D. Motivations for Monitoring Epigenetic Phenomena.

The transient activation or repression of gene expression and various cellular programs is partially controlled via epigenetic modifications. A model of this regulation is mammalian development, where changes in chromatin accessibility at loci are mediated by DNA cytosine methylation and several histone modifications. These epigenetic modifications and chromatin landscapes enhance or prevent transcription of developmental genes that define how a single genome can produce multiple cell types during embryonic development and preserve each cellular identity throughout life. An example of this regulation is a bivalent domain, which is two histone modifications that are located in the same region that demarcate different chromatin states (one modification is associated with active gene promoters: Histone 3-Lysine 4-Trimethylation, H3K4me3, and the other is associated with inactive genes: Histone 3-Lysine 27-Trimethylation, H3K27me3). The gain or loss of one histone modification in a bivalent domain in an embryonic stem cell influences chromatin structure and transcription at that locus, further nudging the cell to differentiate into a specific cell type. These epigenetic patterns also influence deleterious cellular processes such as cancer. For example, profiling DNA cytosine methylation from different types of breast cancer tumor biopsies showed each tumor could be categorized by metastatic risk and the patterns of hypermethylation were also shared by glioma and colon cancer. Regions with CG-dense sequences, also known as CpG islands, which are found near or on gene promoters, are largely unmethylated but hypermethylation of CpG islands has been found in nearly every tumor type. Histone modification patterns also show differences between normal and cancer cells, with multiple tumor suppressor genes undergoing chromatin remodeling that can lead to aberrant gene expression and tumourigenesis. Because DNA and histone modifications influence the 3-D chromatin landscape and how different loops and folds spatially contact one another, it is not surprising that a link between chromosomal alterations that are a hallmark of cancer and chromatin organization has also recently been shown.

Early development and diseases such as cancer emphasize how the different epigenetic layers work in combinations across length scales and the genome. To characterize these types of epigenetic modifications, high-throughput sequencing technologies have primarily been utilized. There are two technologies used to generate most epigenetic maps. The first is bi-sulfite conversion followed by sequencing (BSC-Seq), and the second is chromatin immunoprecipitation followed by sequencing (ChIP-Seq). BSC-Seq is used to study DNA cytosine methylation and operates by treatment of purified DNA with bisulphite, which converts all cytosine residues to uracil except those that are methylated, followed by sequencing the products to reveal the genomic location of the residual untransformed cytosines. There are numerous other modifications of bases that are not revealed by BSC-Seq, for which techniques are evolving. ChIP-Seq uses antibodies to capture chromatin fragments bearing specific modifications. Release and sequencing of the DNA from the captured chromatin fragments identifies the genetic sequence associated with the selected modification and alignment to the known reference sequence, permits mapping of where the histone modifications existed throughout the genome. Both strategies construct detailed landscapes of epigenetic modifications but primarily rely on a large number of cells to determine statistically significant enrichments from background. They typically interrogate one mark at a time (rather than combinations) and ChIP-Seq cannot determine the absolute level of modifications (just presence). For example, if two copies of a histone are modified within the same nucleosome, ChIP-Seq cannot determine if there are one or two. Moreover, because chromatin patterns and remodeling processes are dynamic and vary across time and cellular types, ensemble measurements may be confounded by sample inhomogeneity and average out effects such as noise that can potentially contribute to phenotype and disease. Accordingly, one of the primary research goals of the new methods is to reduce the required number of cells from thousands to single cells and to simultaneously quantify multiple epigenetic modifications. This goal is particularly relevant for rare cell types such as circulating tumor cells and tissue biopsies, which are often extracted with a mixture of cells and conventional analysis, will only provide chromatin signatures of the most abundant type. While reducing the cell requirement will abate the heterogeneity of the signal, the transient dynamics of the chromatin fiber and remodeling processes are not captured.

Therefore, new technologies are required that can dynamically track multiple epigenetic marks through intermediate states and scale to look at the interplay between local composition and global organization as well as operate from a single cell.

The sizes of the molecular machines that drive and organize the epigenetic layers are at the scale of micro and nanodevices (0.1-20,000 nm). Advances in micro and nanofabrication have facilitated construction of devices that can utilize novel physical phenomena to enable study of single cells and molecules with high precision. The coupling of nano and micro technologies also permits a path for interfacing to smaller sample sizes, microfluidic automation and chip-based parallel processing. Sets of micro and nanotechnologies are presented and examined in the following sections and grouped by the type of epigenetic layer each has been utilized to probe. Lastly, technologies that have been used to investigate structural dynamics of chromatin and higher-order folding principles are examined.

E. Mapping DNA Modifications.

The placement and timing of covalent modifications to DNA participates in many cellular processes including initiation of diseases such as rheumatoid arthritis and cancer. There are multiple technologies to detect and map DNA cytosine methylation but the most popular uses bisulfite-conversion of the DNA, which converts unmethylated cytosine bases to uracil, followed by sequencing. While this approach possesses single-nucleotide resolution and can scale to the full genome, this technique also has several limitations, which were previously described.

One relatively new approach with single-nucleotide resolution involves single-molecule DNA sequencing. In this approach, individual DNA molecules are analyzed by observation of individual polymerase enzymes using an array of nanostructures to isolate the molecules for optical monitoring. A nanometre-scale aperture, smaller than the illumination wavelength, reduces the optical interrogation volume such that enzymatic incorporation of individual nucleotides by a single DNA polymerase can be monitored in real-time. The observation of one of four different colored fluorescent labels identifies the incorporated base, and from the temporal order of incorporation, the sequence of the individual molecule is derived.

Reaction kinetics for base incorporation depends on the chemical modifications of the bases in the DNA strand being sequenced. In some cases, these modifications can be identified by characteristic time differences between base incorporation events while the identity of the base is determined by the color of the fluorescence. In this way both genetic sequence and the chemical base modifications may be determined.

Detection of 5mC, hydroxymethylcytosine (5hmC) and 6-methyladenine (6 mA), exemplary epigenetic tags, was accomplished in this way. As discussed herein, 5mC plays a role in development and cancer, and 5hmC, which is an oxidized product of 5mC, is enriched in the brain and slightly less in other cell types and tissues. In contrast to the cytosine modifications such as 5hmC, 6 mA is not abundant in mammalian cells, but is found abundantly in prokaryotes and has implications for metagenomic studies and regulation of pathogenicity.

Covalently modified base on a DNA strand entering the polymerase, which may be tethered to the base of the aperture. Different times between base incorporations may be the result of the chemical modifications. While this approach gives reading of the precise genomic location of the modifications in relatively long (≥1 kbp) single DNA molecules, the incorporation rates observed may not unambiguously identify the chemical nature of the modifications.

Additionally, there are computational challenges associated with mapping millions or billions of reads in a time-efficient manner and interpreting the context with which the identified modification exists (CpG island, promoter, phenotype, environment, etc.). Another strategy being investigated is to profile an individual DNA molecule by direct imaging of fluorescently tagged base modifications. This set of approaches can produce a "fingerprint" pattern of the location of selected modifications but they do not have the ability to provide the exact sequence position of the modifications. This is because DNA molecules in physiological solutions are an ensemble of random coils that are in a perpetual state of movement from Brownian agitation and chemical interactions with proteins. To obtain a positional map of the DNA modifications, the molecules must be oriented so that the positions can be easily determined. One strategy to overcome the random conformations is to orient and stretch the molecule to approach its contour length. Molecular combing of DNA is a technique that stretches DNA on a surface using a moving liquid meniscus and has been used for genetic mapping using fluorescent hybridization probes. Capillary assembly is a related technique that uses a microstructured piece of silicone rubber and a single liquid droplet that is dragged over the topography. The receding liquid (which contains DNA molecules) gets trapped in the topography and any molecule within the meniscus gets pulled apart and aligned in the direction of the capillary forces. The moving meniscus leaves behind the stretched molecules, which can be transferred to a substrate and optically mapped or barcoded for cytosine methylation sites. An array of single stretched DNA molecules after capillary assembly may have visible fluorescent markers (DNA-red, methylation-sensitive peptide tag-green).

Another method to unfold a DNA or chromatin molecule is to use nanoconfinement, in a channel with width and depth smaller than the DNA persistence length (approximately 50 nm for physiological conditions). Capillary assembly and nanochannel profiling can be highly parallelized for simultaneously imaging thousands of molecules in a compact form factor. One limitation to conventional optical mapping of DNA modifications is diffraction-limited resolution (approximately 200 nm or approximately 588 bp), which is insufficient to resolve modifications that are in close proximity such as those found in CpG islands. This limitation may be ameliorated with super-resolution microscopy or other high-resolution techniques such as electron microscopy.

Nanopore-based sensing offers a method for profiling covalent DNA modifications on a single molecule. Nanopore sensing is based on a pore in a dielectric membrane that separates two electrolyte solutions, where one solution contains a concentration of DNA molecules. A voltage bias across the membrane drives an ionic current through the nanopore that a DNA molecule partially blocks as it passes through the pore. Characterizing the translocation time and current blockade provides structural and compositional information about the molecule moving through.

For example, recently single DNA molecules with various cytosine modifications (5mC, 5hmC) were translocated through a solid-state nanopore. While this approach could determine the relative proportion of some modifications on a single molecule, mapping the position of the modifications was not achieved. This limitation was in part due to the speed of the molecule translocating through the nanopore. To enhance the detectability of methylated cytosines during translocation through the nanopores, another approach labeled methylated cytosines using methyl binding domain proteins (MBD1). This method was able to coarsely determine the number of methylation sites per molecule from the fraction of bound proteins. The identification and differentiation of base modifications without a label remains an issue with solid-state nanopore profiling, but biological nanopores have been used to resolve individual bases along a single DNA fragment with substantially lower translocation speeds.

The signal from a DNA strand being pulled through a protein nanopore (α-hemolysin) may be measured. This approach is at an early stage, but it may enable protocols for simultaneously reading genomic and epigenomic maps with electronic detection.

There is clearly a need for richer information about the complex patterns of covalent DNA modifications and interest in obtaining this information more rapidly from smaller numbers of cells continues to grow. The discussion above involved the analysis of relatively durable chemical modifications that can survive relatively harsh treatment and techniques for stretching and orienting the DNA molecules. This is not the case for chromatin with its more delicate histone protein structure and different approaches and devices are required to analyze histone modifications and chromatin structure. Such techniques as described herein, may find use added to microfluidic devices as described herein.

F. Mapping Histone Modifications and Nucleosomes.

The positions of nucleosomes and numerous modifications of their individual histones as well as their variants also regulate transcription and cellular fate. Determination of the presence and location of chromatin modifications is typically performed using ChIP-Seq techniques, which use an immunoprecipitation step and a sequencing step. ChIP begins with cross-linking the proteins to the DNA, lysing open the cells, extraction of the nuclei and shearing into smaller fragments. The sheared chromatin is then immunoprecipitated, followed by reversal of the cross-links and disassociation of the protein-DNA complexes and DNA isolated for sequencing. While this approach can be somewhat automated with liquid-handling robots, the number of manual steps take time, require large numbers of cells and can result in significant user-variability. Moreover, antibody specificity continues to remain an issue that limits reproducibility of ChIP-Seq Experiments.

G. Chromatin dynamics and organization.

Conventional ensemble technologies such as BSC-Seq and ChIP-Seq have been successful at mapping some aspects of epigenetic modifications of chromosomes, but do not address the structural effects of their presence. To dissect these subtle forces that influence chromatin structure and activity, techniques such as optical and magnetic tweezers and atomic force microscopy have been used. These methods have provided mechanistic insights into forces and structures that influence dynamic chromatin processes such as nucleosome assembly chromatin remodeling and higher-order chromatin organization. Using these insights, novel mechanical models can be constructed to characterize how DNA is packaged into chromatin and forms loops and folds to accommodate transcription factors and chromatin remodeling enzymes and how these displacements propagate within the nucleus during different activities.

At a fundamental level, when DNA wraps around the histone octamer and forms a nucleosome, several points of contact form between the two. The locations of contact can be determined using crystallography but the strength of those contact points cannot be measured. Sensitive force spectroscopy techniques such as optical and magnetic tweezers can measure these contact locations and forces and gauge them dynamically. Optical tweezers operate by trapping a small dielectric particle with a focused laser beam and monitoring its displacement using a second laser probe beam. When a single chromatin fiber is attached to the bead and the other end is attached to another bead or surface such as a cover slide or micropipette, small displacements (and forces) imposed on or by the fiber can be measured. The high force-sensitivity (approximately 1 pN) of optical tweezers permits measurement of the strength and location of histone-DNA interactions on a single nucleosome and the associative forces between the histone octamer and DNA during interactions with RNA polymerase or a chromatin remodeler (SWI/SNF). Optical tweezers experiment include a single nucleosome is tracked on a short template of DNA as it cyclically wrapped and unwrapped. This elegant study was able to track the path of an RNA Polymerase II complex as it transcribed DNA through nucleosomes containing modifications on the histone tails or histone-DNA contacts and showed differential effects for the nucleosomal barrier to transcription elongation.

Magnetic tweezers employ a pair of macroscopic magnets to create a magnetic force gradient on a small magnetic bead that is tethered to a single molecule. The single molecule is attached at its end to a glass slide and manipulation of the position of the magnets induces a stretching force. Magnetic tweezers possess higher force sensitivity ($10^2$ pN) than optical tweezers, and an experiment was done where magnetic tweezers were used to stretch a single heterochromatin fiber. By precisely displacing the chromatin fiber and measuring the resistive force, the chromatin fiber was observed to behave as a Hookian spring with distinct conformations for different forces. The compliance of the spring was found to be remarkably low, which facilitates high flexibility and extension (>20%). The Hookian spring-like behavior offered several insights about chromatin structure, one of which is heterochromatin is organized into a solenoid shape, with stacks of nucleosomes in a helical structure that keep the DNA both highly compacted yet accessible. This result underscores how single molecule force spectroscopy assays can reveal insights into not only chromatin shape and packaging within the nucleus, but also how these structural features dynamically evolve during interactions with chromatin remodeling complexes.

III. Exosomes.

"Exosomes" refer to cell-derived vesicles shed into and found in eukaryotic fluids, including but not limited to extracellular spaces and fluids, such as blood, urine, etc. "Exosomes" are typically small, lipid bilayer membrane extra-cellular vesicles (EVs), ranging approximately from 30-150 nm in diameter. Exosomes, as vesicles prior to release from a cell, may be of cellular endosomal origin and released during reticulocyte differentiation. Derived from the luminal membrane of intracellular multi-vesicular bodies (MVBs). Exosomes may be constitutively released from the cell by intracellular fusion with the cell membrane resulting in extracellular vesicles that are released from cells upon fusion of an intermediate endocytic compartment, the multivesicular body (MVB), with the plasma membrane. See, Guo, et al., "Exosomes: New players in cancer (Review)." Oncology Reports, 38:665-675, 2017, herein incorporated by reference in its entirety.

Figure 3:
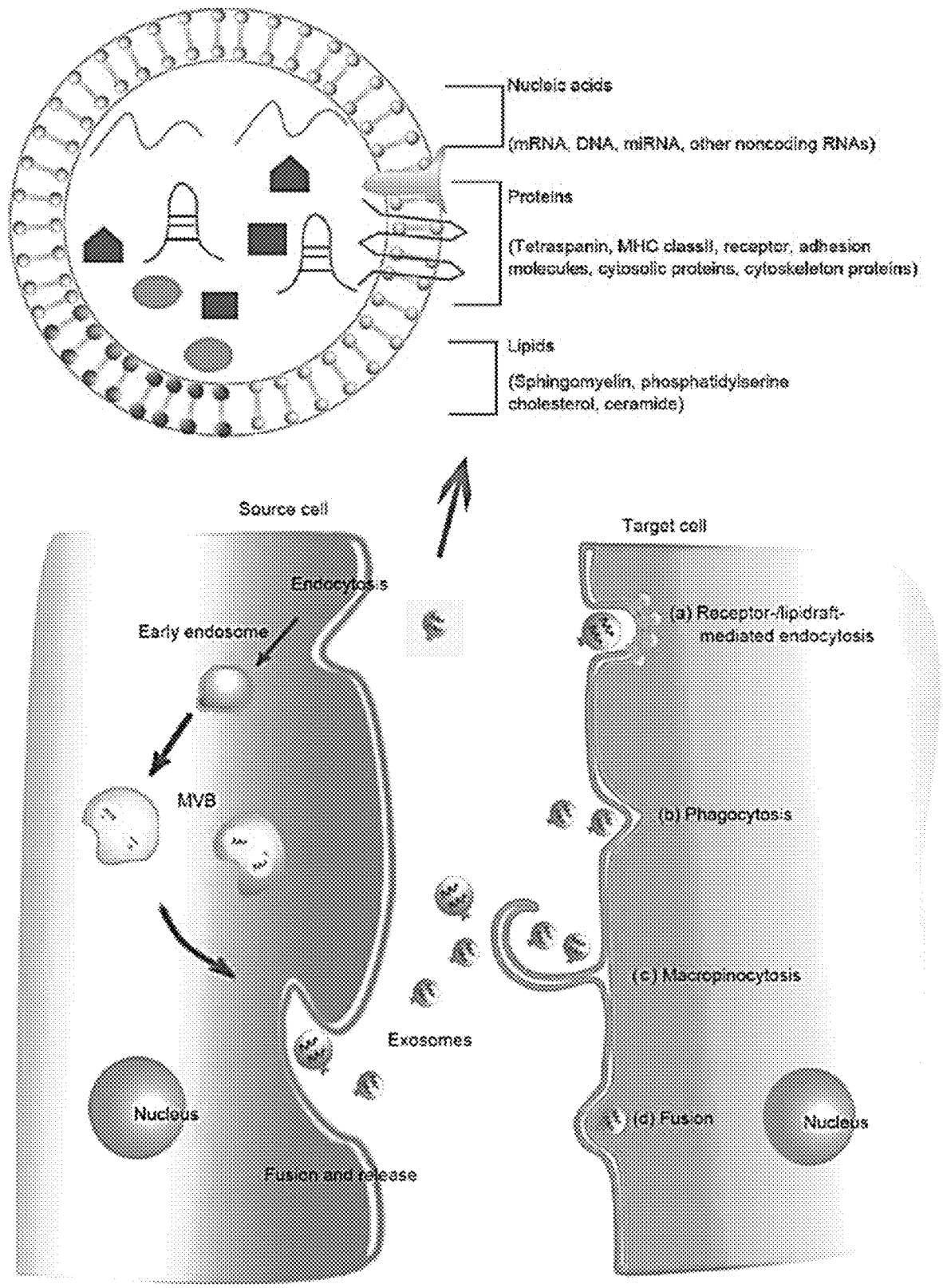
FIG. 3 shows exemplary biogenesis, release, content and uptake of exosomes. Early endosome is formed from the plasma membrane via endocytic pathway. MVB can be formed by the invagination of endosomal membrane. Dependent on the function and content, MVB then can be directed to fuse with plasma membrane and release to the extracellular space as exosomes. During the biogenesis of exosomes and prior to their secretion, proteins (e.g., tetraspanin, cytosolic proteins, receptor), nucleic acids (e.g., mRNA, miRNA, DNA), and lipids (e.g., sphingomyelin, cholesterol) may be uploaded to exosomes by cellular mechanisms. In some embodiments, exosomes released by cells are used with microfluidic devices as input exosomes. Cells appear to take up exosomes via several ways: (a) receptor-/lipidraft mediated endocytosis, (b) phagocytosis, (c) macropinocytosis, (d) fusion with the plasma membrane of the target cell. MVB: multivesicular body. See, Guo, et al., 2017. In some embodiments, after cells take up input exosomes, cells are washed to remove remaining exosomes, then exosomes released by these cells are used with microfluidic devices as output exosomes.

Multivesicular endosomes (MVE) within the cells take up bits of the cell cytoplasm and its contents, frequently including proteins and nucleic acid fragments, into membrane-bound vesicles. Conversely, cells appear to take up extra-cellular exosomes released by the same cell or released by other cells by several molecular mechanisms. Most experimental evidence suggests that exosomes are internalized into recipient cells via endocytosis. Endocytosis is a general statement for a range of molecular pathways, including calthrin-mediated endocytosis, coveolin-mediated endocytosis, phagocytosis and macropinocytosis. Moreover, the uptake of exosomes by direct cell surface membrane fusion was studied. See, FIG. 3 summarizing the complicated process of biogenesis, release, content and uptake of exosomes (Guo, et al., "Exosomes: New players in cancer (Review)." Oncology Reports, 38:665-675, 2017, herein incorporated by reference in its entirety), lower partial cell showing schematic examples of exosome formation prior to cell release with the upper exosome showing schematics of exemplary contents.

"Exosomes" may also be shed by cell containing samples into the surrounding fluids, such as cell culture medium, e.g. cell cultures, including medium bathing and flowing over cells, tissues, biopsies, etc., in microfluidic chips. Thus in some embodiments, microfluidic chips have tubing containing incoming exosomes suspended in fluids (input), where the exosomes were derived from cells (cancerous or non-cancerous) into microchannels for bathing cell samples attached to the microfluidic channels. In some embodiments, fluids are continuously flowing over samples. In some embodiments, fluids there is discontinuous flowing over samples, such that after exosomal containing fluids cover cells, flow is stopped in order to allow attached cells to take up input exosomes, then after a period of time flow is initiated to remove remaining input exosomes from the microfluidic channels. After remaining input exosomes are removed, in some embodiments, flow may continue for collecting exosomes released by cells attached to the microchannels. In other embodiments, flow may be stopped in order to concentrate output exosomes released by the cells followed by a flush of fluid in order to collect the output exosomes. In any event, fluids then flow out (as effluent) of the microfluidic device for collection of output exosomes, e.g. from untreated cell samples, from exosome treated cell samples, etc. Collected fluids (samples) are then used for further analysis, in part as described herein. Exosomes released by cells on-chip, coming off chip in effluent is referred to as output exosomes. In further embodiments, exosomes collected as output from a microfluidic channel may then be added to another microfluidic channel as input.

A. Kidney-Chips as Exemplary Targets of Exosomal Effects.

In fact, the surprising discovery of EVs isolated from blood samples of heart failure patients being taken up by and then injuring kidney cells is shown herein. Furthermore, EVs flowed into fluidic devices; such as described herein, are contemplated for testing their capability of targeting, (or selecting) a particular cell or tissue type for uptake. In other words, specific cell types or tissues are contemplated to be selective, in turn, for taking up EVs produced by particular cell types or cells under certain conditions, such as injured heart cells.

1. Exemplary Kidney-Chip Protocol

Exemplary Materials are briefly described as follows.
ECM-coating. Sulfo-sanpah (Covachem, #13414), ER1 (0.5 mg/ml) in ER2 50 mM HEPES buffer; Collagen IV (BD Corning, 50 μg/mL in Dulbecco's phosphate-buffered saline (DPBS); and Matrigel (BD Corning, reduced growth factor, 100 ug/ml DPBS).
Cells. Top channel. Human Proximal Tubular Epithelial Cells (Lonza, RPTEC #CC-2553); and Bottom channel. Primary Human Glomerular microvascular Endothelial cells (Cell Systems. ACBRI 128), expand to P7 (e.g. passage 7).
Media. Renal Epithelial Growth Medium (REGM™ Lonza, CC-3190) for Proximal tubule cells or REGM2 (from PromoCell, Cat #C-26130); and Kidney endothelial cell medium (Cell Systems, 4ZO-500).
Chip. High shear chip; under flow shear; and Tall channel closed top-chip.
Experimental reagents. Collagen IV coated 6 well plate; and Corning BioCoat Collagen IV multiwall plates, Corning #354428.

One brief exemplary timeline is described as: Day −2: Chip coating; Day −1: Seeding endothelial cells; Day 0: Seeding proximal tubule epithelial cells; Day 0-7: Maintain chips; Day 7: Start Experiment (Study), e.g. 72 hours; and Day 10: End 72 hour Experiment (Study). Exemplary readouts include but are not limited to: Phase contrast microscopic images; immunofluorescent images; barrier function (in particular for kidney-chips, etc.); and Troponin I release (in particular for heart-chips, i.e. cardiac-chips).

A more detailed exemplary timeline, e.g. (proximal-tubule) Kidney-chip is described below.

Day 0: Chip Activation and Coating
1. Wash the top and bottom channels with 200 μl of 70% ethanol each channel.
2. Aspirate the fluid from both channels.
3. Wash both channels with 200 μl of sterile water each channel.
4. Aspirate the fluid from both channels.
5. Wash both channels with 200 μl of ER2 buffer each.
6. Add working solution of ER1 (0.5 mg/ml final concentration, 5 mg ER1/10 ml ER2) to top (50 ul) and bottom (20 μl) channels.
7. Activate the channel with UV light for 20 min.
8. Gently aspirate ER1 from the channels.
9. Wash both channels with 200 μl of ER2 each.
10. Wash both channels with 200 μl of PBS each.
11. Aspirate PBS from both channels gently.
12. Add ECM in PBS (Collagen IV (50 μg/ml)+Matrigel (100 ug/ml)) to top (50 μl) and bottom (20 μl) channels of a standard S-1 closed top chip. In one contemplated embodiment, a high shear chip may be used with 15 μl each for top and bottom channels.
13. Incubate the chip at 37° C. overnight.

Next day, gently wash the channel with endothelial media.
Day 1: Endothelial Cell Seeding
1. Expand kidney Glomerular endothelial cells for 2-3 days.
   Add 5 ml of attachment factor to T75 flask and leave at least 5 seconds.
   Aspirate the attachment factor and add 20-30 ml of fresh growth media to flask and incubate at 37° C. until media is at 37° C.
   Thaw a frozen vial of cells at 37° C. in a water bath and immediately transfer the cells into a conical tube containing 14 ml of cold growth media.
   Centrifuge the cells at 900×g for 10 min at 4° C.
   Gently aspirate the supernatant.
   Resuspend the cells in 2 ml growth media and add the cells into T-75 flask.
   Culture the cells at 37° C. for 2-3 days.
2. On day of cell seeding, trypsinize the cells and spin at 900×g for 10 min at 4° C.
3. Count the cells and make 5×10^6 cells/ml density for a tall channel chip and seed 20 μl for bottom channel. For a high shear chip, dilute cells at 10×10^6 cells/ml then add 10 ul of cells into bottom channel. Final cell concentration is 100,000 cells/chip.
4. Flip the chip and incubate for 90 minutes (min) at 37° C. in an incubator.
5. Add media on top of the inlet and outlet port, gravity washing and feeding.
6. Incubate for 1 day.
7. Prior to proximal cell seeding, stop flow using tips for bottom channel.

Day 2: Proximal Tubular Cell Seeding
1. Expand Human Primary Proximal Tubular cells in 6-well plate (Collagen IV coated) for 3-4 days.
   Coat 6 well plates with Collagen IV (50 μg/ml)/Matrigel (100 μg/ml) for at least 2 h at 37° C., or use a Col IV coated plate (e.g. Corning #354428).
   Wash with Dulbecco's phosphate-buffered saline (DPBS) and seed Renal Proximal tubular cells at 180,000 cells per well (20,000 cells/cm²).
   Culture for 3-4 days.
2. Trypsinize the cells and count
3. Make 2×10^6 cells/ml for tall channel chip and seed 40 μl into top channel. For high shear chip, make 8×10^6 cells/ml density and seed 10 μl of cells into top channel. Final cell concentration is 80,000 cells per chip.
4. Incubate for 90 min at 37° C. incubator.
5. Add media REGM on top of the inlet and outlet port, gravity washing and feeding using tips.
6. Incubate for 1-2 days static (i.e. no flow).

Day 4: Start Flow at 30 Ul/Hr.
1. Warm media degassing using steriflip for 15 min at 37° C. bead bath.
2. Incubate the media at 37° C. in an incubator after loosening the cap, i.e. unscrewing the cap a bit, but not enough to allow contamination of the media, to ensure gas equilibration.
3. Add 3 ml media in Inlet port and 0.3 ml in Outlet port Reservoir.
4. Prime the perfusion manifold in the culture module.
5. Connect the chip to the perfusion manifold and start flow.
6. Change media every other day.
7. Culture for 6-7 days.

Day 7-10: Nephrotoxin Testing and Readouts.
Outflow from chips, (e.g. S1—closed top chip; and high shear (HS) chip) was collected for certain readouts. For reference, kidney endothelial media contains 5% FBS while the kidney epithelial media contains 0.5% FBS.

Read outs include but are not limited to: a Kidney injury panel from MSD (K15189D, K15188D); Kidney gene expression: transporters (MRP2, 4, MDR1, MATE1/2-K, OAT1, OAT2, OAT3, OATP4C. OCT2, MRP1/3/5/6, etc.);

Immunostaining: antibodies (MRP2, 4, MDR1, MATE1/2-K, OAT1, OAT2, OAT3, OATP4C, OCT2, MRP1/3/5/6, etc.)

2. Exemplary Heart Related Diseases Simulated Using

Embodiments of Cardiac-Chip (Heart-Chip) EVs and Kidney-Chips.

In one exemplary embodiment, EVs were collected from the blood samples of human subjects who were either healthy (control), or were classified as having heart failure (HF) or cardiorenal syndrome (CRS), then flowed into the lower channel of one embodiment of a Proximal Tubule Kidney Chip. In one exemplary contemplated embodiment, EVs may be collected from the effluent of a Heart-Chip comprising healthy cells. In one exemplary contemplated embodiment, EVs may be collected from the effluent of a Heart-Chip comprising diseased cells, as in derived from a biopsy of a heart patient, e.g. cadaver, etc. In one exemplary contemplated embodiment, "heart failure" may be simulated in the cardiac cells of a Heart-Chip. EVs may be collected from the effluent of a "heart failure" fluidic device, then flowed into the lower channel of one embodiment of a Proximal Tubule Kidney Chip. In one exemplary contemplated embodiment, "Cardiorenal Syndrome" may be simulated in the cardiac cells of a Heart-Chip. EVs may be collected from the effluent of a "Cardiorenal Syndrome" fluidic device, then flowed into the lower channel of one embodiment of a Proximal Tubule Kidney Chip.

As one example, precipitated EVs are collected from outflow by centrifuging at 10,000×g for 1 h and resuspended in Phosphate-buffered saline (PBS). EVs may be precipitated with Total Exosome Isolation Kit overnight. Unlike EV induced cells, no pellets were observed using epidermal media or outflow after overnight precipitation. For staining, EVs are stained with an exemplary DiI Stain (1,1'-Dioctadecyl-3,3,3',3'-Tetramethylindocarbocyanine Perchlorate ('DiI'; $DiIC_{18}(3)$)).

Figure 17A:
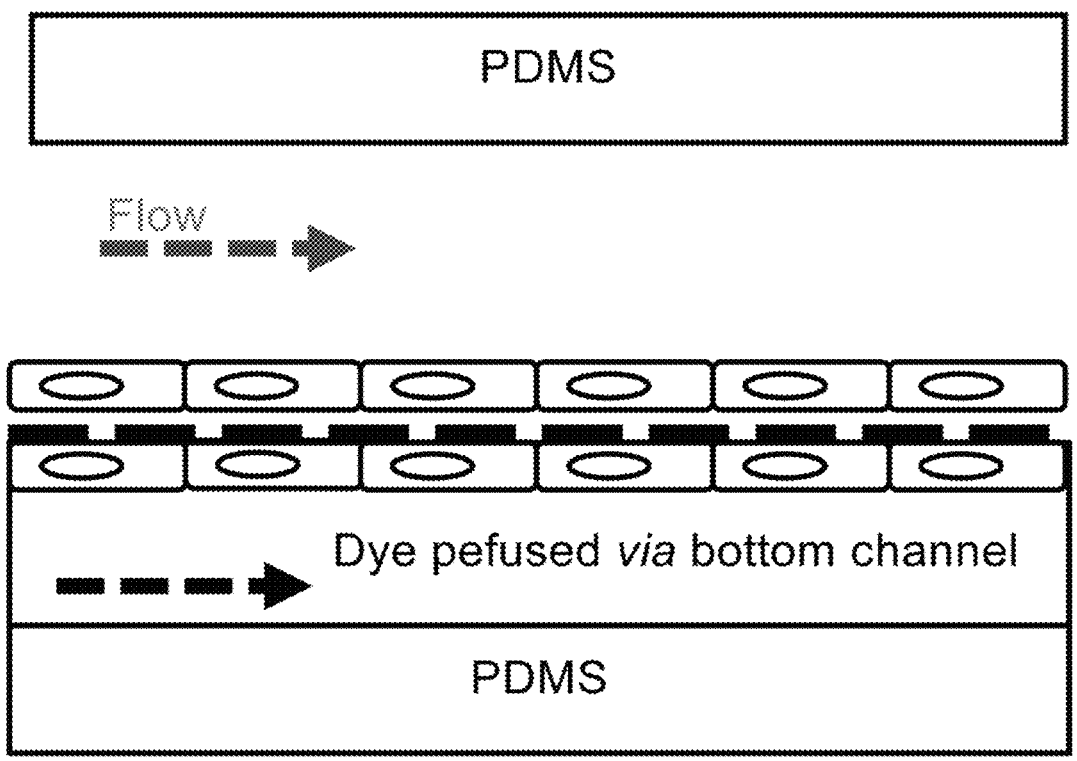
FIG. 17A-B shows exemplary barrier function in one embodiment of a proximal Tubule Chip showing a trend towards increased permeability in heart failure EV treated kidney chips.
Figure 17B:
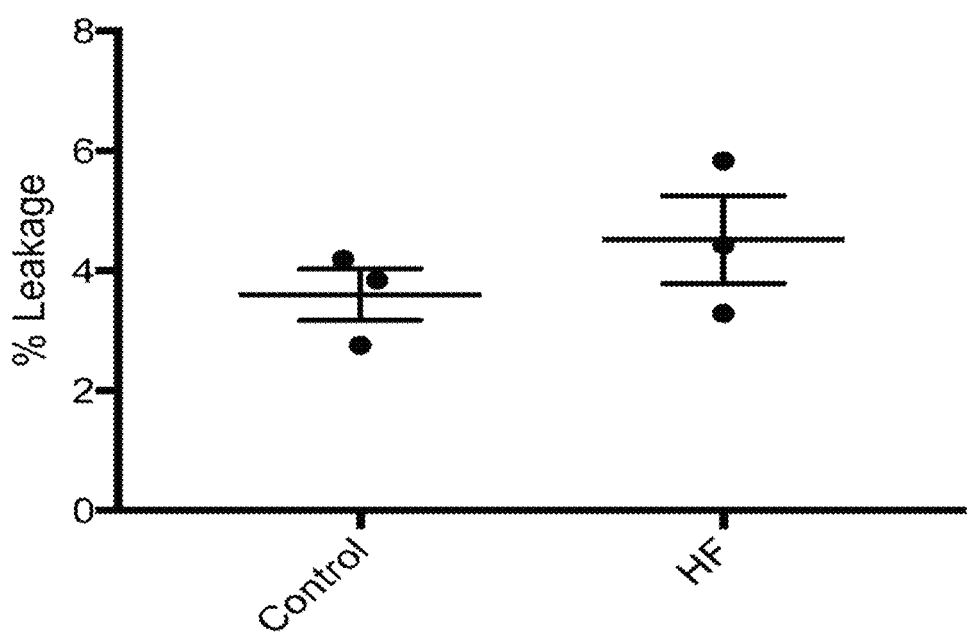

EVs isolated from "Heart Failure" patient's blood were flowed into a Proximal Tubule Chip inhibit cellular expansion over the membrane surface at 72 hours of EV exposure. FIG. 16B. Conversely, cellular expansion is visible in the "Healthy" Heart EV exposed kidney tissue. FIG. 16A. Moreover, a trend towards leaky barrier function of the cell layers exposed to EVs isolated from "Heart Failure" patients is observed compared to "Healthy" EV exposed kidney tissue. FIG. 17A-B. In a contemplated embodiment, a biomarker for kidney injury may be measured, e.g. cystatin C.

FIG. 16A-B shows one exemplary embodiment of a Proximal Tubule Chip. Baseline (top panels) 72 hour (h) EV 2 exposure (i.e. cellular contact with EVs) (lower panels).

FIG. 16A shows exemplary "Healthy" EV exposed kidney tissue.

FIG. 16B shows exemplary "Heart Failure" EV exposed kidney tissue.

FIG. 17A-B shows exemplary barrier function in one embodiment of a proximal Tubule Chip showing a trend towards increased permeability in heart failure EV 2 treated kidney chips. FIG. 17A shows an exemplary schematic of a fluidic chip. polydimethylsiloxane (PDMS) (top of chip). Arrow shows directional fluid flow over the top of the parenchymal cells, e.g. kidney cells, attached to a membrane (dotted lines). Dye if perfused through the fluid flowing through the bottom channel lined with endothelial cells over the bottom of the chip (PDMS). FIG. 17B shows exemplary changes in leakage (dye moving into the top channel) in embodiments of a kidney chip perfused with EVs from healthy patients (control) and heart patients (HF) (see, e.g. "type").

Kidney injury markers, such as Kidney Injury Marker 1 (KIM-1), were also used in readouts for assessing damage of kidney cells. Kidney Injury Molecule-1 (KIM-1) refers to a type 1 transmembrane protein having an immunoglobulin and mucin domain, whose expression is markedly up-regulated in the proximal tubule in damaged human kidney cells. The ectodomain of KIM-1 may be shed from damaged kidney cells into the urine. In some embodiments, shed portions of a KIM-1 membrane protein may be used as a biomarker for measuring the amount of kidney cell damage.

In one embodiment, EVs isolated from cardiorenal syndrome (CRS) patient's blood were flowed (perfused) into a Proximal Tubule Chip.

A comparison of KIM-1 levels, between baseline and at 72 hours of EV 3 contact, was made in undiluted outflow (effluent) samples between control, HF (Heart Failure) and CRS (Cardiorenal Syndrome) EV treated chips. KIM-1 levels >734 pg/mL (upper limit of ELISA standard curve) in epithelial channels was measured in epithelial channels of control, Heart Failure (HF), and Cardiorenal Syndrome (CRS) EVs treated chips (upper limit of ELISA standard curve). In contrast, endothelial channels had less (~100 pg/mL) KIM-1 in outflows. No cystatin C was detected in exemplary samples.

Figure 18:
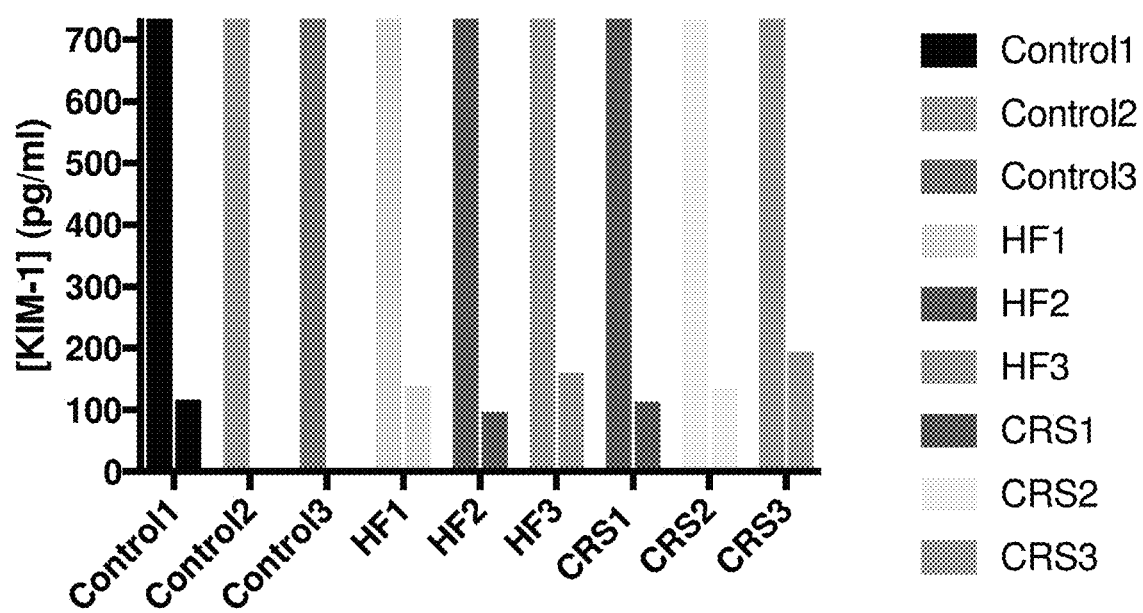
FIG. 18 shows exemplary levels of Kidney Injury Marker 1 (KIM-1) release from HF EV and CRS EV treated Kidney-chips. Undiluted outflow samples.

FIG. 18 shows exemplary levels of Kidney Injury Marker 1 (KIM-1) release from HF EV and CRS EV treated Kidney-chips. Undiluted outflow samples.

Therefore, in order to obtain actual measurements of KIM-1 release from the parenchymal kidney (epithelial) cells treated as described above, however effluent (outflow) samples were diluted 6×. Surprisingly, an exemplary comparison between media without EVs vs. CRS EV3 showed a significant reduction of KIM-1 release, calculated as significantly different using Dunn's multiple comparisons. Measured from OD450 values w/o corrections or automated results sheet.

Figure 19:
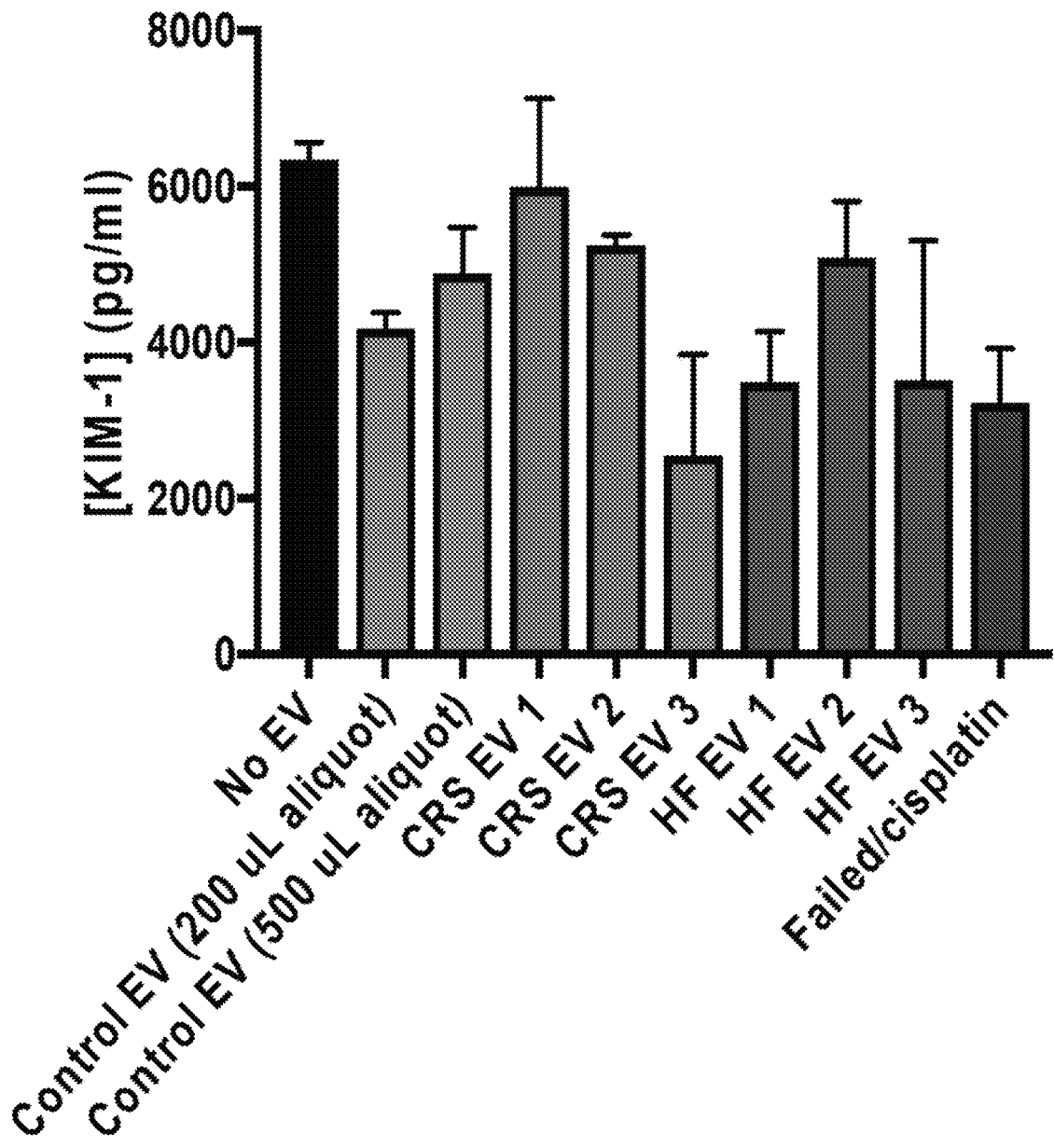
FIG. 19 shows exemplary Kidney Injury Marker 1 (KIM-1) release from HF EV and CRS EV treated Kidney-chips. KIM-1 levels were measured in 6× diluted outflow samples from epithelial channels.

FIG. 19 shows exemplary Kidney Injury Marker 1 (KIM-1) release from HF EV and CRS EV treated Kidney-chips. KIM-1 levels were measured in 6× diluted outflow samples from epithelial channels.

Barrier function was measured on one embodiment of a Proximal Tubule Kidney-Chip treated with CRS EV3, after 24 hours, as opposed to 3 days, vs. baseline (Day 0).

FIG. 20 shows an exemplary barrier function as compared to baseline, for one embodiment of a Proximal Tubule Kidney-Chip treated with CRS EV3. P-values: Baseline vs. EV 24 h. 2-way NOVA and Sidak multiple comparison.

FIG. 21A-B shows an exemplary barrier function as compared to baseline, for one embodiment of a Proximal Tubule Kidney-Chip treated with CRS EV3. FIG. 21A shows exemplary baseline cells where there is no EV exposed kidney tissue. FIG. 21B shows exemplary CRS EV 3 exposed kidney tissue after 24 h EV exposure.

Figure 22A:
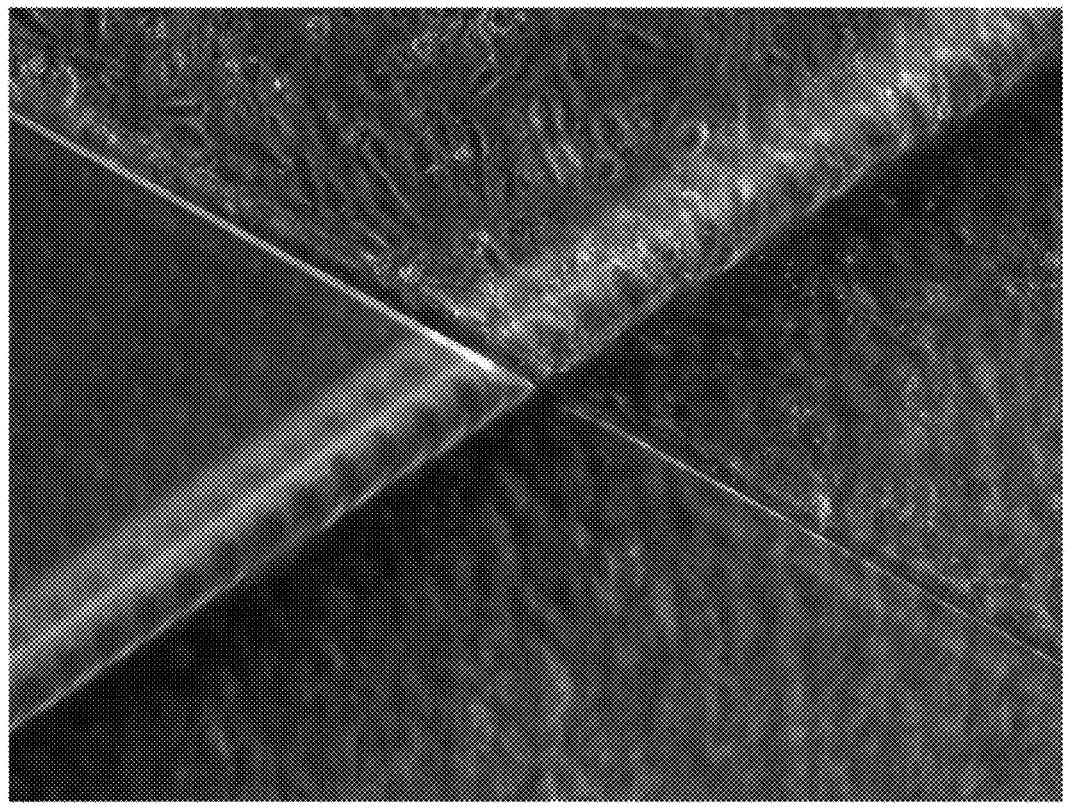
FIG. 22A-C shows exemplary uptake of EVs by endothelial cells in one embodiment of a Proximal Tubule Kidney-Chip (EV3). EVs added to lower channel. DiI (red), DAPI (blue).
Figure 22B:
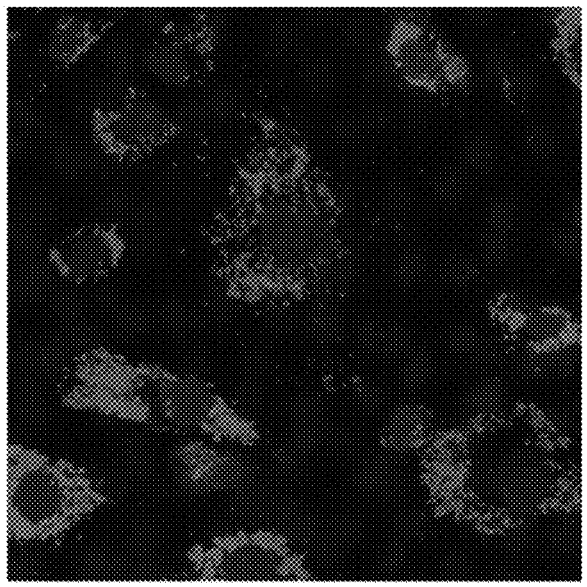

A surprising demonstration of EV uptake was observed by endothelial cells containing numerous DiI stained EVs in one embodiment of a Proximal Tubule Kidney-Chip (EV3), see FIG. 22B. A few epithelial cells showed uptake of EVs that presumable diffused from lower channel across the endothelial cell layer and fluidic device membrane.

Figure 22C:
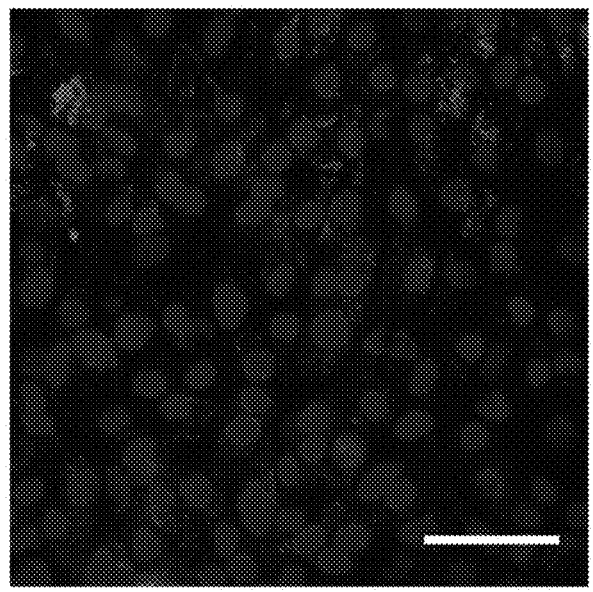

FIG. 22A-C shows exemplary uptake of EVs by endothelial cells in one embodiment of a Proximal Tubule Kidney-Chip (EV3). EVs added to lower channel. DiI (red), DAPI (blue). FIG. 22A shows an exemplary phase contrast image of an Inlet side. FIG. 22B shows an exemplary fluorescent micrograph of endothelial cells (Bottom channel) containing red stained EVs. FIG. 22C shows an exemplary fluorescent micrograph of epithelial cells (Top channel). Scale bar: 100 µm.

Figure 23:
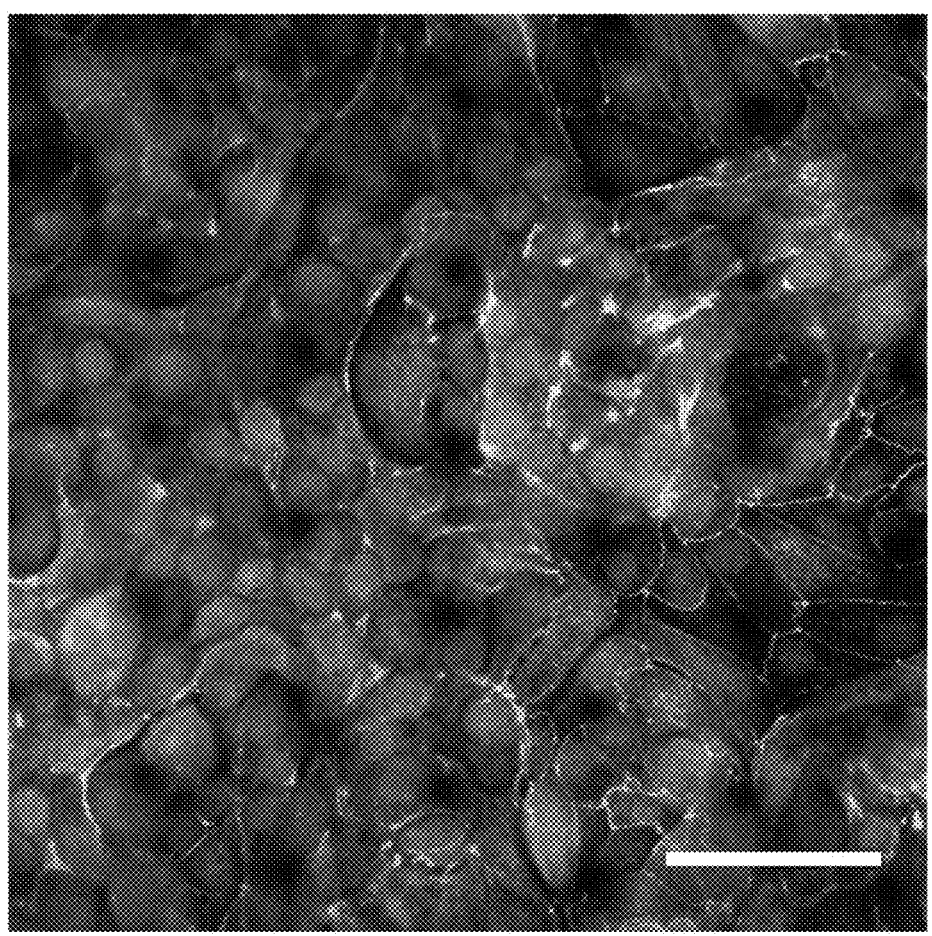
FIG. 23 shows exemplary KIM-1 Expression in one embodiment of a Kidney (EV 3) Chip. KIM-1 (red). ZO-1 (green). Nuclear DAPI (blue). White Scale bar: 100 μm.

FIG. 23 shows exemplary KIM-1 Expression in one embodiment of a Kidney Chip. KIM-1 (red). ZO-1 (green). Nuclear DAPI (blue). White Scale bar: 100 µm.

3. Additional Exemplary Embodiments

Thus, in some embodiments, epigenetic changes between exosomal contents of input vs. output exosomes may be compared for differences in epigenetic signatures. In other embodiments, epigenetic changes induced by input exosomal contents of untreated vs. treated cell samples may be compared for differences in epigenetic signatures. In other embodiments, phenotypic changes of attached cells induced by input exosomal contents of noncancerous vs. cancerous sources of exosomes may be evaluated (assessed). In some embodiments, epigenetic changes of attached cells due to incorporating input exosomes may be evaluated (assessed). Such epigenetic signatures generated using exosomes may be used as described herein, in addition for use in medical diagnostics, including but not limited to cancer patients. In some embodiments, noncancerous cells are co-cultured with cancerous cells on-chips. In some embodiments, cancerous cells, including but not limited to nonmetiastatic, pre-metastatic, etc., are seeded into microfluidic channels. In some embodiments, attached parenchymal cells on-chips may include cancerous cells. Such cancerous cells may not be attached to a membrane.

Emerging evidence suggests that exosomes derived from cancer cells are involved in tumor growth, tumorigenesis, angiogenesis, tumor immune escape, drug resistance and metastasis. Exosomes are also involved in the intercellular communication between cancer cells and stromal cells, especially with cancer-associated fibroblasts (CAFs).

When comparing exosomes with the total cell membranes, several studies observed that exosomes have a higher expression of sphingomyelin, cholesterol, phosphatidylserine, and generally of saturated fatty acids. The protein content in exosomes includes endosomal, plasma, and nuclear proteins. Proteins enriched in exosomes include those relevant for individual exosomal biogenesis pathways and for exosome secretion. Factors found in exosomes of different cell types include: TSG101, Alix, Rab GTPases, heat shock proteins (HSP70, HSP90), integrins, tetraspanins (CD9, CD63, CD81) and MHC class II proteins. A number of reviews have described the protein and lipid composition of exosomes, and various databases, including ExoCarta (http://www.exocarta.org/) and Vesiclepedia (http://microvesicle.org/), herein included by reference in their entirety, have cataloged the protein, lipid, and RNA content of exosomes. In addition, exosomes can contain genetic material such as mRNA, long noncoding RNA (lncRNA), microRNA (miRNA) and even double-stranded DNA. Moreover, the composition of exosomes can be different from the cells of their origin due to the selective sorting of cargo into exosomes.

B. TUMORIGENESIS

Exosomes derived from malignant cells have shown the potential to induce cell transformation. They can also affect other cells in the heterogeneous tumor population, and be involved in the transfer of metastatic capacity. For instance, exosomes released by malignant breast cancer cells are taken up by less malignant tumor cells located within the same tumor, and thereby promote their migratory and metastatic potential.

In addition, exosomal miRNA from cancer cells can contribute to tumorigenesis. Both mature miRNA and pre-miRNA transcripts are present in exosomes along with other components of the machinery for miRNA biogenesis such as DICER, TRBP, and AGO2. Melo et al demonstrated that exosomes derived from breast cancer cells and sera of patients with breast cancer could instigate nontumorigenic epithelial cells to form tumors. Although much of the evidence has emanated from in vitro studies, the exchange of exosomes between tumor cells was recently demonstrated in vivo in a study which combined high-resolution imaging with a Cre-LoxP system. Exosomes derived from malignant breast cancer cells are taken up by less malignant tumor cells within the same tumor and distant tumors. The mRNA content in the exosomes promotes migratory behavior and metastatic capacity of the recipient cancer cells.

CAFs are major components of the tumor microenvironment. Exosomes derived from CAFs can mediate horizontal transfer of miRNAs and proteins to affect breast cancer progression. Webber et al demonstrated exosomal TGF-β1 participated in the activation of myofibroblast, which is a rate-limiting step in cancer progression. Hoshino et al reported the effect of cancer cell-derived exosomes on multiple steps of invadopodia life cycle, including invadopodia formation and stabilization. Releases of exosomal proteinases were also shown to enhance degradation of extracellular matrix (ECM) associated with invadopodia maturation. By inducing ECM degradation, cancer cell-derived exosomes promote tumor cell invasiveness and motility. Of note, Lazar et al showed that adipocytes secrete exosomes in abundance, which are then taken up by tumor cells, leading to increased migration and invasion. Collectively, these findings point towards a role of exosomes in tumorigenesis.

C. TUMOR GROWTH

The effect of tumor-derived exosomes on tumor growth has been widely reported in the past decade. Exosomes from sera of glioblastoma patients are enriched with EGFRvIII mRNA. The proliferation potential of recipient cells was shown to be greatly enhanced on co-culture with EGFRvIII-containing exosomes. Peinado et al demonstrated that melanoma exosomes containing MET oncoprotein can support tumor growth as well. In colorectal cancer, tumor-derived exosomes are enriched in cell cycle-related mRNAs, promoting proliferation of endothelial cells and tumor growth. Another study by Kogure et al showed that exosomes derived from hepatocellular carcinoma (HCC) cells can modulate TAK1 expression and associated signaling pathways to enhance cell growth in recipient cells. In addition, exosomes from stromal cells can promote proliferation through other signaling pathways. For instance, Au Yeung et al demonstrated that CAF secreted exosomes to regulate survival and proliferation of pancreatic cancer cells, thus may serve as a potential target for overcoming resistance of chemotherapy. Similarly, miRNA-21 enriched in CAF exosomes may profoundly impact ovarian cancer growth by suppressing apoptosis through binding to APAF1. Zhang et al reported that the loss of exosomal miRNA-320a from CAFs contributed to HCC proliferation.

While the majority of research evidence pertains to the pro-tumorigenic effect of tumor-derived exosomes, the function of stromal-derived exosomes may differ from, and, perhaps be opposite to that of cancer exosomes. The presence of a competitive biological process was well-characterized in multiple myeloma (MM). Bone marrow mesenchymal stromal cells (BM-MSCs) from patients with MM were shown to have a high expression of oncogenic proteins, which facilitated the growth of MM cells in vivo. In contrast, the level of miRNA-15a, a known suppressor of MM growth, was significantly higher in exosomes derived from BM-MSCs of normal individuals, thus suggesting a tumor suppressive role of MSC-derived miRNA-15a. Thus, exosomes from cancer and stromal cells may modulate tumor growth.

D. ANGIOGENESIS

Angiogenesis is a fundamental physiological process involved in wound healing and carcinogenesis. Angiogenesis involves a close interaction between endothelial cells and their surrounding microenvironment. Uptake of exosomes by the endothelial cells (ECs) stimulates angiogenesis. Several groups reported the pro-angiogenic effect of tumor-derived exosomes on endothelial cells in various types of cancers such as glioblastoma, leukemia, multiple myeloma, melanoma, ovarian cancer and breast cancer. In a study by Skog et al, angiogenic-protein rich exosomes released from glioblastoma tumor cells were shown to stimulate tubule formation in ECs. Gopal et al demonstrated communication between oncogenic cells undergoing epithelial-mesenchymal transition (EMT) and endothelial cells via exosomes containing Rac1/PAK2 proteins as the angiogenic promoters.

Some miRNAs found in exosomes are thought to be specifically involved in tumor angiogenesis. For example, in colorectal cancer, miRNA-9 in tumor-derived exosomal vesiculars showed pro-angiogenic effects through inhibiting the expression of suppression of cytokine signaling 5 (SOCS5), promoting the migration of endothelial cells. In addition, miRNA-210 has been observed to suppress the expression of specific genes in endothelial cells, resulting in enhanced pro-angiogenic activity. Despite the direct pro-angiogenic effect of tumor-derived exosomes on endothelial cells, tumor-derived exosomes also demonstrated indirect effects on other stromal cells, such as CAFs. For example, in leukemia, tumor-derived exosomes induced a CAF phenotype in stromal cells in the surrounding microenvironment, hence leading to increased expression of pro-angiogenic factors in tumor. Of note, transfer of miRNA-125a from MSC-derived exosomes to ECs promoted angiogenesis, both in vitro and in vivo. The effect of tumor-derived exosomes on vascular remodeling may affect both tumor growth and metastasis. For instance, melanoma-derived exosomes can induce vascular leak at pre-metastatic sites and can also reprogram bone marrow progenitors towards a pro-vasculogenic phenotype. Exosomes have been shown to contain different kinds of angiogenic factors; it is contemplated that such exosomes may alter epigenetic signatures in cells taking up such exosomes in order to determine their contribution to cancer development.

Thus epigenetic effects of exosomes upon gene expression is contemplated. In some embodiments, the capability of exosomes from different types of source cells, including but not limited to noncancerous cells, pre-cancerous, and cancerous cells, etc., to change epigenetic profiles (signatures) are evaluated (assessed). Source cells for input exosomes, in turn including but are not limited to, untreated cells, cells treated in vivo or in vitro within a microfluidic device as described herein, are contemplated for use testing epigenetic changes associated with uptake of these exosomes. In some embodiments, epigenetic signatures of exosomes include measuring amounts of and/or function of enzymes within the exosome capable of inducing epigenetic events.

In some embodiments, source cells of input exosomes are cells treated with an agent as described herein.

E. TUMOR IMMUNE ESCAPE

Currently available evidence indicates a dual role of exosomes in mediating crosstalk between immune cells and cancer cells. On the one hand, various immune-stimulatory genes, such as mesothelin, and carcinoembryonic antigen (CEA), are packed in tumor-derived exosomes. On the other hand, several recent studies suggested that the cancer cells utilized exosomes containing nucleic acids and proteins to enact an immune escape.

An earlier study showed that the dendritic cell (DC)-derived exosomes stimulated an antitumor immune response. However, recent research showed tumor-derived exosomes may aid in immune evasion by impairing differentiation and maturation of dendritic cells, which changed their role from effective antigen presenting cells into negative modulators of immune response.

Exosomes may also play a role in the biology of cytotoxic T cells and regulatory T cells. For instance, in nasopharyngeal carcinoma, tumor-derived exosomes impaired T cell proliferation, differentiation and cytokine secretion in vivo and in vitro. The effect appeared to be mediated via downregulation of the MAPK1 and JAK/STAT pathways by exosomal miRNAs. Clayton et al demonstrated an exosome-mediated mechanism that skewed the IL-2 responsiveness in favor of regulatory T cells and away from cytotoxic cells; this coordinated effect on cellular immunity strongly implicates the role of tumor-derived exosomes in immune escape by tumor cells.

Tumor-associated macrophages (TAMs) are currently the most widely studied inflammatory cell component of tumor microenvironment (TME) and may also be activated by tumor-derived exosomes. For instance, Fabbri et al identified a new mechanism of communication between TAMs and cancer cells via exosomal miRNAs. Specifically, exosomal miRNA-21 and miRNA-29a were recruited in the TME by TAMs and bind to their Toll-like receptor 8, triggering the Nuclear factor kappa-light-chain-enhancer of activated B cells (NF-κB) pathway and the secretion of interleukin-6 (IL-6).

Moreover, exosomes derived from human prostate cancer cells were shown to express ligands for NKG2D, which induced downregulation of NKG2D in NK cells and impaired NK cell cytotoxic function. Ying et al demonstrated that ovarian tumor-derived exosomes play a crucial role in regulating the polarization of tumor-promoting M2 macrophages.

While the above examples demonstrate that tumor-derived exosomes may suppress the immune response, it appears that exosomes derived from immune cells can also influence the cancer cells. For instance, exosomes from activated $CD8^+$ T cells increased tumor immunogenicity by activating ERK and NF-κB signaling, which can promote the metastatic potential of tumor cells. Collectively, these studies suggest that exosomes may mediate immunosuppression in tumor-bearing host in different ways.

F. DRUG RESISTANCE

Drug resistance has long been a major obstacle in the management of cancers. Recently, exosomes are of great interest in drug resistance studies. Drug-resistant cancer cells may spread resistance to hitherto sensitive ones by releasing exosomes; such effects could be partly attributed to the intercellular transfer of specific proteins, miRNAs, and even long noncoding RNAs.

Stromal cells were found to initiate cross-talk with cancer cells via exosomes. CAF-derived exosomes were shown to contribute to proliferation and chemoresistance of pancreatic cancer cells. Boelens et al demonstrated the transfer of exosomes from stromal cells to breast cancer cells activated antiviral retinoic acid-inducible gene 1 enzyme (RIG-1) signaling to regulate the expansion of therapy-resistant tumor-initiating cells. Further study by Au Yeung et al showed that in ovarian cancer, exosomal transportation of CAF-derived miRNA-21 conferred paclitaxel resistance in ovarian cancer cells through targeting APAF1. Moreover, a recent study by Sun et al demonstrated that suppression of miRNA-122 resulted in taxol resistance by upregulating Septin-9 in HCC. Qu et al reported that exosome-transmitted LncRNA promoted Sunitinib resistance in renal cancer by acting as a competing endogenous RNA for miRNA-34 and miRNA-449 to promote AXL and c-MET expression.

In addition, exosomes may also affect tumor chemotherapy by mediating drug efflux. Shedden et al found that doxorubicin can be encapsulated and exported by tumor-derived exosomes. Moreover, exosomes may play a role in lowering the therapeutic effect of antibodies by modulating their binding to cancer cells. For instance, breast cancer cell-derived exosomes were shown to have a high expression of HER2 which interfered with the activity of the monoclonal antibody trastuzumab in vitro. Collectively, exosomes derived from both cancer cells and stromal cells can contribute to the development of chemoresistance in tumor cells.

G. METASTASIS

Exosomes not only affect cells in the location where they are produced, but may also influence cells in distant tissues. Exosomes are involved in both the initiation of metastasis and the preparation of a pre-metastatic niche. Exosomes may assist cancer cells in acquiring migratory and invasive properties through EMT. For instance, Aga et al demonstrated that treatment of EBV-negative cells with LMP1-exosomes increases migration and invasiveness of nasopharyngeal cancer cells in functional assays, which correlates with the phenotype associated with EMT. Recently, an in vitro imaging experiment also showed the importance of exosome-mediated exchange of molecules for metastasis among tumor cells.

The pre-metastatic niche is a prerequisite of tumor metastasis. Exosomes derived from the primary tumor can act as potential mediators for priming the pre-metastatic niche. Pancreatic tumor-derived exosomes enriched in macrophage migration inhibitory factors recruited macrophages to establish pre-metastatic niche in the liver, which resulted in increased hepatic macrometastatic burden. Moreover, breast cancer cell-derived exosomal miRNA-122 was shown to suppress glucose uptake by niche cells to promote metastasis, both in vitro and in vivo. Liu et al recently reported the Toll-like receptor 3 (TLR3) mediated crosstalk between pulmonary epithelial cells and tumor exosomal RNAs involved with the initiation of neutrophil recruitment and lung metastatic niche formation. In addition, tumor-derived exosomes were shown to express unique integrins which prepare the pre-metastatic niche by fusing with resident cells and by activating Src phosphorylation and pro-inflammatory S100 expression at the eventual site of metastasis.

Recently, Bliss et al reported the nature of regulatory interactions between breast cancer cells and MSC mediated by exosomes and MSC-derived exosomes may stimulate cycling quiescence and early breast cancer dormancy in bone marrow. Moreover, tumor-derived exosomes carrying miRNA-181c may trigger the breakdown of blood-brain-barrier (BBB) to promote brain metastasis. Zhang et al demonstrated that astrocyte-derived exosomes mediate intercellular transfer of PTEN-targeting miRNAs to metastatic tumor cells, which results in PTEN silencing in these tumor cells. This loss of PTEN expression leads to increased chemokine CCL2 level that recruits myeloid cells to reciprocally promote brain metastasis. These findings show that the intercellular crosstalk mediated by exosomes is a crucial mechanism for tumor metastasis.

H. EXOSOMES AS CANCER BIOMARKERS

Exosomes have been detected in nearly all kinds of body fluids, including blood, urine, saliva, amniotic fluid, cerebrospinal fluids, bile, ascites, tears, breast milk and semen (9,92-96). Almost all types of cells can secrete exosomes containing specific proteins, lipids, RNA and even DNA into their microenvironment and circulation (97).

The discovery of elevated level of exosomal miRNAs in the plasma of certain cancer patients was the first indication of the potential use of circulating exosomes as cancer biomarkers. Taylor et al reported that circulating exosomal miRNAs from patients with ovarian cancer were significantly distinct from profiles observed in benign disease and healthy volunteers (98). Microarray analyses of miRNAs derived from circulating exosomes derived from 88 patients with primary colorectal cancer (CRC) and 11 healthy donors, revealed significantly higher levels of 7 miRNAs in the former (99). Recently, Zhu et al demonstrated that the levels of miRNA-19a-3p, miRNA-21-5p and miRNA-425-5p were significantly elevated in exosomes from colorectal cancer patients' serum samples (100).

In addition, Li et al reported that LncRNA can be detected in plasma, and one of the possible mechanisms of its stable existence in blood was its protection by exosomes (101). Li et al recently reported that high levels of exosomal circular RNAs (circRNAs) and serum exosomal circRNAs can distinguish cancer patients from healthy individuals (102).

Proteins associated with tumor-derived exosomes are also seen as potential biomarkers. Exosomes double-positive for CD63 or caveolin-1 and Rab-5b were significantly increased in plasma from melanoma patients as compared to that from healthy donors. Noteworthy, Melo et al showed that Glypican-1-positive circulating exosomes was a reliable biomarker for early detection of pancreatic cancer, with superior prognostic value than CA19-9. Similarly, in a study by Lea et al provided proof-of-concept data that supported the high diagnostic power of phosphatidylserine-positive exosomes detected in the blood of women with ovarian malignancies.

For prognostic evaluation, circulating exosomes may enhance the stratification of cancer patients with high-risk factors. Manier et al reported that two circulating exosomal miRNAs, namely let-7b and miRNA-18a, improved survival prediction in patients with multiple myeloma. Similar results have been found in multiple types of cancers, including non-small cell lung cancer, esophageal squamous cell carcinoma, colorectal cancer, HCC and nasopharyngeal carcinoma.

For monitoring treatment response, exosomes have been demonstrated to accurately reflect the levels of proteins and mRNAs in parental cells throughout treatment and therefore can serve as potential biomarker of chemotherapy response. Skog et al identified a protein signature in circulating exosomes linked with clinical stages of melanoma patients. As a predictor of TKI treatment response, exosomal EGFRvIII splice variant was detectable in the serum of glioblastoma multiforme patients, but not the 30 matched controls.

Additionally, some newly developed technologies exist to sort and enrich exosomes. Wunsch et al recently demonstrated that nanoscale deterministic lateral displacement pillar arrays, an efficient technology to sort exosomes, may open up the potential for on-chip separation and diagnosis.

Collectively, the development of exosome-based novel biomarkers may provide benefits to cancer patients in a wide variety of ways (Table 3).

TABLE 3

Exosomes from distinct body fluids of cancer patients as biomarkers.

| Exosomal cargos | Cancer types | Clinical value | Biofluids | Reference |
| --- | --- | --- | --- | --- |
| Phosphatidylserine | Ovarian cancer | Elevated level of phosphatidylserine positive exosomes in ovarian cancer patients than healthy controls | Plasma | Matsumoto et al: Quantification of plasma exosome is a potential prognostic marker for esophageal squamous cell carcinoma. Oncol Rep 36: 2535-2543, 2016. |
| TRPC5 | Breast cancer | Elevated level of exosomal TRPC5 in cancer patients and higher levels may predict poorer progress | Plasma | Wang et al: Increasing circulating exosomes-carrying TRPC5 predicts chemoresistance in metastatic breast cancer patients. Cancer Sci 108: 448-454, 2017. |
| miRNA-1246, 21 | Breast cancer | Elevated levels of these two exosomal miRNAs in breast cancer patients than healthy controls | Plasma | Hannafon et al: Plasma exosome microRNAs are indicative of breast cancer. Breast Cancer Res 18:90, 2016. |
| CRNDE-h | Colorectal cancer | Elevated level of exosomal CRNDE-h in cancer patients and higher levels predict poorer progress | Plasma | Liu et al: Exosomal long noncoding RNA CRNDE-h as a novel serum-based biomarker for diagnosis and prognosis of colorectal cancer. Oncotarget 7: 85551-85563, 2016. |
| miRNA-4772-3p | Colon cancer | Lower level of exosomal miRNA-4772-3p predict tumor recurrence | Serum | Liu et al: Serum exosomal miR-4772-3p is a predictor of tumor recurrence in stage II and III colon cancer. Oncotarget 7: 76250-76260, 2016. |
| miRNA-19a-3p, 21-5p, 425-5p | Colorectal cancer | Elevated levels of the three exosomal miRNAs in colorectal cancer patients than healthy controls | Serum | Zhu et al: A panel of microRNA signature in serum for colorectal cancer diagnosis. Oncotarget 8: 17081-17091 2017. |
| miRNA-17-92a | Colorectal cancer | Elevated level in colorectal cancer patients and higher levels may predict poorer progress | Serum | Matsumura et al: Exosomal microRNA in serum is a novel biomarker of recurrence in human colorectal cancer. Br J Cancer 113: 275-281, 2015. |
| miRNA-19-3p, 21-5p, 221-3p | Lung adenocarcinoma | Elevated levels of the three miRNAs in lung adenocarcinoma patients than healthy controls | Plasma | Zhou et al: A six-microRNA panel in plasma was identified as a potential biomarker for lung adenocarcinoma diagnosis. Oncotarget 8: 6513-6525, 2017. |
| miRNA-302a, 302-c, 126 | Non-small cell lung cancer (NSCLC) | Elevated levels of the three miRNAs in NSCLC patients than healthy controls | Plasma/ Broncho-alveolar lavage | Rodriguez et al: Different exosome cargo from plasma/bronchoalveolar lavage in non-small-cell lung cancer. Genes Chromosomes Cancer 53: 713-724, 2014. |
| EML4-ALK fushion | NSCLC | EML4-ALK fushion transcripts have been identified in the exosomal RNA of NSCLC patients | Plasma | Brinkmann et al: Exosomal RNA based liquid biopsy detection of EML4-ALK in plasma from NSCLC patients. In: Proc Int Assoc IALSC, Denver, CO, 2016. |
| Glypican-1 | Pancreatic cancer | Higher level of Glypican-1 positive exosomes in patients with early- and late-stage pancreatic cancer than healthy controls | Serum | Liu et al: Circulating exosomal microRNAs as prognostic biomarkers for non-small-cell lung cancer. Oncotarget 8:13048-13058, 2017. |

TABLE 3-continued

Exosomes from distinct body fluids of cancer patients as biomarkers.

| Exosomal cargos | Cancer types | Clinical value | Biofluids | Reference |
| --- | --- | --- | --- | --- |
| miRNA-1246, 4644, 3976, 4306 | Pancreatic cancer | Elevated levels of these 4 exosomal miRNAs in pancreatic cancer patients compared to healthy controls | Serum | Madhavan et al: Combined evaluation of a panel of protein and miRNA serum-exosome biomarkers for pancreatic cancer diagnosis increases sensitivity and specificity. Int J Cancer 136: 2616-2627, 2015. |
| LncRNA-p21 | Prostate cancer | Elevated level of exosomal lncRNA-p21 in patients with prostate cancer than healthy controls | Plasma | Isin, et al: Exosomal lncRNA-p21 levels may help to distinguish prostate cancer from benign disease. Front Genet 6: 168, 2015. |
| miRNA-21, 375 | Prostate cancer | Elevated levels of urinary exosomal miRNA-21 and miRNA-375 in patients with prostate cancer than healthy controls | Urine | (133) Huang, et al: A novel serum microRNA signature to screen esophageal squamous cell carcinoma. Cancer Med 6: 109-119, 2017. |
| miRNA-375 1290 | Prostate cancer | Castration-resident prostate cancer patients with elevated levels of both exosomal miRNA-375 and miRNA-1290 may predict poorer progress | Serum | Mirzaei, et al: State of the art in microRNA as diagnostic and therapeutic biomarkers in chronic lymphocytic leukemia. J Cell Physiol: Jan. 13, 2017 |
| miRNA-718 | HCC | Lower level of exosomal miRNA-718 in patients with HCC patients with recurrence after liver transplantation than those without recurrence | Serum | Sugimachi, et al: Identification of a bona fide microRNA biomarker in serum exosomes that predicts hepatocellular carcinoma recurrence after liver trans-plantation. Br J Cancer 112: 532-538, 2015. |
| miRNA-21 | HCC | Elevated levels of these three exosomal mircroRNAs in HCC cancer patients than healthy controls | Serum | Wang, et al: Expression of serum exosomal microRNA-21 in human hepatocellular carcinoma. Biomed Res Int 2014: 864894, 2014. |
| miRNA-211, 222, 224 | HCC | Elevated levels of these three exosomal mircroRNAs in HCC cancer patients than healthy controls | Serum | Sohn, et al: Serum exosomal microRNAs as novel biomarkers for hepatocellular carcinoma. Exp Mol Med 47: e184, 2015. |
| CD34 | Acute myeloid leukemia (AML) | Higher level of CD34 positive exosomes in AML patients than healthy control | Plasma | Hong, et al: Isolation and characterization of CD34 blast-derived exosomes in acute myeloid leukemia. PLoS One 9: e103310, 2014. |
| Let-7b, miRNA-18a | MM | Elevated expression in cancer patients and higher levels of these two exosomal miRNAs may predict poorer progress | Serum | Manier, et al: Prognostic role of circulating exosomal miRNAs in multiple myeloma. Blood 129: 2429-2436, 2017. |

Thus in some embodiments, exosomes collected from body fluids may find use in determining epigenetic signatures, including but not limited to within the exosomes, exosomal effects upon signatures in cells that take up such exosomes, etc. Such use is not limited to cancer patients, including but not limited to patients having other diseases, and further similar types of evaluations may be done with samples contacted or treated as described herein with a range of exposures.

In summary, cancer cells communicate with surrounding and distant cells via exosomes. Exosomes constitute a bi-directional interaction network that mediates the intercellular cross talk between cancer cells and the microcellular environment to promote cancer development, progression, metastasis, and drug resistance. However, most pieces of the aforementioned findings are gathered from cell culture experiments. Therefore, it is vital to substantiate these results in more rigorous in vitro settings, such as with microfluidic devises such as described herein. Moreover, exosomes released by cancer cells and TME are highly heterogeneous. But there are few reports explaining the role of each of these subtypes. The difficulties in elucidating the roles of specific exosomes include lack of unique molecules to distinguish each exosome subtype and appropriate exosomes isolation methods. Future technical advances may lead to significant progress in the understanding of the heterogeneity of exosomes.

Exosomes were proven to be stable carriers of genetic materials, and been nominated as promising tumor biomarkers for cancer diagnosis and prognosis. Moreover, during cancer treatment, exosomes may switch their contents and may therefore exhibit traits for the monitoring of therapeutic efficiency. Furthermore, as vectors for drugs and tumor vaccines, exosome-based delivery is rigorously evaluated as an emerging therapeutic strategy for cancer. Additional studies are much needed to better elucidate their role and mechanism of action in cancer to reduce the risk of off-target effects and therapeutic failures. The several aforementioned results still require further validation in clinical settings, especially in independent prospective cohorts.

Altogether, with the emergence of precision medicine, future studies on exosomes should not only emphasize their roles in cancer biology, but may also open new avenues for cancer diagnostics and therapeutics.

I. REFERENCES RELATING TO EXOSOMES, HEREIN INCORPORATED BY REFERENCE IN THEIR ENTIRETY

9. Zhang X, Yuan X, Shi H, Wu L, Qian H, Xu W. Exosomes in cancer: Small particle, big player. J Hematol Oncol. 2015; 8:83.
80. Chen Y, Wang L, Zhu Y, Chen Z, Qi X, Jin L, Jin J, Hua D, Ma X. Breast cancer resistance protein (BCRP)-containing circulating microvesicles contribute to chemoresistance in breast cancer. Oncol Lett. 2015; 10:3742-3748.
81. Richards K E, Zeleniak A E, Fishel M L, Wu J, Littlepage L E, Hill R. Cancer-associated fibroblast exosomes regulate survival and proliferation of pancreatic cancer cells. Oncogene. 2016; 36:1770-1778. doi: 10.1038/onc.2016.353.
82. Boelens M C, Wu T J, Nabet B Y, Xu B, Qiu Y, Yoon T, Azzam D J, Victor Twyman-Saint C, Wiemann B Z, Ishwaran H, et al. Exosome transfer from stromal to breast cancer cells regulates therapy resistance pathways. Cell. 2014; 159:499-513.
83. Shedden K, Xie X T, Chandaroy P, Chang Y T, Rosania G R. Expulsion of small molecules in vesicles shed by cancer cells association with gene expression and chemosensitivity profiles. Cancer Res. 2003; 63:4331-4337.
84. Ciravolo V, Huber V, Ghedini G C, Venturelli E, Bianchi F, Campiglio M, Morelli D, Villa A, Mina P D, Menard S, et al. Potential role of HER2-overexpressing exosomes in countering trastuzumab-based therapy. J Cell Physiol. 2012; 227:658-667.
85. Aga M, Bentz G L, Raffa S, Torrisi M R, Kondo S, Wakisaka N, Yoshizaki T, Pagano J S, Shackelford J. Exosomal HIF1α supports invasive potential of nasopharyngeal carcinoma-associated LMP1-positive exosomes. Oncogene. 2014; 33:4613-4622.
86. Costa-Silva B, Aiello N M, Ocean A J, Singh S, Zhang H, Thakur B K, Becker A, Hoshino A, Mark M T, Molina H, et al. Pancreatic cancer exosomes initiate pre-metastatic niche formation in the liver. Nat Cell Biol. 2015; 17:816-826.
87. Liu Y, Gu Y, Han Y, Zhang Q, Jiang Z, Zhang X, Huang B, Xu X, Zheng J, Cao X. Tumor exosomal RNAs promote lung pre-metastatic niche formation by activating alveolar epithelial TLR3 to recruit neutrophils. Cancer Cell. 2016; 30:243-256.
88. Hoshino A, Costa-Silva B, Shen T-L, Rodrigues G, Hashimoto A, Tesic Mark M, Molina H, Kohsaka S, Di Giannatale A, Ceder S, et al. Tumour exosome integrins determine organotropic metastasis. Nature. 2015; 527: 329-335.
89. Bliss S A, Sinha G, Sandiford O A, Williams L M, Engelberth D J, Guiro K, Isenalumhe L L, Greco S J, Ayer S, Bryan M, et al. Mesenchymal stem cell-derived exosomes stimulate cycling quiescence and early breast cancer dormancy in bone marrow. Cancer Res. 2016; 76:5832-5844.
90. Tominaga N, Kosaka N, Ono M, Katsuda T, Yoshioka Y, Tamura K, Lötvall J, Nakagama H, Ochiya T. Brain metastatic cancer cells release microRNA-181c-containing extracellular vesicles capable of destructing blood-brain barrier. Nat Commun. 2015; 6:6716.
91. Zhang L, Zhang S, Yao J, Lowery F J, Zhang Q, Huang W-C, Li P, Li M, Wang X, Zhang C, et al. Microenvironment-induced PTEN loss by exosomal microRNA primes brain metastasis outgrowth. Nature. 2015; 527: 100-104.
92. Raposo G, Stoorvogel W. Extracellular vesicles: Exosomes, microvesicles, and friends. J Cell Biol. 2013; 200:373-383.
93. Keller S, Ridinger J, Rupp A K, Janssen J W, Altevogt P. Body fluid derived exosomes as a novel template for clinical diagnostics. J Transl Med. 2011; 9:86.
94. Pisitkun T, Shen R-F, Knepper M A. Identification and proteomic profiling of exosomes in human urine. Proc Natl Acad Sci USA. 2004; 101:13368-13373.
95. Gallo A, Tandon M, Alevizos I, Illei G G. The majority of microRNAs detectable in serum and saliva is concentrated in exosomes. PLoS One. 2012; 7:e30679.
96. Lau C, Kim Y, Chia D, Spielmann N, Eibl G, Elashoff D, Wei F, Lin Y-L, Moro A, Grogan T, et al. Role of pancreatic cancer-derived exosomes in salivary biomarker development. J Biol Chem. 2013; 288:26888-26897.
97. Kosaka N, Yoshioka Y, Fujita Y, Ochiya T. Versatile roles of extracellular vesicles in cancer. J Clin Invest. 2016; 126:1163-1172.
98. Taylor D D, Gercel-Taylor C. MicroRNA signatures of tumor-derived exosomes as diagnostic biomarkers of ovarian cancer. Gynecol Oncol. 2008; 110:13-21. doi: 10.1016/j.ygyno.2008.04.033.
99. Ogata-Kawata H, Izumiya M, Kurioka D, Honma Y, Yamada Y, Furuta K, Gunji T, Ohta H, Okamoto H, Sonoda H, et al. Circulating exosomal microRNAs as biomarkers of colon cancer. PLoS One. 2014; 9:e92921.
100. Zhu M, Huang Z, Zhu D, Zhou X, Shan X, Qi L W, Wu L, Cheng W, Zhu J, Zhang L, et al. A panel of microRNA signature in serum for colorectal cancer diagnosis. Oncotarget. 2017; 8:17081-17091.
101. Li Q, Shao Y, Zhang X, Zheng T, Miao M, Qin L, Wang B, Ye G, Xiao B, Guo J. Plasma long noncoding RNA protected by exosomes as a potential stable biomarker for gastric cancer. Tumour Biol. 2015; 36:2007-2012.
102. Li Y, Zheng Q, Bao C, Li S, Guo W, Zhao J, Chen D, Gu J, He X, Huang S. Circular RNA is enriched and stable in exosomes: A promising biomarker for cancer diagnosis. Cell Res. 2015; 25:981-984.
103. Logozzi M, De Milito A, Lugini L, Borghi M, Calabro L, Spada M, Perdicchio M, Marino M L, Federici C, Iessi E, et al. High levels of exosomes expressing CD63 and caveolin-1 in plasma of melanoma patients. PLoS One. 2009; 4:e5219.
104. Melo S A, Luecke L B, Kahlert C, Fernandez A F, Gammon S T, Kaye J, LeBleu V S, Mittendorf E A, Weitz J, Rahbari N, et al. Glypican-1 identifies cancer exosomes and detects early pancreatic cancer. Nature. 2015; 523: 177-182.

105. Lea J, Sharma R, Yang F, Zhu H, Ward E S, Schroit A J. Detection of phosphatidylserine-positive exosomes as a diagnostic marker for ovarian malignancies: A proof of concept study. Oncotarget. 2017; 8:14395-14407.
106. Manier S, Liu C J, Avet-Loiseau H, Park J, Shi J, Campigotto F, Salem K Z, Huynh D, Glavey S V, Rivotto B, et al. Prognostic role of circulating exosomal miRNAs in multiple myeloma. Blood. 2017; 129:2429-2436.
107. Liu Q, Yu Z, Yuan S, Xie W, Li C, Hu Z, Xiang Y, Wu N, Wu L, Bai L, et al. Circulating exosomal microRNAs as prognostic biomarkers for non-small-cell lung cancer. Oncotarget. 2017; 8:13048-13058.
108. Matsumoto Y, Kano M, Akutsu Y, Hanari N, Hoshino I, Murakami K, Usui A, Suito H, Takahashi M, Otsuka R, et al. Quantification of plasma exosome is a potential prognostic marker for esophageal squamous cell carcinoma. Oncol Rep. 2016; 36:2535-2543.
109. Sandfeld-Paulsen B, Aggerholm-Pedersen N, Baek R, Jakobsen K R, Meldgaard P, Folkersen B H, Rasmussen T R, Varming K, Jorgensen M M, Sorensen B S. Exosomal proteins as prognostic biomarkers in non-small cell lung cancer. Mol Oncol. 2016; 10:1595-1602.
110. Liu T, Zhang X, Gao S, Jing F, Yang Y, Du L, Zheng G, Li P, Li C, Wang C. Exosomal long noncoding RNA CRNDE-h as a novel serum-based biomarker for diagnosis and prognosis of colorectal cancer. Oncotarget. 2016; 7:85551-85563.
111. Ye S B, Zhang H, Cai T T, Liu Y-N, Ni J-J, He J, Peng J-Y, Chen Q-Y, Mo H-Y, Cui J, et al. Exosomal miR-24-3p impedes T-cell function by targeting FGF11 and serves as a potential prognostic biomarker for nasopharyngeal carcinoma. J Pathol. 2016; 240:329-340.
112. Wu Z, Zeng Q, Cao K, Sun Y. Exosomes: Small vesicles with big roles in hepatocellular carcinoma. Oncotarget. 2016; 7:60687-60697.
113. Hegi M E, Diserens A-C, Gorlia T, Hamou M-F, de Tribolet N, Weller M, Kros J M, Hainfellner J A, Mason W, Mariani L, et al. MGMT gene silencing and benefit from temozolomide in glioblastoma. N Engl J Med. 2005; 352:997-1003.
114. Shao H, Chung J, Lee K, Balaj L, Min C, Carter B S, Hochberg F H, Breakefield X O, Lee H, Weissleder R. Chip-based analysis of exosomal mRNA mediating drug resistance in glioblastoma. Nat Commun. 2015; 6:6999.
115. Wunsch B H, Smith J T, Gifford S M, Wang C, Brink M, Bruce R L, Austin R H, Stolovitzky G, Astier Y. Nanoscale lateral displacement arrays for the separation of exosomes and colloids down to 20 nm. Nat Nanotechnol. 2016; 11:936-940.
116. Marleau A M, Chen C-S, Joyce J A, Tullis R H. Exosome removal as a therapeutic adjuvant in cancer. J Transl Med. 2012; 10:134.
117. Morse M A, Garst J, Osada T, Khan S, Hobeika A, Clay T M, Valente N, Shreeniwas R, Sutton M, Delcayre A, et al. A phase I study of dexosome immunotherapy in patients with advanced non-small cell lung cancer. J Transl Med. 2005; 3:9.
118. Escudier B, Dorval T, Chaput N, Andre F, Caby M-P, Novault S, Flament C, Leboulaire C, Borg C, Amigorena S, et al. Vaccination of metastatic melanoma patients with autologous dendritic cell (DC) derived-exosomes: Results of the first phase I clinical trial. J Transl Med. 2005; 3:10.
119. Tian Y, Li S, Song J, Ji T, Zhu M, Anderson G J, Wei J, Nie G. A doxorubicin delivery platform using engineered natural membrane vesicle exosomes for targeted tumor therapy. Biomaterials. 2014; 35:2383-2390.
120. Kim M S, Haney M J, Zhao Y, Mahajan V, Deygen I, Klyachko N L, Inskoe E, Piroyan A, Sokolsky M, Okolie O, et al. Development of exosome-encapsulated paclitaxel to overcome MDR in cancer cells. Nanomedicine (Lond) 2016; 12:655-664.
121. Katakowski M, Buller B, Zheng X, Lu Y, Rogers T, Osobamiro O, Shu W, Jiang F, Chopp M. Exosomes from marrow stromal cells expressing miR-146b inhibit glioma growth. Cancer Lett. 2013; 335:201-204.
122. Ono M, Kosaka N, Tominaga N, Yoshioka Y, Takeshita F, Takahashi R, Yoshida M, Tsuda H, Tamura K, Ochiya T. Exosomes from bone marrow mesenchymal stem cells contain a microRNA that promotes dormancy in metastatic breast cancer cells. Sci Signal. 2014; 7:ra63.
123. Pascucci L, Coccè V, Bonomi A, Ami D, Ceccarelli P, Ciusani E, Viganò L, Locatelli A, Sisto F, Doglia S M, et al. Paclitaxel is incorporated by mesenchymal stromal cells and released in exosomes that inhibit in vitro tumor growth: A new approach for drug delivery. J Control Release. 2014; 192:262-270.
124. Wang T, Ning K, Lu T X, Sun X, Jin L, Qi X, Jin J, Hua D. Increasing circulating exosomes-carrying TRPC5 predicts chemoresistance in metastatic breast cancer patients. Cancer Sci. 2017; 108:448-454.
125. Hannafon B N, Trigoso Y D, Calloway C L, Zhao Y D, Lum D H, Welm A L, Zhao Z J, Blick K E, Dooley W C, Ding W Q. Plasma exosome microRNAs are indicative of breast cancer. Breast Cancer Res. 2016; 18:90.
126. Liu C, Eng C, Shen J, Lu Y, Takata Y, Mehdizadeh A, Chang G J, Rodriguez-Bigas M A, Li Y, Chang P, et al. Serum exosomal miR-4772-3p is a predictor of tumor recurrence in stage II and III colon cancer. Oncotarget. 2016; 7:76250-76260.
127. Matsumura T, Sugimachi K, Iinuma H, Takahashi Y, Kurashige J, Sawada G, Ueda M, Uchi R, Ueo H, Takano Y, et al. Exosomal microRNA in serum is a novel biomarker of recurrence in human colorectal cancer. Br J Cancer. 2015; 113:275-281.
128. Zhou X, Wen W, Shan X, Zhu W, Xu J, Guo R, Cheng W, Wang F, Qi L W, Chen Y, et al. A six-microRNA panel in plasma was identified as a potential biomarker for lung adenocarcinoma diagnosis. Oncotarget. 2017; 8:6513-6525.
129. Rodriguez M, Silva J, López-Alfonso A, López-Muñiz M B, Peña C, Dominguez G, García J M, López-Gónzalez A, Méndez M, Provencio M, et al. Different exosome cargo from plasma/bronchoalveolar lavage in non-small-cell lung cancer. Genes Chromosomes Cancer. 2014; 53:713-724.
130. Brinkmann K, Carbone D P, Enderle D, Koestler T, Bentink S, Emenegger J, Spiel A, Mueller R, O'Neill V, Skog J, et al. Proc Int Assoc IALSC. Denver, CO: 2016. Exosomal RNA based liquid biopsy detection of EML4-ALK in plasma from NSCLC patients.
131. Madhavan B, Yue S, Galli U, Rana S, Gross W, Müller M, Giese N A, Kalthoff H, Becker T, Buchler M W, et al. Combined evaluation of a panel of protein and miRNA serum-exosome biomarkers for pancreatic cancer diagnosis increases sensitivity and specificity. Int J Cancer. 2015; 136:2616-2627.
132. Işin M, Uysaler E, Özgúr E, Köseoğlu H, Şanli Ö, Yücel Ö B, Gezer U, Dalay N. Exosomal lncRNA-p21 levels may help to distinguish prostate cancer from benign disease. Front Genet. 2015; 6:168.
133. Huang Z, Zhang L, Zhu D, Shan X, Zhou X, Qi L W, Wu L, Zhu J, Cheng W, Zhang H, et al. A novel serum microRNA signature to screen esophageal squamous cell carcinoma. Cancer Med. 2017; 6:109-119.
134. Mirzaei H, Fathullahzadeh S, Khanmohammadi R, Darijani M, Momeni F, Masoudifar A, Goodarzi M, Mardanshah O, Stanveng J, Jaafari M R, et al. State of the art in microRNA as diagnostic and therapeutic biomarkers in chronic lymphocytic leukemia. J Cell Physiol. 2017 January 13.
135. Sugimachi K, Matsumura T, Hirata H, Uchi R, Ueda M, Ueo H, Shinden Y, Iguchi T, Eguchi H, Shirabe K, et al. Identification of a bona fide microRNA biomarker in serum exosomes that predicts hepatocellular carcinoma recurrence after liver transplantation. Br J Cancer. 2015; 112:532-538.
136. Wang H, Hou L, Li A, Duan Y, Gao H, Song X. Expression of serum exosomal microRNA-21 in human hepatocellular carcinoma. Biomed Res Int. 2014.
137. Sohn W, Kim J, Kang S H, Yang S R, Cho J-Y, Cho H C, Shim S G, Paik Y-H. Serum exosomal microRNAs as novel biomarkers for hepatocellular carcinoma. Exp Mol Med. 2015.
138. Hong C S, Muller L, Boyiadzis M, Whiteside T L. Isolation and characterization of CD34 blast-derived exosomes in acute myeloid leukemia. PLoS One. 2014.

IV. Developmental Effects and Medical Implications of Epigenetic Alterations of Chromosomes and Genomic DNA; Including Erasure (Removal) of these Alterations.

Epigenomics also refers to DNA or chromatin modifications. In some cases, such modifications result in altered gene expression, e.g. resulting in expression of one gene or allele over another, resulting in altered RNA expression, etc. The following non-limiting examples describe additional embodiments for monitoring epigenetic changes, including but not limited to identifying changes in expression and function of enzymes, (e.g. histone acetyl transferases, histone deacetylases (HDACs), etc., inhibitory chemicals (compounds that inhibit one or more of epigenetic altering enzymes), stimulatory chemicals (compounds that result in the increased activity of one or more of epigenetic altering enzymes), chromosomal morphology (e.g. deletions, additions, etc.), etc.

A. How to Make a Queen Bee or Unmake a Queen Bee or Effects of Inhibiting Changes in Epigenetic Events (Marks).

Whether a larval honeybee becomes a worker or a queen depends on an epigenetic switch, and this switch seems to be "flipped" by royal jelly. But what is it about royal jelly that leads a larva that would otherwise grow up to be a worker, to instead become a queen? The answer lies in understanding that the individual chemical tags that are added to the histone tails of nucleosomes are constantly being revised by the cell. During development, acetyl tags are added to histone tails by enzymes called histone acetyl transferases (HAC). In turn, these acetyl tags may then be removed or "erased" by a second group of enzymes called histone deacetylases (HDACs). Both of these enzymes are present in most cells and this allows genes to be switched on or off over time, regulating cellular processes.

More Acetyl Tags Help Deliver Queen Bee Status.

Recently, researchers set out to identify compounds in royal jelly that could alter this process, and what they found was something known as an HDAC inhibitor. This was a relatively simple chemical compound that is present in royal jelly that stops the action of HDAC enzymes that normally remove acetyl tags from histones. This results in a build-up of acetyl tags in the cells of the bee embryos, and like the reduction in DNA-methyl groups described previously, this is thought to switch on genes involved with development of a queen. Without the HDAC inhibitor in the royal jelly, the larvae follow a "default" set of genetic instructions, including removal of certain acetyl tags from histones, to develop into worker bees.

HDAC inhibitors have a role in creating queen bees, but they are also part of a small but growing number of medically useful drugs that target epigenetic tags and which are useful in treating some kinds of cancer. Furthermore HDACs also have a role in the way our brains form memories, and novel drugs that affect histone acetylation may have a role in the future in treating memory impairment in elderly patients.

B. The Environment and Epigenetics.

Human history or natural phenomena may provide epigenetic changes that may be detected without a known base-line epigenetic signature, long after the initial induction event. One such example is what is known as the Dutch Hunger Winter. In the last year of the Second World War in Europe, a food embargo imposed by occupying German forces on the civilian population of the Netherlands resulted in a severe famine, coinciding with a particularly harsh winter. About 20,000 people died from starvation as rations dropped to below 1000 kilocalories per day. Despite the chaos of war, medical care and records remained intact allowing scientists to subsequently study the effect of famine on human health. What they found was that children who were in the womb during the famine experienced a life-long increase in their chances of developing various health problems compared to children conceived after the famine. The most sensitive period for this effect was the first few months of pregnancy. Thus, something appears to happen early in development in the womb that can affect the individual for the rest of their lives.

1. Epigenetic Effects can Sometimes Pass to Children and Grandchildren.

Even more surprisingly, some data seems to suggest that grandchildren of women who were pregnant during the Hunger Winter experience some of these effects. From what we have already discussed, this strongly suggests an epigenetic mechanism. In fact, research with the Dutch Hunger Winter families continues, and a recent study looking at a gene galled IGF2 found lower levels of the methyl tag in the DNA of this gene in individuals exposed to the famine before birth. Although IGF2 may not itself be involved in the increased risk of poor health in these people, it shows that epigenetic effects (i.e. reduction of the number of methyl tags on particular genes) that are produced before birth can last for many decades. Studies in animals have also found that the diet of the mother can have effects on her offspring. For example, feeding sheep a diet lacking the types of food required to make methyl groups leads to offspring with altered patterns of DNA methylation and which have higher than expected rates of certain health problems.

2. Imprinting (Epigenetic Signatures) and Medical Disorders.

The term "epigenetic" also refers to those characteristics that are propagated from cell to cell by some means other than base-pairing, which makes them different from classic Mendelian traits. Usually, we inherit two copies of a gene, one from each parent, and both copies actively shape how we develop. However, if one of those copies is epigenetically "turned off" and the remaining working gene is deleted or severely mutated, then a person can be debilitated. In this case, the person has a good copy of the needed gene, but this gene cannot act because it has been turned off by epigenetic mechanisms.

Angelmann and Prader-Willi syndromes are two distinct genetic conditions with different symptoms, both caused by loss of a part of chromosome 15. Children who inherit one copy of the gene deletion develop either Angelmann or Prader-Willi syndrome, despite inheriting a normal copy of the gene from their other parent. So how does the same mutation in one gene (loss of part of chromosome 15) lead to these two different conditions? The answer lies in the discovery that this particular piece of chromosome 15 also contains a number of genes that are imprinted (i.e. have certain epigenetic tags) controlling whether a paternal or a maternal copy of this gene are expressed. When the epigenetic tag turns off some of the paternal normal copies of genes, then the lack of the maternal deleted genes result in Angelman syndrome. The region of chromosome 15 that is involved in Angelman syndrome also contains another gene that is imprinted the other way. In this case, when the paternal contribution is lost, the result is a condition known as Prader-Willi syndrome (PWS).

IV. RNA (Gene) Expression Profiling Providing an Epigenetic Signature.

Gene expression profiling refers to measurement of the activity (expression) of thousands of genes at once, to create a global picture of cellular function. As one example, RNA-Seq (Illumina, Inc. 5200 Illumina Way, San Diego, CA 92122), provides information on the sequences of genes in addition to their expression level. Thus, gene expression (RNA) patterns, at the level of transcription, under specific circumstances of contact with an agent, pathogen, etc., in a specific cell may provide a global picture of cellular function relative to an epigenetic signature.

As one example, total RNA was extracted and used to generate biotin-labeled cRNA, e.g. using an Illumina Total-Prep RNA Amplification Kit (Ambion, Austin, TX). Biotin-labeled cRNA was then hybridized to Illumina HumanHT-12 whole genome expression beadchips (Illumina, San Diego, CA). The quality of the Illumina bead summary data was assessed using the Bioconductor package Lumi. Data preprocessing may include variance stabilization and quantile normalization. To eliminate potentially confounding effects of RNA quality on gene expression, residuals may be calculated from the regression analysis of RIN values on gene expression and used for statistical analysis and WGCNA network construction. Outlier values may then be removed for each gene within a group using Grubbs' test ($p<0.05$). Statistical analysis comparing alcoholic and control groups may be performed using the Bioconductor package Limma to carry out a Bayesian two-tailed t-test. A false discovery rate (FDR) for each list of significantly regulated genes with nominal P values $<0.05$ may be estimated using the method of Benjamini and Hochberg (1995). Our systems approach to prioritizing individual genes may be based on integration of nominal statistical significance, gene network information and functional relevance. Therefore, to avoid omitting true positives, all genes with nominal P values $<0.05$ may be considered. After initial data processing, microarray data from controls and test samples were used for network construction.

DETAILED DESCRIPTION OF INVENTION

The present invention relates to microfluidic fluidic devices, methods and systems for use in identifying epigenetic signatures in a range of sample types, e.g., cells established on a "chip" (including but not limited to single cell samples, cell populations, cell layers and whole tissues, such as a biopsy), immune cells, cfDNA, exosomes, and the like.

More specifically, in some embodiments, a microfluidic chip containing a sample is contacted with a test compound (e.g. DNA altering test compound, an RNA expression altering test compound, etc.) for use in providing a diagnostic epigenetic signature for that type of sample (or cell type) exposed to that specific test compound. In some embodiments, after contact with a test compound, effluent fluids (e.g. fluids exiting the "chip" that contacted the cells) are derived for testing as a "virtual blood draw." In some embodiments, epigenetic signatures include (but are not limited to) identifying specific combinations of modifications of chromosomes and specific modifications of DNA.

In preferred embodiments, a microfluidic device capable of bringing a sample in contact with a test agent, such as a chemical warfare agent, e.g. a chemical, a pathogen, etc., a drug, etc. is contemplated for use in providing an epigenetic signature. Although several types of Micro- and nanoscale devices were used for investigation of epigenetics and chromatin dynamics. As one example, a device is described in Aguilar and Gaighead, "Micro- and nanoscale devices for investigation of epigenetics and chromatin dynamics." Nat Nanotechnol. 8(10): 709-718 (2013), herein incorporated by reference in its entirety, however none of these devices are providing a microfluidic platform providing an in vitro simulation of in vivo exposures for altering epigenetic patterns. In fact, devices such as described in Aguilar and Gaighead, "Micro- and nanoscale devices for investigation of epigenetics and chromatin dynamics." Nat Nanotechnol. 8(10): 709-718 (2013), herein incorporated by reference in its entirety, are merely microfluidic assay platforms used for detecting epigenetic marks after such epigenetics occurred in living material, including but not limited to induced changes from exposure to an agent in vivo; or induced changes from exposure to exosomal contents, drugs, etc. in cells prior to placing cells on these assay chips. Furthermore, such assay platforms are not sampling devices. In contrast to the microfluidic devices described herein, wherein the signatures detected using samples in microfluidic devices as described herein, may occur on chip, as in untreated cells, with induced epigenetic changes occurring on-chip by on-chip cellular changes by on-chip exposures to agents for use in generating in vivo-like epigenetic associated signatures in vitro. In some embodiments, such epigenetic signatures obtained using microfluidic devices as described herein may further be used for diagnostic applications.

For methods related to testing for exposure to WMD, preferred embodiments of microfluidic devices include but are not limited to chips containing cell types such as skin, gastrointestinal, and pulmonary. In yet further embodiments related to testing for exposure to WMD, preferred connected organ systems related to aerosols include but are not limited to skin, blood, liver, pulmonary, etc.; preferred connected organ systems related to pathogens include but are not limited to skin, blood, gastrointestinal, and pulmonary, etc; while connected organ systems related to radiation include but are not limited to skin, blood, etc.

I. Microfluidic Chips, Devices and Systems.

Figure 9A:
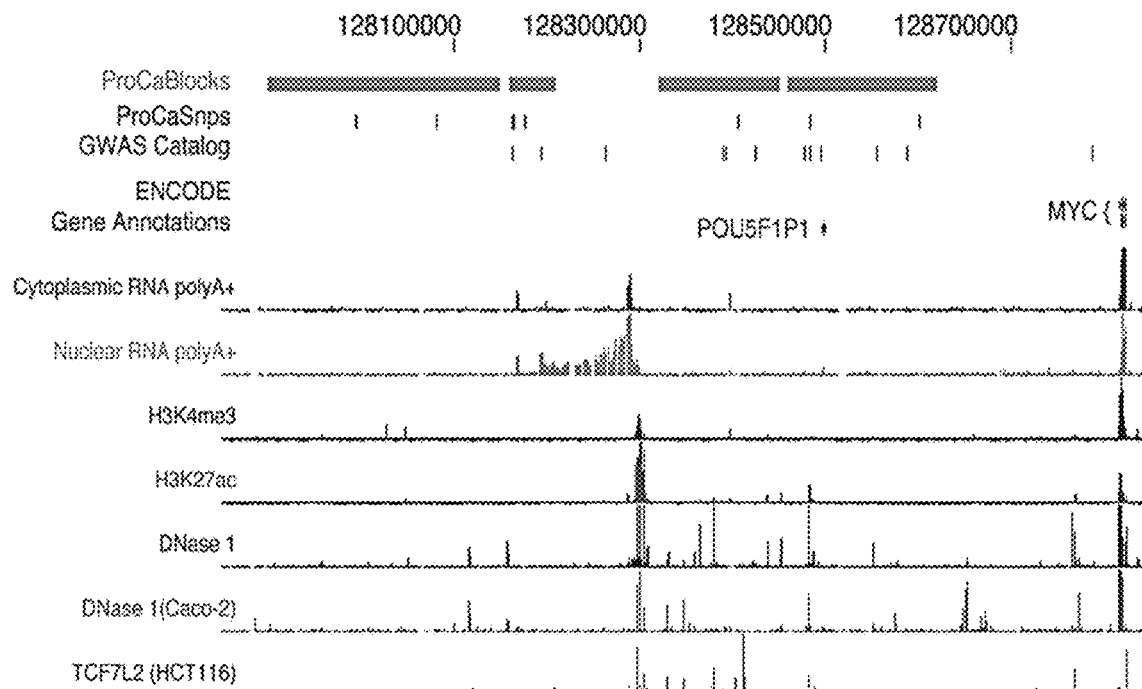
FIG. 9A shows examples of mapping RNAs, mapping of histone modifications (H3K4me3 and H3K27Ac), DNaseI hypersensitive sites in different cell lines then comparing results are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e1 001046 (2011). As exemplary embodiments: 1 Mb region including MYC and a gene desert upstream shows the linkage disequilibrium blocks and positions of SNPs associated with breast and prostate cancer, with both a custom track based on and the resident track from the GWAS catalog. ENCODE tracks include GENCODE gene annotations, results of mapping RNAs to high-density Affymetrix tiling arrays (cytoplasmic and nuclear polyA+RNA), mapping of histone modifications (H3K4me3 and H3K27Ac), DNaseI hypersensitive sites in liver and colon carcinoma cell lines (HepG2 compared to Caco 2), and occupancy by the transcription factor TCF7L2 in HCT116 cells.
Figure 9B:
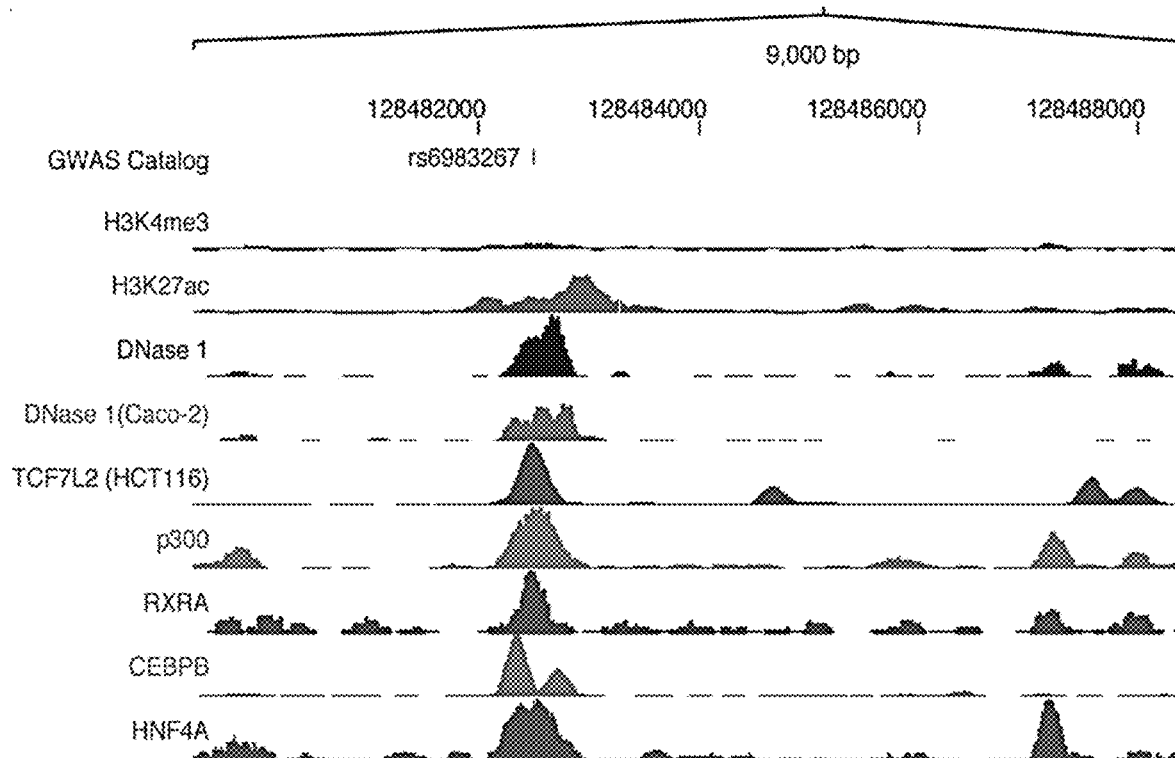
FIG. 9B shows an exemplary expanded view of a 9 kb region containing the cancer-associated SNP rs6983267 (shown on the top line), in addition to the histone modifications, DNaseI hypersensitive sites and factor occupancy described in FIG. 9A, are provided merely for illustrative purposes, see, for reference, ENCODE gene and transcript annotations; The ENCODE Project Consortium, A User's Guide to the Encyclopedia of DNA Elements (ENCODE). PLoS Biol 9(4): e 1 001046 (2011). As exemplary embodiments: the ENCODE tracks also show occupancy by the coactivator p300 and the transcription factors RXRA, CEBPB, and HNF4A. Except as otherwise noted in brackets, such as Caco-2 cell data, the ENCODE data shown here are from the liver carcinoma cell line HepG2.
Figure 10A:
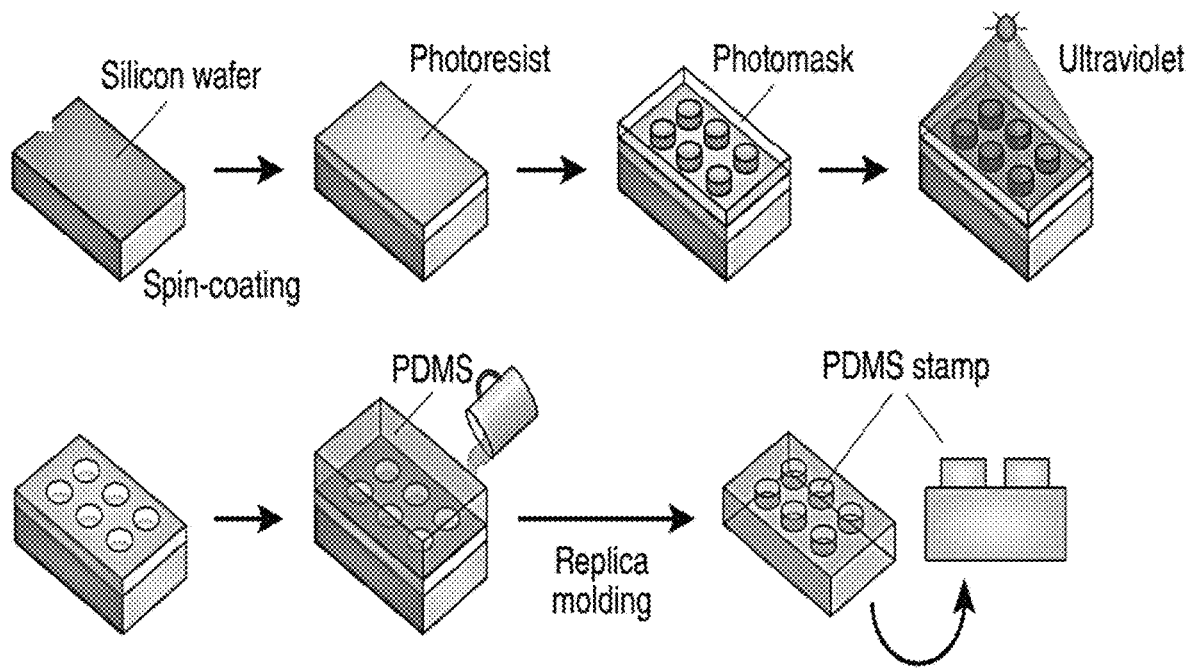
FIG. 10A-B shows exemplary embodiments of fabrication methods for microfluidic chips.
Figure 10B:
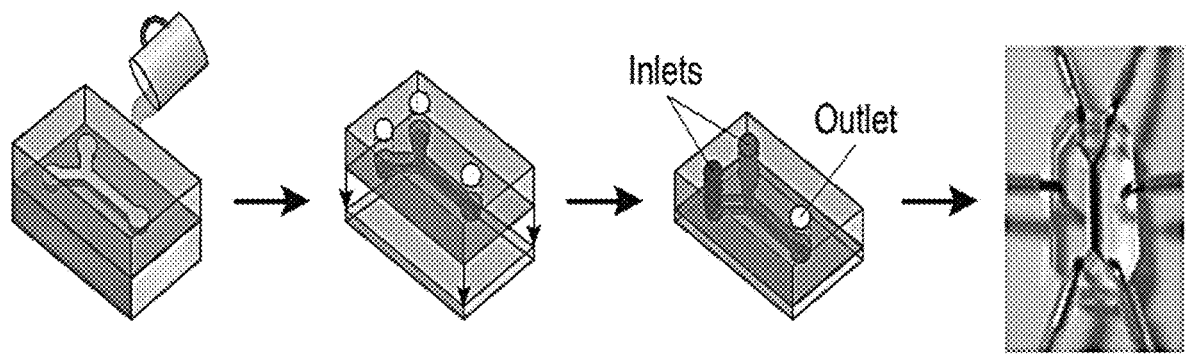
Figure 12A:
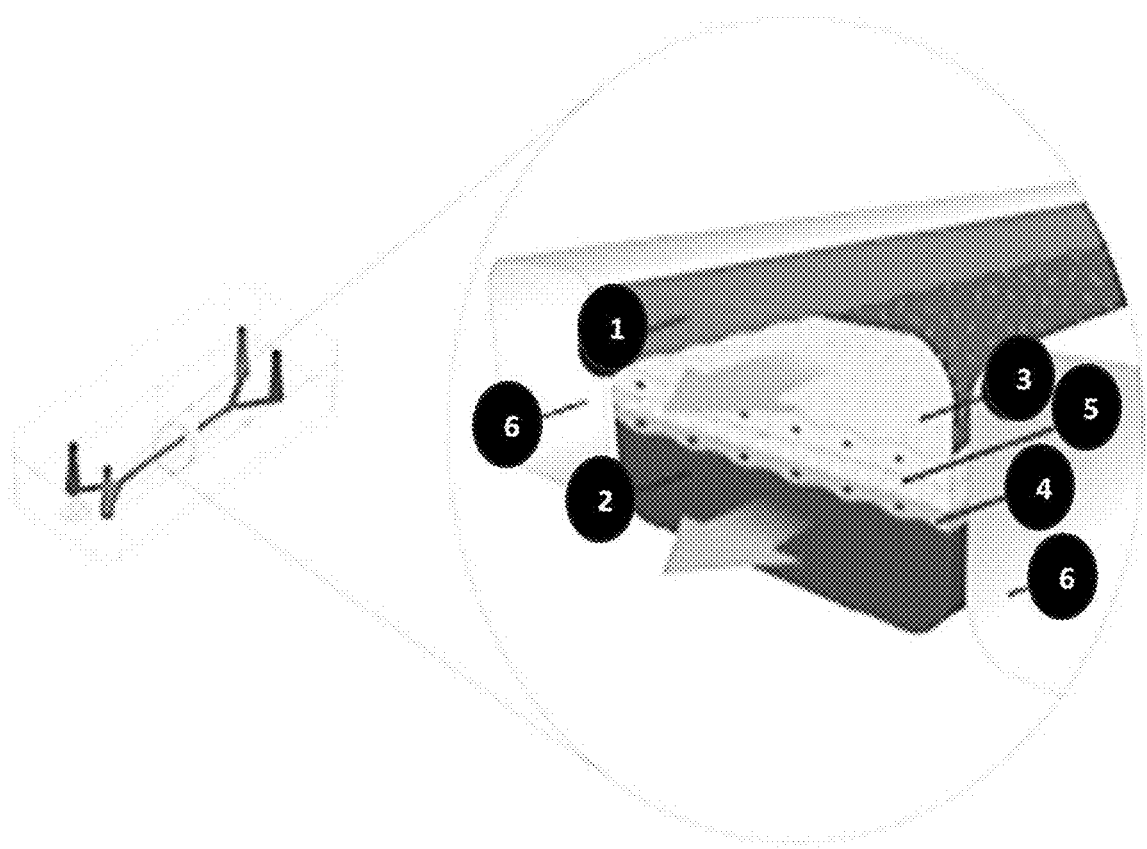

Microfluidic chips, devices, and systems contemplated for use in discovering epigenetic signatures; obtaining reference epigenetic signatures; and for comparative epigenetic signatures; etc., include but are not limited to chips described in Bhatia and Ingber, "Microfluidic organs-on-chips." Nature Biotechnology, 32(8):760-722, 2014; and related patent applications; and further include a wide range of chips of which some are briefly described in Zhang and Radisic, "Organ-on-a-chip devices advance to market." Lab On A Chip, (2017), for some examples, see FIG. 9A-B, herein incorporated by reference in its entirety. The following section is merely for providing nonlimiting examples of embodiments that may find use as microfluidic devices. Moreover, exemplary embodiments of ECM, gels, etc., may find use with any microfluidic device used for obtaining epigenetic signatures.

It is not meant to limit the type of organ-chip intended for use in generating an epigenetic signature. Indeed, in addition to gut-on-chips (intestine-chips), epigenetic signatures may be obtained from embodiments of a Heart-Chip; a blood-brain-barrier (BBB)-Chip (Brain-Chip); and combinations of chips, e.g. a three coupled chip model having influx and/or efflux across the blood-brain barrier (BBB); a Kidney Proximal Tubule-Chip"; spinal motor neuron-chip; etc. Such combinations may also include a Heart-Chip.

It is not meant to limit the type of cells added to organ-chips, including but not limited to white blood cells, immune cells, etc.

It is not meant to limit the type of epigenetic signature. Indeed, in addition to generating an epigenetic signature from a healthy organ-chip, epigenetic signatures may be obtained from TNFalpha induced inflammation of organ-chips described herein. Organ-on-chip systems can be used to simulate pathological stressors: The BBB-Chip and Heart-Chip was previously used to model inflammation upon treatment with TNF-alpha. The response to TNF-alpha depended on the presence of astrocytes or pericytes in the system, with TNF-alpha upregulating granulocyte colony stimulating factor as well as interleukin 6 and 8 secretion (Herlan, et al., "Distinct Contributions of Astrocytes and Pericytes to Neuroinflammation Identified in a 3D Human Blood-Brain Barrier on a Chip." PLoS One. 11(3): e0150360, 2016)).

Thus, is not meant to limit the type of treatment of an organ-chip, including but not limited to inflammatory induction, such as TNFalpha treatment of a heart-chip, TNFalpha treatment of a brain-chip; and a stress treatment, such as hypoxia, nutrient depravation, etc. Thus, in some embodiments, organ-chips as described herein are contemplated for use to profile tissue-specific EVs at baseline and in response to various external stress signals. in some embodiments, organ-chips as described herein are contemplated for decoupling cell populations or analyzing separate cell samples from the same chip.

In some embodiments, organ-chips intended for use in generating an epigenetic signature may be perfused with medium, wherein the medium simulates (reflects) human biofluids.

More specifically, one embodiment of a Heart-Chip comprises human cardiomyocytes and a channel-separating porous membrane covered with a primary human endothelial cell monolayer, on the opposite side of the cardiomyocytes. One embodiment of a Heart-Chip comprises a cardiac channel with hiPSC-derived cardiomyocytes and a vascular channel with human cardiac primary microvascular endothelial cells (see, for one example, Maoz, et al., "Organs-on-Chips with combined multi-electrode array and transepithelial electrical resistance measurement capabilities." Lab Chip. 17(13):2294-2302 (2017). Heart-Chip technology was used to study contractile function and calcium handling in genetic disorders like Barth syndrome. Wang, et al., "Modeling the mitochondrial cardiomyopathy of Barth syndrome with induced pluripotent stem cell and heart-on-chip technologies." Nat Med. 2014 June; 20(6):616-23.

The microfluidic Heart-Chip model, as proposed here, may also be capable of recapitulating inflammatory responses to tumor necrosis factor alpha (TNF-alpha). TNF-alpha challenge led to compromised endothelial barrier function, thus allowing a cardioactive drug (isoproterenol) to penetrate the barrier and modulate the cardiac beat rate, which did not happen in non-challenged isoproterenol dosed control Heart-Chips. Maoz, et al., "A linked organ-on-chip model of the human neurovascular unit reveals the metabolic coupling of endothelial and neuronal cells." Nat Biotechnol. 2018 October; 36(9):865-874.

More specifically, one embodiment of a blood-brain-barrier (BBB)-Chip (Brain-Chip); such as comprising a BBB and brain parenchyma (e.g. neurons, such as hippocampal granular neurons, microglia and glial cells); comprising a BBB-channel with endothelial cells and pericytes and a brain parenchymal channel with astrocytes, glia (including microglia), and cortical neurons. Maoz, et al., "A linked organ-on-chip model of the human neurovascular unit reveals the metabolic coupling of endothelial and neuronal cells." Nat Biotechnol. 36(9):865-874 2018. In one preferred embodiment, endothelial cells are hiPSC-derived endothelial cells. hiPSC-derived endothelial cells were shown to improve neuronal development Sances, et al., "Human iPSC-Derived Endothelial Cells and Microengineered Organ-Chip Enhance Neuronal Development." Stem Cell Reports. 10(4):1222-1236 2018. In some embodiments, endothelial cells are primary endothelial cells.

One embodiment of a BBB-Chip is contemplate for use herein, was used to study the metabolic coupling between the BBB and neurons as well as the effects of drugs such as methamphetamine on this system (Maoz, et al., "A linked organ-on-chip model of the human neurovascular unit reveals the metabolic coupling of endothelial and neuronal cells." Nat Biotechnol. 36(9):865-874 2018).

In some embodiments, readouts measure the effect of inflammatory cytokines on organ-chips as described herein, for one example, to measure the effect upon BBB barrier function and cytokine release. Herlan, et al., "Distinct Contributions of Astrocytes and Pericytes to Neuroinflammation Identified in a 3D Human Blood-Brain Barrier on a Chip." PLoS One. 11(3):e0150360, 2016). In some embodiments, readouts are from assays, such as RNA-Seq or qSMLM.

More specifically, one embodiment of a kidney Proximal Tubule-Chip, e.g. one embodiment of a kidney-on-a-chip is contemplated for use in which human kidney proximal tubular epithelial cells are cultured on top of a porous membrane separating two channels, enabling analysis of transcellular transport, uptake and secretion. In some embodiments, a kidney-chip comprises of the human kidney cultured on top of a porous membrane separating two channels. Parenchyma refers to epithelial tissue (including renal tubules and corpuscles) whereas blood vessels, nerves, and supporting connective tissue of the kidney comprise kidney stroma.

Additional embodiments of chips contemplated for use as described herein, include one embodiment of a chip comprising spinal motor neurons and BMECs from human induced pluripotent stem cells (iPSCs). Sances, et al., "Human iPSC-Derived Endothelial Cells and Microengineered Organ-Chip Enhance Neuronal Development." Stem Cell Reports. 10(4):1222-1236 2018.

In some embodiments, organ-chips may be provided using induced pluripotent stem cell (iPSC)-derived cells and/or primary human tissue-derived cells, such as primary cells and primary cell cultures derived from tissue biopsies and isolated blood cells, e.g. PBMCs.

In some embodiments, organ-chips may be perfused with medium comprising extra-cellular vesicles (EVs) derived (generated from then harvested) from other cell types, e.g.

from peripheral blood monocytes (PBMCs); RBCs from healthy human volunteers as blind samples, dendritic cells, etc., see, exemplary method in Koe, et al., "Red Blood Cells: A Source of Extracellular Vesicles." Methods Mol Biol. 1660:15-22 (2017). In brief, Peripheral blood monocytes will be isolated from the Buffy coats of healthy human blood donors by Ficoll-density gradient followed by magnetic bead separation for CD41+ monocytes. Cells will be cultured for 6 days (in the presence of IL-4+GM-CSF) and the supernatant collected, centrifuged at 3000 g×30 min (see, exemplary method in Esser, et al., Exosomes from human macrophages and dendritic cells contain enzymes for leukotriene biosynthesis and promote granulocyte migration." J Allergy Clin Immunol. 126(5):1032-40, (2010). Processed supernatant will be stored at −80° C., if not used immediately.

In some embodiments, organ-chips are evaluated for effects of immune cell-derived EVs on the cellular transcriptome on the Brain-Chip. In some embodiments, effects of immune cell-derived EVs will be evaluated on the cellular transcriptome on a Brain-Chip, such that cell-type specific responses may be evaluated. In some embodiments, changes in the release and content of EVs from an organ-chip, such as a Brain-Chip; a Heart-Chip, etc. will be monitored. In some embodiments, such organ-chips may undergo treatments as described herein. In some embodiments, organ-chips as described herein are contemplated for use in identifying tissue-specific EV markers and EV-RNA contents, such as for heart; brain; and immune cells. In some embodiments, organ-chips as described herein are contemplated for use in testing signaling moieties.

II. Closed Top Chips.

The present disclosure relates to gut-on-chips, such as fluidic devices comprising one or more cells types for the simulation one or more of the function of gastrointestinal tract components. Accordingly, the present disclosure additionally describes closed-top intestine-on-chips, see, e.g. schematic in FIG. 14A-B.

It is not meant to limit the type of closed top chip. Indeed, in addition to gut-on-chips, epigenetic signatures may be obtained from other types of organ-chips, exemplary chips are described as follows and herein.

Figure 14A:
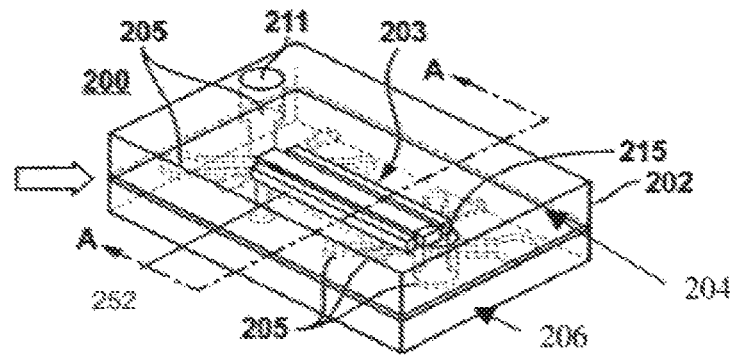
FIG. 14A illustrates one exemplary perspective view of a microfluidic device with microfluidic channels in accordance with an embodiment.
Figure 14B:
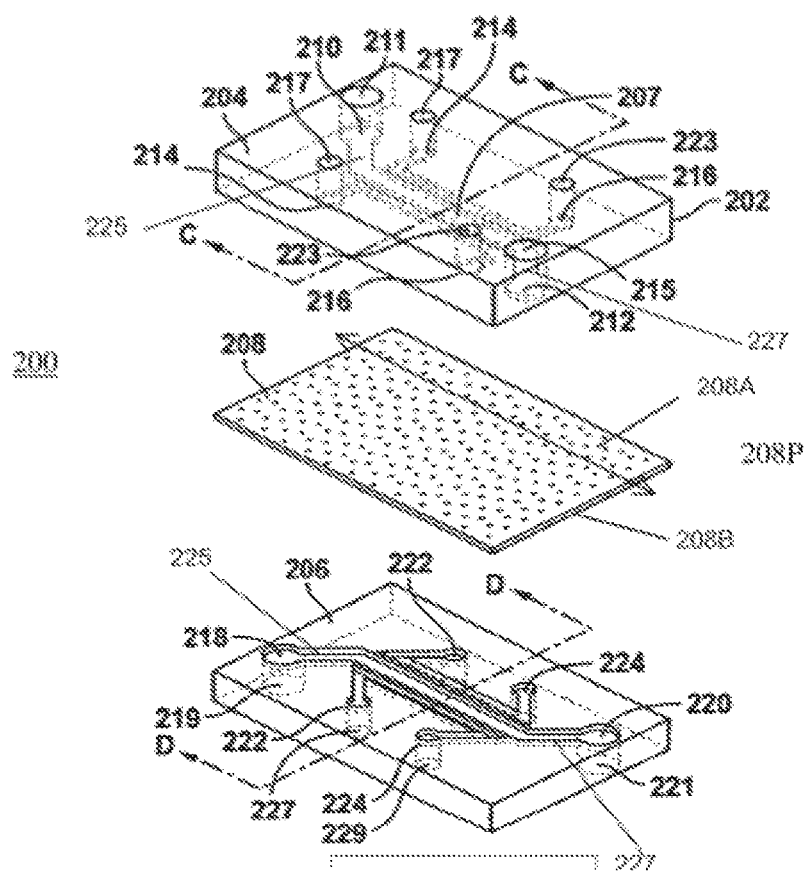
FIG. 14B illustrates one exemplary exploded view of the device in accordance with an embodiment, showing a microfluidic channel in a top piece and a microfluidic channel in a bottom piece, separated by a membrane.

FIG. 14A-14B illustrates a perspective view of the devices in accordance with some embodiments described herein. For example, as shown in FIGS. 14A-14B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is only exemplary and not limited to the configuration shown in FIG. 14A-14B. While operating chambers 252 (e.g., as a pneumatics means to actuate the membrane 208, see the International Appl. No. PCT/US2009/050830 for further details of the operating chambers, the content of which is incorporated herein by reference in its entirety) are shown in FIGS. 14A-14B, they are not required in all of the embodiments described herein. In some embodiments, the devices do not comprise operating chambers on either side of the first chamber and the second chamber. For example, FIG. 14B shows a device that does not have an operating channel on either side of the first chamber and the second chamber. In other embodiments, the devices described herein can be configured to provide other means to actuate the membrane, e.g., as described in the International Pat. Appl. No. PCT/US2014/071570, the content of which is incorporated herein by reference in its entirety.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are incorporated herein by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof. As used herein, the term "rigid" refers to a material that is stirr and does not bend easily, or maintains very close to its original form after pressure has been applied to it. The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof. As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally or alternatively, at least a portion of the first structure 204 and/or second structure 206 can be made of non-flexible or rigid materials like glass, silicon, hard plastic, metal, or any combinations thereof.

The membrane 208 can be made of the same material as the first structure 204 and/or second structure 206 or a material that is different from the first structure 204 and/or second structure 206 of the devices described herein. In some embodiments, the membrane 208 can be made of a rigid material. In some embodiments, the membrane is a thermoplastic rigid material. Examples of rigid materials that can be used for fabrication of the membrane include, but are not limited to, polyester, polycarbonate or a combination thereof. In some embodiments, the membrane 208 can comprise a flexible material, e.g., but not limited to PDMS. Additional information about the membrane is further described below.

In some embodiments, the first structure and/or second structure of the device and/or the membrane can comprise or is composed of an extracellular matrix polymer, gel, and/or scaffold. Any extracellular matrix can be used herein, including, but not limited to, silk, chitosan, elastin, collagen, proteoglycans, hyaluronic acid, collagen, fibrin, and any combinations thereof.

The device in FIG. 14A can comprise a plurality of access ports 205. In addition, the branched configuration 203 can comprise a tissue-tissue interface simulation region (membrane 208 in FIG. 14B) where cell behavior and/or passage of gases, chemicals, molecules, particulates and cells are monitored. FIG. 14B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204, 206 when the portions 204, 206 are mounted to one another to form the overall body.

The first outer body portion or first structure 204 can have a thickness of any dimension, depending, in part, on the height of the first chamber 204. In some embodiments, the thickness of the first outer body portion or first structure 204 can be about 1 mm to about 100 mm, or about 2 mm to about 75 mm, or about 3 mm to about 50 mm, or about 3 mm to about 25 mm. In some embodiments, the first outer body portion or first structure 204 can have a thickness that is more than the height of the first chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the first outer body portion or first structure 204 as thin as possible such that cells on the membrane can be visualized or detected by microscopic, spectroscopic, and/or electrical sensing methods.

The second outer body portion or second structure 206 can have a thickness of any dimension, depending, in part, on the height of the second chamber 206. In some embodiments, the thickness of the second outer body portion or second structure 206 can be about 50 µm to about 10 mm, or about 75 µm to about 8 mm, or about 100 µm to about 5 mm, or about 200 µm to about 2.5 mm. In one embodiment, the thickness of the second outer body portion or second structure 206 can be about 1 mm to about 1.5 mm. In one embodiment, the thickness of the second outer body portion or second structure 206 can be about 0.2 mm to about 0.5 mm. In some embodiments, the second outer first structure and/or second structure portion 206 can have a thickness that is more than the height of the second chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the second outer body portion or second structure 206 as thin as possible such that cells on the membrane can be visualized or detected by microscopic, spectroscopic, and/or electrical sensing methods.

In some embodiments, the first chamber and the second chamber can each independently comprise a channel. The channel(s) can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 14B illustrates an exploded view of the device in accordance with an embodiment. As shown in FIG. 14B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 14B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

The device 200 can also comprise an outlet channel 227 connecting an outlet fluid port 212 to the first chamber 204. The outlet channels and outlet ports can also be used to introduce cells, agents (e.g., but not limited to, stimulants, drug candidate, particulates), airflow, and/or cell culture media into the first chamber 204.

Although the inlet and outlet apertures 211, 215 are shown on the top surface of the first structure 204 and are located perpendicular to the inlet and outlet channels 225, 227, one or more of the apertures 211, 215 can be located on one or more lateral surfaces of the first structure and/or second structure such that at least one of the inlet and outlet apertures 211, 215 can be in-plane with the inlet and/or outlet channels 225, 227, respectively, and/or be oriented at an angle from the plane of the inlet and/or outlet channels 225, 227.

In another embodiment, the fluid passing between the inlet and outlet fluid ports can be shared between the first chamber 204 and second chamber 206. In either embodiment, characteristics of the fluid flow, such as flow rate, fluid type and/or composition, and the like, passing through the first chamber 204 can be controllable independently of fluid flow characteristics through the second chamber 206 and vice versa.

In some embodiments, while not necessary, the first structure 204 can include one or more pressure inlet ports 214 and one or more pressure outlet ports 216 in which the inlet ports 214 are in communication with corresponding apertures 217 located on the outer surface of the device 200. Although the inlet and outlet apertures are shown on the top surface of the first structure 204, one or more of the apertures can alternatively be located on one or more lateral sides of the first structure and/or second structure. In operation, one or more pressure tubes (not shown) connected to an external force source (e.g., pressure source) can provide positive or negative pressure to the device via the apertures 217. Additionally, pressure tubes (not shown) can be connected to the device 200 to remove the pressurized fluid from the outlet port 216 via the apertures 223. It should be noted that the device 200 can be set up such that the pressure port 214 is an outlet and pressure port 216 is an inlet. It should be noted that although the pressure apertures 217, 223 are shown on the top surface of the first structure 204, one or more of the pressure apertures 217, 223 can be located on one or more side surfaces of the first structure 204.

Referring to FIG. 14B, in some embodiments, the second structure 206 can include one or more inlet fluid ports 218 and one or more outlet fluid ports 220. As shown in FIG. 14B, the inlet fluid port 218 is in communication with aperture 219 and outlet fluid port 220 is in communication with aperture 221, whereby the apertures 219 and 221 are located on the outer surface of the second structure 206. Although the inlet and outlet apertures are shown on the surface of the second structure, one or more of the apertures can be alternatively located on one or more lateral sides of the second structure.

As with the first outer body portion or first structure 204 described above, one or more fluid tubes connected to a fluid source can be coupled to the aperture 219 to provide fluid to the device 200 via port 218. Additionally, fluid can exit the device 200 via the outlet port 220 and outlet aperture 221 to a fluid reservoir/collector or other component. It should be noted that the device 200 can be set up such that the fluid port 218 is an outlet and fluid port 220 is an inlet.

In some embodiments, the second outer body portion and/or second structure 206 can include one or more pressure inlet ports 222 and one or more pressure outlet ports 224. In some embodiments, the pressure inlet ports 222 can be in communication with apertures 227 and pressure outlet ports 224 are in communication with apertures 229, whereby apertures 227 and 229 are located on the outer surface of the second structure 206. Although the inlet and outlet apertures are shown on the bottom surface of the second structure 206, one or more of the apertures can be alternatively located on one or more lateral sides of the second structure. Pressure tubes connected to an external force source (e.g., pressure source) can be engaged with ports 222 and 224 via corresponding apertures 227 and 229. It should be noted that the device 200 can be set up such that the pressure port 222 is an outlet and fluid port 224 is an inlet.

In some embodiments where the operating channels (e.g., 252 shown in FIG. 14A) are not mandatory, the first structure 204 does not require any pressure inlet port 214, pressure outlet port 216. Similarly, the second structure 206 does not require any pressure inlet port 222 or pressure outlet port 224.

In an embodiment, the membrane 208 is mounted between the first structure 204 and the second structure 206, whereby the membrane 208 is located within the first structure 204 and/or second structure 206 of the device 200 (see, e.g., FIG. 14B). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, the membrane 208 in one embodiment can be made of a material which allows the membrane 208 to undergo stress and/or strain in response to an external force (e.g., cyclic stretching or pressure). In one embodiment, the membrane 208 can be made of a material which allows the membrane 208 to undergo stress and/or strain in response to pressure differentials present between the first chamber 204, the second chamber 206 and the operating channels 252. Alternatively, the membrane 208 is relatively inelastic or rigid in which the membrane 208 undergoes minimal or no movement.

In some embodiments where the device simulates a function of a liver tissue, the membrane can be rigid.

The first chamber 204 and/or the second chamber 206 can have a length suited to the need of an application (e.g., a physiological system to be modeled), desirable size of the device, and/or desirable size of the view of field. In some embodiments, the first chamber 204 and/or the second chamber 206 can have a length of about 0.5 cm to about 10 cm. In one embodiment, the first chamber 204 and/or the second chamber 206 can have a length of about 1 cm to about 3 cm. In one embodiment, the first chamber 204 and/or the second chamber 206 can have a length of about 2 cm.

The width of the first chamber and/or the second chamber can vary with desired cell growth surface area. The first chamber 204 and the second chamber 206 can each have a range of width dimension (shown as W in FIG. 14B) between 100 microns and 50 mm, or between 200 microns and 10 mm, or between 200 microns and 1500 microns, or between 400 microns and 1 mm, or between 50 microns and 2 mm, or between 100 microns and 5 mm. In some embodiments, the first chamber 204 and the second chamber 206 can each have a width of about 500 microns to about 2 mm. In some embodiments, the first chamber 204 and the second chamber 206 can each have a width of about 1 mm.

In some embodiments, the widths of the first chamber and the second chamber can be configured to be different, with the centers of the chambers aligned or not aligned. In some embodiments, the channel heights, widths, and/or cross sections can vary along the length of the devices described herein.

The heights of the first chamber and the second chamber can vary to suit the needs of desired applications (e.g., to provide a low shear stress, and/or to accommodate cell size). The first chamber and the second chamber of the devices described herein can have the same heights or different heights. In some embodiments, the height of the second chamber 206 can be substantially the same as the height of the first chamber 204.

In some embodiments, the height of at least a length portion of the first chamber 204 (e.g., the length portion where the cells are designated to grow) can be substantially greater than the height of the second chamber 206 within the same length portion. For example, the height ratio of the first chamber to the second chamber can be greater than 1:1, including, for example, greater than 1.1:1, 1.5:1, 2:1, 2.5:1, 3:1, 3.5:1, 4:1, 4.5:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1. In some embodiments, the height ratio of the first chamber to the second chamber can range from 1.1:1 to about 50:1, or from about 2.5:1 to about 50:1, or from 2.5 to about 25:1, or from about 2.5:1 to about 15:1. In one embodiment, the height ratio of the first chamber to the second chamber ranges from about 1:1 to about 20:1. In one embodiment, the height ratio of the first chamber to the second chamber ranges from about 1:1 to about 15:1. In one embodiment, the height ratio of the first chamber to the second chamber can be about 10:1.

The height of the first chamber 204 can be of any dimension, e.g., sufficient to accommodate cell height and/or to permit a low shear flow. For example, in some embodiments, the height of the first chamber can range from about 100 m to about 50 mm, about 200 µm to about 10 mm, about 500 µm to about 5 mm, or about 750 um to about 2 mm. In one embodiment, the height of the first chamber can be about 150 um. In one embodiment, the height of the first chamber can be about 1 mm.

The height of the second chamber 206 can be of any dimension provided that the flow rate and/or shear stress of a medium flowing in the second chamber can be maintained within a physiological range, or does not cause any adverse effect to the cells. In some embodiments, the height of the second chamber can range from 20 μm to about 1 mm, or about 50 μm to about 500 μm, or about 75 μm to about 400 μm, or about 100 μm to about 300 μm. In one embodiment, the height of the second chamber can be about 150 μm. In one embodiment, the height of the second chamber can be about 100 μm.

The first chamber and/or the second chamber can have a uniform height along the length of the first chamber and/or the second chamber, respectively. Alternatively, the first chamber and/or the second chamber can each independently have a varying height along the length of the first chamber and/or the second chamber, respectively. For example, a length portion of the first chamber can be substantially taller than the same length portion of the second chamber, while the rest of the first chamber can have a height comparable to or even smaller than the height of the second chamber.

In some embodiments, the first structure and/or second structure of the devices described herein can be further adapted to provide mechanical modulation of the membrane. Mechanical modulation of the membrane can include any movement of the membrane that is parallel to and/or perpendicular to the force/pressure applied to the membrane, including, but are not limited to, stretching, bending, compressing, vibrating, contracting, waving, or any combinations thereof. Different designs and/or approaches to provide mechanical modulation of the membrane between two chambers have been described, e.g., in the International Patent App. Nos. PCT/US2009/050830, and PCT/US2014/071570, the contents of which are incorporated herein by reference in their entireties, and can be adapted herein to modulate the membrane in the devices described herein.

In some embodiments, the devices described herein can be placed in or secured to a cartridge. In accordance with some embodiments of some aspects described herein, the device can be integrated into a cartridge and form a monolithic part. Some examples of a cartridge are described in the International Patent App. No. PCT/US2014/047694, the content of which is incorporated herein by reference in its entirety. The cartridge can be placed into and removed from a cartridge holder that can establish fluidic connections upon or after placement and optionally seal the fluidic connections upon removal. In some embodiments, the cartridge can be incorporated or integrated with at least one sensor, which can be placed in direct or indirect contact with a fluid flowing through a specific portion of the cartridge during operation. In some embodiments, the cartridge can be incorporated or integrated with at least one electric or electronic circuit, for example, in the form of a printed circuit board or flexible circuit. In accordance with some embodiments of some aspects described herein, the cartridge can comprise a gasketing embossment to provide fluidic routing.

In some embodiments, the cartridge and/or the device described herein can comprise a barcode. The barcode can be unique to types and/or status of the cells present on the membrane. Thus, the barcode can be used as an identifier of each device adapted to mimic function of at least a portion of a specific tissue and/or a specific tissue-specific condition. Prior to operation, the barcode of the cartridge can be read by an instrument so that the cartridge can be placed and/or aligned in a cartridge holder for proper fluidic connections and/or proper association of the data obtained during operation of each device. In some embodiments, data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

In some embodiments, the device can be connected to the cartridge by an interconnect adapter that connects some or all of the inlet and outlet ports of the device to microfluidic channels or ports on the cartridge. Some examples interconnect adapters are disclosed in U.S. Provisional Application No. 61/839,702, filed on Jun. 26, 2013, and the International Patent Application No. PCT/US2014/044417 filed Jun. 26, 2014, the contents of each of which are hereby incorporated by reference in their entirety. The interconnect adapter can include one or more nozzles having fluidic channels that can be received by ports of the device described herein. The interconnect adapter can also include nozzles having fluidic channels that can be received by ports of the cartridge.

In some embodiments, the interconnect adaptor can comprise a septum interconnector that can permit the ports of the device to establish transient fluidic connection during operation, and provide a sealing of the fluidic connections when not in use, thus minimizing contamination of the cells and the device. Some examples of a septum interconnector are described in U.S. Provisional Application No. 61/810,944 filed Apr. 11, 2013, the content of which is incorporated herein by reference in its entirety.

Membrane: The membrane 208 is oriented along a plane 208P parallel to the x-y plane between the first chamber 204 and the second chamber 206 as shown in FIG. 14B. It should be noted that although one membrane 208 is shown in FIG. 14B, more than one membrane 208 can be configured in devices which comprise more than two chambers. The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through. In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In some embodiments, a selectively-permeable membrane can allow certain cell types to pass therethrough but not other cell types.

The permeability of the membrane to individual matter/species can be determined based on a number of factors, including, e.g., material property of the membrane (e.g., pore size, and/or porosity), interaction and/or affinity between the membrane material and individual species/matter, individual species size, concentration gradient of individual species between both sides of the membrane, elasticity of individual species, and/or any combinations thereof. A porous membrane can have through-holes or pore apertures extending vertically and/or laterally between two surfaces 208A and 208B of the membrane (FIG. 14B), and/or a connected network of pores or void spaces (which can, for example, be openings, interstitial spaces or hollow conduits) throughout its volume. The porous nature of the membrane can be contributed by an inherent physical property of the selected membrane material, and/or introduction of conduits, apertures and/or holes into the membrane material.

In some embodiments, a membrane can be a porous scaffold or a mesh. In some embodiments, the porous scaffold or mesh can be made from at least one extracellular matrix polymer (e.g., but not limited to collagen, alginate, gelatin, fibrin, laminin, hydroxyapatite, hyaluronic acid, fibroin, and/or chitosan), and/or a biopolymer or biocompatible material (e.g., but not limited to, polydimethylsiloxane (PDMS), polyurethane, styrene-ethylene-butylene-styrene (SEBS), poly(hydroxyethylmethacrylate) (pHEMA), polyethylene glycol, polyvinyl alcohol and/or any biocompatible material described herein for fabrication of the device first structure and/or second structure) by any methods known in the art, including, e.g., but not limited to, electrospinning, cryogelation, evaporative casting, and/or 3D printing. See, e.g., Sun et al. (2012) "Direct-Write Assembly of 3D Silk/Hydroxyapatite Scaffolds for Bone Co-Cultures." Advanced Healthcare Materials, no. 1: 729-735; Shepherd et al. (2011) "3D Microperiodic Hydrogel Scaffolds for Robust Neuronal Cultures." Advanced Functional Materials 21: 47-54; and Barry III et al. (2009) "Direct-Write Assembly of 3D Hydrogel Scaffolds for Guided Cell Growth." Advanced Materials 21: 1-4, for examples of a 3D biopolymer scaffold or mesh that can be used as a membrane in the device described herein.

In some embodiments, a membrane can comprise an elastomeric portion fabricated from a styrenic block copolymer-comprising composition, e.g., as described in the International Pat. App. No. PCT/US2014/071611, can be adopted in the devices described herein, the contents of each of which are incorporated herein by reference in its entirety. In some embodiments, the styrenic block copolymer-comprising composition can comprise SEBS and polypropylene.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

The pores of the membrane (including pore apertures extending through the membrane 208 from the top 208A to bottom 208B surfaces thereof and/or a connected network of void space within the membrane 208) can have a cross-section of any size and/or shape. For example, the pores can have a pentagonal, circular, hexagonal, square, elliptical, oval, diamond, and/or triangular shape.

The cross-section of the pores can have any width dimension provided that they permit desired molecules and/or cells to pass through the membrane. In some embodiments, the pore size of the membrane should be big enough to provide the cells sufficient access to nutrients present in a fluid medium flowing through the first chamber and/or the second chamber. In some embodiments, the pore size can be selected to permit passage of cells (e.g., immune cells and/or cancer cells) from one side of the membrane to the other. In some embodiments, the pore size can be selected to permit passage of nutrient molecules. In some embodiments, the width dimension of the pores can be selected to permit molecules, particulates and/or fluids to pass through the membrane 208 but prevent cells from passing through the membrane 208. In some embodiments, the width dimension of the pores can be selected to permit cells, molecules, particulates and/or fluids to pass through the membrane 208. Thus, the width dimension of the pores can be selected, in part, based on the sizes of the cells, molecules, and/or particulates of interest. In some embodiments, the width dimension of the pores (e.g., diameter of circular pores) can be in the range of 0.01 microns and 20 microns, or in one embodiment, approximately 0.1-15 microns, or approximately 1-10 microns. In one embodiment, the pores have a width of about 7 microns.

In an embodiment, the porous membrane 208 can be designed or surface patterned to include micro and/or nanoscopic patterns therein such as grooves and ridges, whereby any parameter or characteristic of the patterns can be designed to desired sizes, shapes, thicknesses, filling materials, and the like.

The membrane 208 can have any thickness to suit the needs of a target application. In some embodiments, the membrane can be configured to deform in a manner (e.g., stretching, retracting, compressing, twisting and/or waving) that simulates a physiological strain experienced by the cells in its native microenvironment. In these embodiments, a thinner membrane can provide more flexibility. In some embodiments, the membrane can be configured to provide a supporting structure to permit growth of a defined layer of cells thereon. Thus, in some embodiments, a thicker membrane can provide a greater mechanical support. In some embodiments, the thickness of the membrane 208 can range between 70 nanometers and 100 µm, or between 1 µm and 100 µm, or between 10 and 100 µm. In one embodiment, the thickness of the membrane 208 can range between 10 µm and 80 µm. In one embodiment, the thickness of the membrane 208 can range between 30 µm and 80 µm. In one embodiment, the thickness of the membrane 208 can be about 50 µm.

While the membrane 208 generally have a uniform thickness across the entire length or width, in some embodiments, the membrane 208 can be designed to include regions which have lesser or greater thicknesses than other regions in the membrane 208. The decreased thickness area(s) can run along the entire length or width of the membrane 208 or can alternatively be located at only certain locations of the membrane 208. The decreased thickness area can be present along the bottom surface of the membrane 208 (i.e. facing second chamber 206), or additionally/alternatively be on the opposing surface of the membrane 208 (i.e. facing second chamber 204). It should also be noted that at least portions of the membrane 208 can have one or more larger thickness areas relative to the rest of the membrane, and capable of having the same alternatives as the decreased thickness areas described above.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In an embodiment, the cell attachment-promoting substances, matrix-forming formulations, and other compositions of matter are sterilized to prevent unwanted contamination. Sterilization can be accomplished, for example, by ultraviolet light, filtration, gas plasma, ozone, ethylene oxide, and/or heat. Antibiotics can also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In some embodiments, the membrane and/or other components of the devices described herein can be treated using gas plasma, charged particles, ultraviolet light, ozone, or any combinations thereof Using the devices described herein, one can study biotransformation, absorption, as well as drug clearance, metabolism, delivery, and toxicity. The activation of xenobiotics can also be studied. The bioavailability and transport of chemical and biological agents across epithelial layers as in a tissue or organ, e.g., parenchyma, and endothelial layers as in blood vessels, and across the liver for drug metabolism can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be detected and studied using the devices described herein. The impact of genetic content on response to the agents can be studied. The amount of protein and gene expression in response to chemical or biological agents can be determined. Changes in metabolism in response to chemical or biological agents can be studied as well using devices described herein.

In some embodiments, the devices described herein (e.g., a Liver-on-a-Chip) can be used to assess the clearance of a test compound. For clearance studies, the disappearance of a test compound can be measured (e.g. using mass spec) in the media of the top chamber, bottom chamber, or both chambers (divided by a membrane comprising liver cells).

For example, in accordance to one aspect of the invention, a Liver-on-Chip drug-metabolizing performance can be measured by i) disposing a substrate compound with known liver metabolites in the media of the top chamber, bottom chamber, or both chambers; and ii) measuring the amount of generated metabolite in the media of the top chamber, bottom chamber or both chambers (e.g. using mass spec). As is known in the art, the choice of the substrate and measured metabolite can help provide information on specific liver drug-metabolism enzymes (e.g. CYP450 isoforms, Phase II enzymes, etc.) In some embodiments, the devices described herein (e.g., a Liver-on-a-Chip) can be used to assess the induction or inhibition potential of a test compound. For induction or inhibition studies a variety of tests are contemplated. For example, induction of CYP3A4 activity in the liver is one of main causes of drug-drug interactions, which is a mechanism to defend against exposure to drugs and toxin, but can also lead to unwanted side-effects (toxicity) or change the efficacy of a drug. A reliable and practical CYP3A induction assay with human hepatocytes in a 96-well format has been reported, where various 96-well plates with different basement membrane were evaluated using prototypical inducers, rifampicin, phenytoin, and carbamazepine. See Drug Metab. Dispo. (2010) November; 38(11):1912-6.

According to one aspect of the invention, the induction or inhibition potential of a test compound at a test concentration can be evaluated by i) disposing the test compound in the media of the top chamber, bottom chamber or both chambers at the test concentration; ii) exposing the device for a selected period of time; and iii) assessing the induction or inhibition of liver enzymes by comparing liver performance to a measurement performed before the test compound was applied, to a measurement performed on a Liver-on-Chip that was subjected to a lower concentration of test compound (or no test compound at all), or both. In some embodiments, the liver performance measurement can comprise an RNA expression level. In some embodiments, the liver performance measurement comprises assessing drug-metabolizing capacity.

In some embodiments, the devices described herein (e.g., a Liver-on-a-Chip) can be used to identify in vivo metabolites of a test compound or agent, and optionally the in vivo ratio of these metabolites. According to one aspect of the invention, in vivo metabolites can be identified by i) disposing a test compound or agent in the media of the top chamber, bottom chamber, or both chambers; and ii) measuring the concentration of metabolites in the media of the top chamber, bottom chamber, or both chambers. In some embodiments, the measuring of the concentration of metabolites comprises mass spectroscopy.

In some embodiments, the devices described herein (e.g., a Liver-on-a-Chip) can be used to identify the toxicity of a test compound or agent at a test concentration. According to one aspect of the invention, toxicity can be evaluated by i) disposing a test compound in the media of the top chamber, bottom chamber, or both chambers; and ii) measuring one or more toxicity endpoints selected from the list of leakage of cellular enzymes (e.g., lactose dehydrogenase, alanine aminotransferase, aspartate aminotransferase) or material (e.g., adenosine triphosphate), variation in RNA expression, inhibition of drug-metabolism capacity, reduction of intracellular ATP (adenosine triphosphate), cell death, apoptosis, and cell membrane degradation.

Exemplary Methods of Making the Devices Described Herein.

Embodiments of various devices comprising a first chamber, a second chamber, and a membrane can enable us to leverage the control of microfluidic technology for device fabrication. In some embodiments, the devices described herein can be manufactured using any conventional fabrication methods, including, e.g., injection molding, embossing, etching, casting, machining, stamping, lamination, photolithography, or any combinations thereof. Soft lithography techniques are described in "Soft Lithography in Biology and Biochemistry," by Whitesides, et al., published Annual Review, Biomed Engineering, 3.335-3.373 (2001), as well as "An Ultra-Thin PDMS Membrane As A Bio/Micro-Nano Interface: Fabrication And Characterization", by Thangawng et al., Biomed Microdevices, vol. 9, num. 4, 2007, p. 587-95, both of which are hereby incorporated by reference.

Without wishing to be limiting, in some embodiments, the devices described herein can be produced as a monolithic device or as individual components (e.g., a first structure comprising a first chamber, a second structure comprising a second chamber, and a membrane), which can then be assembled together to form a device described herein. Each individual component can be produced by a conventional manufacturing method such as injection molding, extrusion, casting, lamination, embossing, compression molding, solvent casting, an additive manufacturing method (e.g., 3D printing), or any combinations thereof.

Once the first and second structures 204, 206 are formed and removed from their respective molds, the access ports can be made to access the chambers.

The membrane 208 can be engineered for a variety of purposes, some discussed above.

In some embodiments, the membrane 208 can be sandwiched between the first structure and the second structure, e.g., using an appropriate adhesive or epoxy, physical clamping and/or plasma bond between the two PDMS surfaces, in order to form a fluidic seal between the membrane with the first structure and the second structure.

After forming the body of the devices described herein, the first side of the membrane can be coated with an ECM composition according to one or more embodiments described herein. After formation of the ECM composition, tissue specific cells, e.g., hepatocytes, can be grown thereon.

In some embodiments, at least one layer of cells comprising blood vessel-associated cells (e.g., fibroblasts, smooth muscle cells, and/or endothelial cells) can be cultured on the second side of the membrane.

A. Closed Top Microfluidic Chips without Gels.

In one embodiment, closed top gut-on-chips, or other type of organ-chip, do not contain gels, either as a bulk gel or a gel layer. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips with Gels.

In one embodiment, closed top gut-on-chips do contain gels, such as a gel layer, or bulk gel, including but not limited to a gel matrix, hydrogel, etc. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips with Simulated Lumens.

A closed top gut-on-chip comprising a gel-lined simulated lumen may be used for generating a more physiological relevant model of gastrointestinal tissue. In some embodiments, closed top gut-on-chips further comprise a gel simulated three-dimensional (3-D) lumen. In other words, a 3-D lumen may be formed using gels by providing simulated intestinal villi (e.g. viscous fingers) and/or mimicking intestinal folds. In a preferred embodiment, the gel forms a lumen, i.e. by viscous fingering patterning.

Using viscous fingering techniques, e.g. viscous fingering patterning, a simulated intestinal lumen may be formed by numerous simulated intestinal villi structures. Intestinal villi (singular: villus) refer to small, finger-like projections that extend into the lumen of the small intestine. For example, healthy small intestine mucosa contains these small finger-like projections of tissue that are present along the lumen as folds of circular plica finger-like structures. A villus is lined on the luminal side by an epithelia cell layer, where the microvillus of the epithelial cells (enterocytes) faces the lumen (i.e. apical side). Viscous fingers may be long and broad, for mimicking villi in the duodenum of the small intestine, while thinner or shorter viscous fingers may be used for mimicking villi in other parts of the gastrointestinal tract. As one example, viscous fingers may be formed and used to mimic epithelial projections in the colon.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning." J Lab Autom. 2012 April; 17(2): 96-103, Author manuscript; available in PMC 2012 Jul. 16, herein incorporated by reference in its entirety. In one example of a viscous finger patterning method for use with microfluidic gut-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium.

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated intestinal villus.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular microenvironment, (e.g. MATRIGEL. In some embodiments, the first and second permeable matrixes can each independently comprise a polymer matrix. Methods to create a permeable polymer matrix are known in the art, including, e.g. but not limited to, particle leaching from suspensions in a polymer solution, solvent evaporation from a polymer solution, sold-liquid phase separation, liquid-liquid phase separation, etching of specific "block domains" in block co-polymers, phase separation to block-co-polymers, chemically cross-linked polymer networks with defined permeabilities, and a combination of two or more thereof.

Another example for making branched structures using fluids with differing viscosities is described in "Method And System For Integrating Branched Structures In Materials" to Katrycz, Publication number US20160243738, herein incorporated by reference in its entirety.

Regardless of the type of lumen formed by a gel and/or structure, cells can be attached to these structures either to lumen side of the gel and/or within the gel and/or on the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Microfluidic Chips.

Figure 15A:
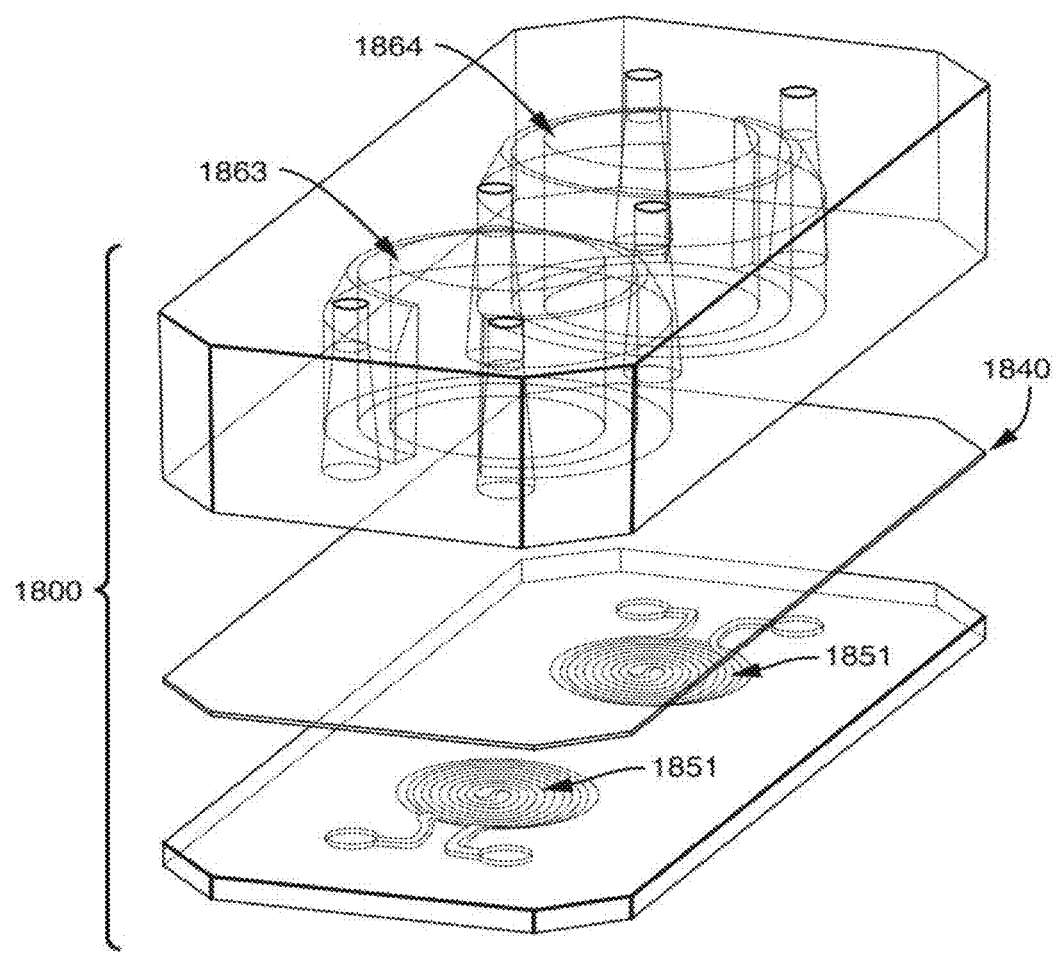
FIG. 15A shows one exemplary schematic of an open top microfluidic chip.
Figure 15B:
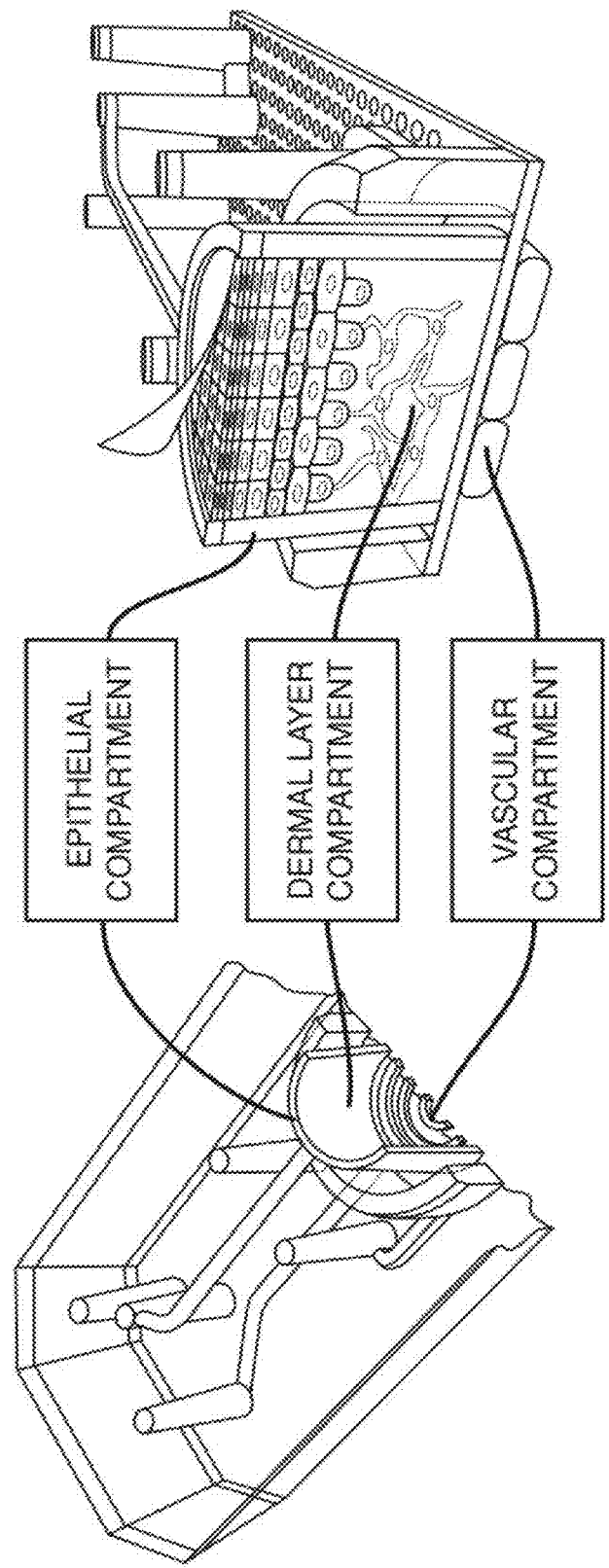
FIG. 15B shows two exemplary embodiments of an Intestinal Mucosa On-Chip (enteroids'-derived cells) modeling a simulated intestine comprising intestinal epithelium from up to four areas of the intestine. One embodiment as a schematic of a partial open top chip demonstrating channels and open area in relation to compartments in the chip (left). One embodiment as a schematic of a partial open top chip additionally demonstrating cells in the compartments of the chip (right). Comparative epithelial compartments include intestinal epithelium (enteroid/colonoid derived) from 4 different intestinal segments: duodenum, jejunum, ileum and colon. Stromal compartment includes intestinal fibroblasts+/−immune cells. Vascular compartment includes intestinal microvascular endothelium from small intestine and/or large intestine.

The present disclosure relates to gut-on-chips, such as fluidic devices comprising one or more cells types for the simulation one or more of the function of gastrointestinal tract components. Accordingly, the present disclosure additionally describes open-top gut-on-chips, see, e.g. schematic in FIG. 15A-B. FIG. 15A shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

It is not meant to limit the type of open top chips. Indeed, in addition to gut-on-chips, epigenetic signatures may be obtained from other types of organ-chips, exemplary chips are described herein.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

A. Open Top Microfluidic Chips without Gels.

In one embodiment, open top gut-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips with Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic chips comprise lumens formed by viscous fingering described herein for closed top chips.

Lumen gel structures may be used in several types of embodiments for open top microfluidic chips, e.g. epithelial cells or parenchymal cells can be attached to outside of the gel, or within the gel. In some embodiments, stromal cells are added within the gel. In some embodiments, stromal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels, with or without gels.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

IV. Chip Activation.

Open-Top Organ-Chip platform was chemically activated by sulfu sampo/buffer, such as HEPES, treatment (Emulate, Inc). Briefly, sulfu sampo and buffer were mixed together as specified by the instructions and added to the bottom spiraled shaped microfluidic channel and circular stromal chamber. The platform was then UV treated for 20 minutes using UV oven (e.g. 365 nm light and the bulb that generate the UV light are 9 Watt).

A. Chip Activation Compounds.

In one embodiment, bifunctional crosslinkers are used to attach one or more extracellular matrix (ECM) proteins. A variety of such crosslinkers are available commercially, including (but not limited to) the following compounds:

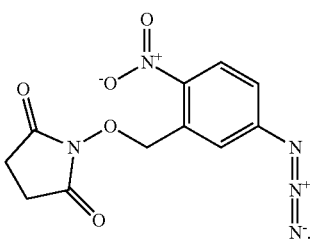

ANB-NOS (N-5-azido-2-nitrobenzoyloxysuccinimide)

-continued

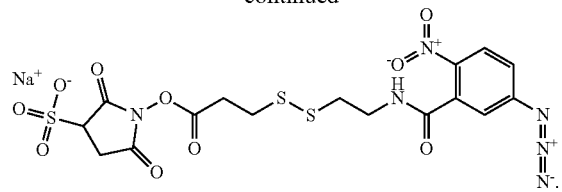

Sulfo-SAND (sulfosuccinimidyl 2-[m-azido-o-nitrobenzamido]ethyl-1,3'-dithiopropionate):

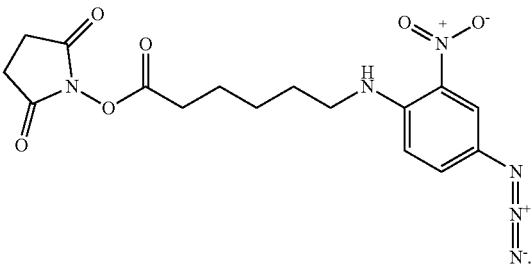

SANPAH (N-succinimidyl-6-[4'-azido-2'-nitrophenylamino]hexanoate)

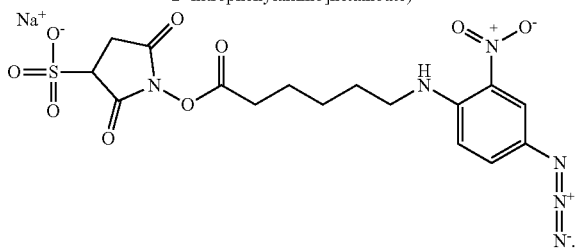

Sulfo-SANPAH (sulfosuccinimidyl-6-[4'-azido-2'-nitrophenylamino]hexanoate)

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups ($-NH_2$) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary methods of Chip Activation.
1. Prepare and sanitize hood working space
2. S-1 Chip Handling—Use aseptic technique, hold Chip using Carrier
   a. Use 70% ethanol spray and wipe the exterior of Chip package prior to bringing into hood
   b. Open package inside hood
   c. Remove Chip and place in sterile Petri dish (6 Chips/Dish)
   d. Label Chips and Dish with respective condition and Lot #
3. Surface Activation with Chip Activation Compound (light and time sensitive)
   a. Turn off light in biosafety hood
   b. Allow vial of Chip Activation Compound powder to fully equilibrate to ambient temperature (to prevent condensation inside the storage container, as reagent is moisture sensitive)
   c. Reconstitute the Chip Activation Compound powder with ER-2 solution
      i. Add 10 ml Buffer, such as HEPES, into a 15 ml conical covered with foil
      ii. Take 1 ml Buffer from above conical and add to chip Activation Compound (5 mg) bottle, pipette up and down to mix thoroughly and transfer to same conical
      iii. Repeat 3-5 times until chip Activation Compound is fully mixed
      iv. NOTE: Chip Activation Compound is single use only, discard immediately after finishing Chip activation, solution cannot be reused
   d. Wash channels
      i. Inject 200 ul of 70% ethanol into each channel and aspirate to remove all fluid from both channels
      ii. Inject 200 ul of Cell Culture Grade Water into each channel and aspirate to remove all fluid from both channels
      iii. Inject 200 ul of Buffer into each channel and aspirate to remove fluid from both channels
   e. Inject Chip Activation Compound Solution (in buffer) in both channels
      i. Use a P200 and pipette 200 ul to inject Chip Activation Compound/Buffer into each channel of each chip (200 ul should fill about 3 Chips (Both Channels))
      ii. Inspect channels by eye to be sure no bubbles are present. If bubbles are present, flush channel with Chip Activation Compound/Buffer until bubbles have been removed
   f. UV light activation of Chip Activation Compound Place Chips into UV light box
      i. UV light treat Chips for 20 min
      ii. While the Chips are being treated, prepare ECM Solution.
      iii. After UV treatment, gently aspirate Chip Activation Compound/Buffer from channels via same ports until channels are free of solution
      iv. Carefully wash with 200 ul of Buffer solution through both channels and aspirate to remove all fluid from both channels
      v. Carefully wash with 200 ul of sterile DPBS through both channels
      vi. Carefully aspirate PBS from channels and move on to: ECM-to-Chip VI. ECM-to-Chip
   A. Calculate total volume of ECM solution needed to coat Chips or hydrogel surfaces, these are exemplary ECM materials, as laminin may also be used with one or more ECM materials.
      1. Volume required per Chip=50 ul/Channel
      2. ECM diluent: PBS, prepared on ice
      3. Stock Concentrations for ECM coating:
         a. Collagen IV: 1 mg/ml (200 ul aliquots in −20° C.)
         b. Fibronectin: 1 mg/ml (50 ul aliquots in 4° C.)
         c. Matrigel: 10 mg/ml (200 ul aliquots in −20° C.)
      4. Working Concentrations for ECM coating:
         a. Collagen IV: 200 ug/ml
         b. Fibronectin:30 ug/ml
      5. Top Channel Coating: 50 ul Collagen IV (200 ug/ml) and Matrigel (100 ug/ml)
      6. Bottom Channel Coating: 50 ul Collagen IV (200 ug/ml) and Fibronectin (30 ug/ml)
   B. Load Channels with ECM solution.
      1. Place Chips in hood
      2. Pipette 50 µl of Top Channel Coating into Top Channel—keep the pipette plunger depressed until you see fluid come out opposite end of the channel, then take another pipette tip (200 µl tip) to close the outlet port. Once closed off, carefully remove the pipette tip, leaving the tip in the inlet port.
      3. Aspirate excess fluid from the surface of Chip (avoid direct contact with the port)
      4. Repeat 2b-2c, but with Bottom Channel Coating into Bottom Channel
      5. Incubate at 37 C for a minimum of 2 hours up to overnight
   C. Exemplary Matrigel Coating
      1. Thaw Matrigel on ice and keep chilled to prevent solidification.
      2. Prepare Matrigel
         a. Matrigel Stock Concentration: 10 mg/ml
         b. Matrigel Final Concentration: 250 µg/ml
         c. Determine the volume of Matrigel needed to coat 50 µl of each Top Channel and resuspend accordingly in cell culture media
         d. Transfer the seeded Chips into the hood
         e. Wash both channels of each chip twice with 200 ul media
         f. Before inserting the tips, add a drop of media to prevent formation of bubbles
         g. Leave 50 ul media in bottom channel (Tips inserted)
         h. Add 50 ul 250 ug/ml matrigel to top channel (Tips inserted)
         i. Incubate at 37 C overnight.
V. Cells-to-Chip—Chip Preparation.
   1. Transfer the ECM coated Chips into the hood
      a. Gently wash Chips after ECM coating
   2. Pipette 200 µl of DPBS into bottom channel inlet port—keep the pipette plunger depressed until you see fluid come out opposite end of channel and aspirate outflow
   3. Repeat the same procedure to wash top channel
   4. Pipette 200 µl of DPBS into top channel inlet port—keep the pipette plunger depressed until you see fluid come out opposite end of the channel, then take another pipette tip (200 µl) to close the outlet port. Once closed off, carefully remove the pipette tip, leaving the tip in the inlet port 5. Repeat the same with the bottom channel. Place back in incubator until cells are ready.

EXPERIMENTAL

Example: RNA (Gene) Expression Profiling Providing an Epigenetic Signature

Gene expression profiling refers to measurement of the activity (expression) of thousands of genes at once, to create a global picture of cellular function. As one example, RNA-Seq (Illumina, Inc. 5200 Illumina Way, San Diego, CA 92122), provides information on the sequences of genes in addition to their expression level. Thus, gene expression (RNA) patterns, at the level of transcription, under specific circumstances of contact with an agent, pathogen, etc., in a specific cell may provide a global picture of cellular function relative to an epigenetic signature.

As one example, total RNA can be extracted and used to generate biotin-labeled cRNA, e.g. using an Illumina Total-Prep RNA Amplification Kit (Ambion, Austin, TX). Biotin-labeled cRNA was then hybridized to Illumina HumanHT-12 whole genome expression beadchips (Illumina, San Diego, CA). The quality of the Illumina bead summary data can be assessed using the Bioconductor package Lumi. Data preprocessing may include variance stabilization and quantile normalization. To eliminate potentially confounding effects of RNA quality on gene expression, residuals may be calculated from the regression analysis of RIN values on gene expression and used for statistical analysis and WGCNA network construction. Outlier values may then be removed for each gene within a group using Grubbs' test (p<0.05). Statistical analysis comparing alcoholic and control groups may be performed using the Bioconductor package Limma to carry out a Bayesian two-tailed t-test. A false discovery rate (FDR) for each list of significantly regulated genes with nominal P values <0.05 may be estimated using the method of Benjamini and Hochberg (1995). Our systems approach to prioritizing individual genes may be based on integration of nominal statistical significance, gene network information and functional relevance. Therefore, to avoid omitting true positives, all genes with nominal P values <0.05 may be considered. After initial data processing, epigenetic data from controls and test samples may be used for generating epigenetic signatures. In some embodiments, epigenetic data from controls and test samples may be used for epigenetic network construction.

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

We claim:

1. A method comprising:
    a) providing a microfluidic device comprising at least one microfluidic channel, said microfluidic channel comprising endothelial cells of a first tissue; and
    b) providing a plurality of extracellular vesicles obtained from a human with a disease of a second tissue;
    c) introducing said extracellular vesicles into said microfluidic channel under conditions wherein said endothelial cells are exposed to said extracellular vesicles so as to create one or more exposed cells; and
    d) detecting a cell injury change in said one or more exposed cells.

2. The method of claim 1, further comprising flowing media at a flow rate through said microfluidic channel prior to step c).

3. The method of claim 2, wherein said extracellular vesicles are introduced by adding them to said flowing media.

4. The method of claim 1, wherein said human patient has a heart condition.

5. A method comprising:
    a) providing a microfluidic device comprising at least one microfluidic channel, said microfluidic channel comprising endothelial cells; and
    b) providing a plurality of extracellular vesicles obtained from a human patient, said human patient having a disease or condition;
    c) introducing said extracellular vesicles into said microfluidic channel under conditions wherein said endothelial cells are exposed to said extracellular vesicles so as to create one or more exposed cells; and
    d) detecting a change in said one or more exposed cells wherein said change comprises increased permeability of said endothelial cells.

6. The method of claim 5, further comprising flowing media at a flow rate through said microfluidic channel prior to step c).

7. The method of claim 5, wherein said human patient has a heart condition.

8. The method of claim 5, wherein said permeability is increased in comparison to endothelial cells exposed to extracellular vesicles obtained from a healthy human patient.

* * * * *